United States Patent
Foulkes et al.

(10) Patent No.: US 6,589,733 B1
(45) Date of Patent: Jul. 8, 2003

(54) METHODS OF PREPARING COMPOSITIONS COMPRISING CHEMICALS CAPABLE OF TRANSCRIPTIONAL MODULATORS

(75) Inventors: J. Gordon Foulkes, Huntington Station; Robert Franco, Spencerport; Franz Leichtfried, Bellerose; Christian Pieler, Westbury; John R. Stephenson, Rockville Centre, all of NY (US)

(73) Assignee: Osi Pharmaceuticals, Inc., Melville, NY (US)

( * ) Notice: Subject to any disclaimer, the term of this patent is extended or adjusted under 35 U.S.C. 154(b) by 0 days.

(21) Appl. No.: 08/463,398

(22) Filed: Jun. 5, 1995

Related U.S. Application Data

(62) Division of application No. 08/306,925, filed on Sep. 15, 1994, now abandoned, which is a continuation of application No. 08/026,270, filed on Mar. 4, 1993, now abandoned, which is a continuation of application No. 07/382,711, filed on Jul. 18, 1989, now abandoned.

(51) Int. Cl.$^7$ .............................. C12Q 1/68; C12Q 1/02; A61K 49/00

(52) U.S. Cl. ............................... 435/6; 424/9.1; 435/29

(58) Field of Search ............................. 424/9.1; 435/29, 435/6

(56) References Cited

U.S. PATENT DOCUMENTS

| | | |
|---|---|---|
| 4,535,058 A | 8/1985 | Weinber et al. |
| 4,601,978 A | 7/1986 | Karin |
| 4,699,877 A | 10/1987 | Cline et al. |
| 4,736,866 A | 4/1988 | Leder et al. |
| 4,738,922 A | 4/1988 | Haseltine et al. |
| 4,740,461 A | 4/1988 | Kaufman |
| 4,740,463 A | 4/1988 | Weinberg et al. |
| 4,761,367 A | 8/1988 | Edgell et al. |
| 4,761,371 A | 8/1988 | Bell et al. |
| 4,806,463 A | 2/1989 | Goodchild et al. |
| 4,810,643 A | 3/1989 | Souza |
| 4,827,079 A * | 5/1989 | Evans .......................... 800/304 |
| 4,861,709 A | 8/1989 | Ulitzer et al. |
| 4,885,238 A | 12/1989 | Reddel et al. |
| 4,935,363 A | 6/1990 | Brown et al. |
| 4,981,783 A | 1/1991 | Augenlicht |
| 4,981,784 A * | 1/1991 | Evans ............................ 435/6 |
| 4,981,790 A | 1/1991 | Haseltine et al. |
| 5,070,012 A | 12/1991 | Nolan et al. |
| 5,071,773 A | 12/1991 | Evans et al. |
| 5,075,229 A | 12/1991 | Hanson et al. |
| 5,262,300 A | 11/1993 | Evans et al. |

FOREIGN PATENT DOCUMENTS

| | | |
|---|---|---|
| EP | 117058 | 8/1984 |
| EP | 332104 | 9/1989 |
| WO | WO8902472 | 3/1989 |

OTHER PUBLICATIONS

Tocci et al: J of Immunology 143(2): 718, 1989.*
Anderson, R. et al. (1990) "Metal–Dependent Binding of A Nuclear Factor to the Rat Metallothionein–I Promoter," Nucleic Acids Research 18 (20): 6049–6055.
Angel, P. et al., (1987 A) "Phorbol Ester–Inducible Genes Contain A Common Cis Element Recognized by An TPA–Modulated Trans–Acting Factor," Cell 49: 729–739.
Angel, P. et al., (1987 B) "12–O–Tetradecanoyl–Phorbol–13–Acetate Induction of the Human Collagenase Gene Is Mediated by an Inducible Enhancer Element Located in the 5'–Flanking Region," Molecular and Cellular Biology, 7: 2256–2266.
Bender, Alan and George F. Sprague, Jr. (1986) "Yeast Peptide Pheromones, a–Factor and α–Factor and α–Factor, Activate a Common Response Mechanism in Their Target Cells," Cell 47: 929–937(Exhibit 2).
Bickel, M. et al, (1988) "Granulocyte–Macrophage Colony–Stimulating Factor Regulation in Murine T Cells and Its Relation to Cyclosporin A," Ex. Hematol. 16: 691–695.
Blumberg, P. (1988) "Protein Kinase C as the Receptor for the Phorbol Ester Tumor Promoters: Sixth Rhoads Memorial Award Lecture," Cancer Research 48: 1–8.
Brasier, A. et al. (1989) "Optimized Use of the Firefly Luciferase Assay as a Reporter Gene in Mammalian Cell Lines," BioTechniques 7(10): 1116–1122.
Brenner C. et al., (1989) "Message Amplification Phenotyping (MAPPing): A Technique to Simultaneously Measure Multiple mRNAs from Small Numbers of Cells," BioTechniques 7 (10): 1096–1103.
Cao, T., (1989) "A Simple and Inexpensive System to Amplify DNA by PCR," BioTechniques 7 (6): 566–567.
Changelian, Paul S. et al. (1989) "Structure of the NGFI–A gene and detection of upstream sequences responsible for its transcriptional induction by nerve growth factor," Proc. Natl. Acad. Sci. USA 86: 377–381 (Exhibit 3).

(List continued on next page.)

Primary Examiner—Terry McKelvey
(74) Attorney, Agent, or Firm—John P. White; Cooper & Dunham LLP

(57) ABSTRACT

The present invention provides a method of transcriptionally modulating the expression of a gene of interest, the expression of which is associated with a defined physiological or pathological effect within a multicellular organism. The method comprises contacting a cell which is capable of expressing the gene with an amount of a molecule effective to transcriptionally modulate expression of the gene and thereby affect the level of the protein encoded by the gene which is expressed by the cell. Molecules useful in the practice of the invention are characterized as follows (a) do not naturally occur in the cell, (b) specifically transcriptionally modulate expression of the gene of interest, and (c) bind to DNA or RNA or bind to a protein through a domain of such protein which is not a ligand binding domain of a receptor which naturally occurs in the cell, the binding of a ligand to which ligand binding domain is normally associated with the defined physiological or pathological effect.

26 Claims, 48 Drawing Sheets

OTHER PUBLICATIONS

Chen, William S. et al. (1987) "Requirement for intrinisic protein tyrosine kinase in the immediate and late actions of the EGF receptor," Nature 328: 820–823 (Exhibit 4).

Comb M. et al. (1986) "A Cyclic AMP–and Phorbol Ester–Inducible DNA Element," Nature 323: 353–356.

Connelly, C. et al., (1989) "The Role of Transgenic Animals in the Analysis of Various Biological Aspects of Normal and Pathologic States," Experimental Cell Research 183: 257–276.

Cybulsky, M. et al., (1991) "Gene Structure, Chromosomal Location, and Basis for Alternative mRNA Splicing of the Human VCAM1 Gene," Proc. Natl. Acad. Sci. USA 88: 7859–7863.

Das, H. et al., (1988) "Cell Type–Specific Expression of the Human ApoB Gene Is Controlled by Two Cis–Acting Regulatory Regions," Journal of Biological Chemistry 263 (23): 11452–11458.

Day, Richard N. et al. (1989) "A Protein Kinase Inhibitor Gene Reduces Both Basal and Multihormone–stimulated Prolactin Gene Transcription," J. Biol. Chem. 264(1): 431–436 (Exhibit 5).

de Wet et al., (1987) "Firefly Luciferase Gene: Structure and Expression in Mammalian Cells," Molecular and Cellular Biology 7(2): 725–737.

Doppler, Wolfgang et al. (1989) "Prolacting and glucocorticoid hormones synergistically induce expression of transfected rat β–casein gene promoter constructs in a mammary epithelial cell line," Proc. Natl. Acad. Sci. USA 86: 104–108(Exhibit 6).

Emmel, E. et al., (1989) "Cyclosporin A Specifically Inhibits Function of Nuclear Proteins Involved in T Cell Activation," Science 246: 1617–1620.

Engebrecht, J. et al., (1985) "Measuring Gene Expression with Light," Science 227: 1345–1347.

Frisch, Steven M. and H. Earl Ruley, (1987) "Transcription from the Stromelysin Promoter is Induced by Interleukin–1 and Repressed by Dexemthasone," J. Bio. Chem. 262(34): 16300–16304(Exhibit 7).

Giguere, et al. (Dec. 17, 1987) Nature 330: 624–629.

Godley, Juanita M. and Stephen J. Brand, (1989) "Regulation of the gastrin promoter by epidermal growth factor and neuropeptides," Proc. Natl. Acad. Sci. USA 86: 3036–3040(Exhibit 8).

Gunter, K. et al., (1989) "Cyclosporin A–Mediated Inhibition of Mitrogen–Induced Gene Transcription Is Specific for the Mitogenic Stimulus and Cell Type," Journal of Immunology 142: 3286–3291.

Hanauske, Axel–Rainer et al. "Alteration of EGF–Receptor Binding in Human Breast Cancer Cells by Antineoplastic Agents," Eur. J. Cancer Clin. Oncol. 23(5): 545–551(Exhibit 9).

Higuchi, K. et al., (1988) "Tissue–Specific Expression of Apolipoprotein A–I (ApoA–I) Is Regulated by the 5'–Flanking Region of the Human ApoA–I Gene," Journal of Biological Chemistry 263 (34): 18530–18536.

Holbrook, N. et al., (1984) "T–Cell Growth Factor: Complete Nucleotide Sequence and Organization of the Gene in Normal and Malignant Cells," Proc. Natl. Acad. Sci. USA 81: 1634–1638.

Hsu, M. et al., (1991) "Inhibition of HIV Replication in Acute and Chronic Infections in Vitro by a Tat Antagonist," Science, 254: 1799–1802.

Ishii, S. et al., (1985) "Characterization and Sequence of the Promoter Region of the Human Epidermal Growth Factor Receptor Gene,"Proc. Natl. Acad. Sci. USA 82: 4920–4924.

Kaushansky, K. et al., (1985) "Genomic Cloning, Characterization, Multilineage Growth–Promoting Activity of Human Granulocyte–Macrophage Colony–Stimulating Factor," Proc. Natl. Acad. Sci. USA 83: 3101–3105.

Kawasaki, E. et al., (1985) "Molecular Cloning of a Complementary DNA Encoding Human Macrophage–Specific Colony–Stimulating Factor (CSF–1)," Science 230: 291–296.

Knott, T. et al., (1986) "Complete Protein Sequence and Identification of Structural Domains of Human Apolipoprotein B," Nature 323: 734–738.

Kronke, M. et al., (1984) "Cyclosporin A Inhibits T–Cell Growth Factor Gene Expression at the Level of mRNA Transcription," Proc. Natl. Acad. Sci. USA 81: 5214–5218.

Ladner, M. et al., (1987) "Human CSF–1: Gene Structure and Alternative splicing of mRNA Precursors," The EMBO Journal 6 (9): 2693–2698.

Lamb, P. et al., (1986) "Characterization of the Human p53 Gene," Molecular and Cellular Biology 6 (5): 1379–1385.

Lee, M–T et al., (1990) "Differential Expression of M–CSF, and GM–CSF by Human Monocytes," Biol. Abstr. 89(10): AB–100645.

Lefevre, C. et al., (1987) "Tissue–Specific Expression of the Human Growth Hormone Gene Is Conferred in Part by the Binding of a Specific Trans–Acting Factor," The EMBO Journal 6 (4): 971–981.

Lim, K. et al., (1989) "A Simple Assay for DNA Transfection by Incubation of the Cells in Culture Dishes with Substrates for Beta–Galactosidase," BioTechniques 7 (6): 576–579.

Lin, F. et al., (1985) "Cloning and Expression of the Human Erythropoietin Gene," Proc. Natl. Acad. Sci. USA 82: 7580–7584.

Majesky, M. et al., (1990) "PDGF Ligand and Receptor Gene Expression during Repair of Arterial Injury," Journal of Cell Biology 111: 2149–2158.

Maniatis, T. et al., (1987) "Regulation of Inducible and Tissue–Specific Gene Expression," Science 236: 1237–1245.

Mayo, K. et al., (1985) "Altered Regulation of the Mouse Metallothionein–I Gene Following Gene Amplification or Transfection," (in *Gene Amplification*) Schimke, R.T. ed., 67–73.

McCall, C. et al., (1989) "Biotherapy: A New Dimension in Cancer Treatment," Bio/Technology 7: 231–240.

Metzler, D., (1977) *Biochemistry: The Chemical Reactions of Living Cells,* 116–117.

Miyajima, Ikuko et al. (1988) "Supressors of gpal Mutation Cause Sterility in Saccharomyces cerevisiae," Genetics 119: 797–804 (Exhibit 11).

Nagata, S. et al., (1986) "The Chromosomal Gene Structure and Two mRNAs for Human Granulocyte Colony–Stimulating Factor," The EMBO Journal 5 (3): 575–581.

Neuhold, S. et al. (1986) DNA, 5(5): 403–411 abstract.

Nimer, S. et al., (1988) "Serum Cholesterol–Lowering Activity of Granulocyte–Macrophage Colony–Stimulating Factor," JAMA 260 (22): 3297–3300.

Nishizuka, Y., (1986) "Studies and Perspectives of Protein Kinase C," Science 233: 305–312.

Paul, W. (1984) *Fundamental Immunology,* 275–276.

Pons, M. et al., (1990) "A New Cellular Model of Response to Estrogens: A Bioluminescent Test to Characterize (Anti) Estrogen Molecules," BioTechniques 9 (4): 450–459.

Prager, Diane and Shlomo Melmed, (1988) "Insuling Regulates Expression of the Human Growth Hormone Gene in Transfected Cells," J. Biol. Chem. 263(32): 16580–16585 (Exhibit 12).

Rao, A. et al., (1990) "A Quantitative Assay for β–D–Glucuronidase (GUS) Using Microtiter Plates," BioTechniques 8 (1): 38–40.

Ratner, M., (1989) "Can the Antisense Message Be Delivered?," Bio/Technology 7: 207.

Ray, Anuradha et al. (1988) "Activation of the human β2–interferon/hepatocyte–stimulating factor/interleukin 6'promoter by cytokines, viruses, and second messenger agonists," Proc. Natl. Acad. Sci. USA 85: 6701–6705 (Exhibit 13).

Rinkus, S. et al., (1980) "The Need for Both in Vitro and in Vivo Systems in Mutagenicity Screening," in *Chemical Mutagens,* de Serres et al. ed., 6: 365–473.

Roesler, W. et al., (1988) "Cyclic AMP and the Induction of Eukaryotic Gene Transcription," Journal of Biological Chemistry 263 (19): 9063–9066.

Sambrook, J. et al., (1989) "Strategies for Studying Gene Regulation," Molecular Cloning: A Laboratory Manual, 2nd Ed., 16.56–16.58.

Seguin, C. et al., (1987) "Regulation in Vitro of Metallothionein Gene Binding Factors," Science 235: 1383–1387.

Singleton, P. et al., (1987) Dictionary of Microbiology and Molecular Biology, p. 314 and p. 382.

Slack, J. et al., (1989) "Application of the Multiscreen System to Cytokine Radioreceptor Assays," BioTechniques 7 (10): 1132–1138.

Standaert, R. et al., (1990) "Molecular Cloning and Overexpression of the Human FK506–Binding Protein FKBP," Nature 346: 671–674.

Stanley, E. et al., (1985) "The Structure and Expression of the Murine Gene Encoding Granulocyte–Macrophage Colony Stimulating Factor: Evidence for Utilisation of Alternative Promoters," The EMBO Journal 4 (10): 2569–2573.

Stumpo, Deborah J., (1988) "Identification of c–fos Sequences Involved in Induction by Insulin and Phorbol Esters," J. Biol. Chem. 263(4): 1611–1614 (Exhibit 14).

Tal, M. et al., (1987) "Human HER2 (neu) Promoter: Evidence of Multiple Mechanisms for Transcriptional Initiation," Molecular and Cellular Biology 7 (7): 2597–2601.

Tamura, R. et al., (1988) "Effect of Pyrimidine Deoxynucleosides and Sodium Butyrate on Expression of the Glycoprotein Hormone α–Subunit and Placental Alkaline Phosphatase in HeLa Cells," Chemical Abstracts 108(15): AB–124167.

Tischer, E. et al., (1991) "The Human Gene for Vascular Endothelial Growth Factor," Journal of Biological Chemistry 266 (18): 11947–11954.

Tocci, M. et al. "The Immunosuppressant FK506 Selectively Inhibits Expression of Early T Cell Activation Genes," Journal of Immunology 143 (2): 718–726.

Van Arsdell, Scott W. et al. (1987) "The Yeast Repeated Element Sigma Contains a Hormone–Inducible Promoter," Molecular and Cellular Biology 7: 749–759 (Exhibit 15).

Vellenga, E. et al. (1988) "Independent Regulation of M–CSF and G–CSF Gene Expression in Human Monocytes," Blood 71 (6): 1529–1532.

Visvader, Jane et al. (1988) Two adjacent promoter elements mediate nerve growth factor activation of the c–fos gene and bind distinct nuclear complexes, Proc. Natl. Acad. Sci. USA 85: 9474–9478 (Exhibit 16).

Willingham, M. et al., (1990) "A Reversible Multi–Well Chamber for Incubation of Cultured Cells with Small Volumes: Application to Screening of Hybridoma Fusions Using Immunofluorescence Microscopy," BioTechniques 8 (3): 320–324.

Wu, K. et al. "Aspirin Inhibits Interleukin 1–Induced Prostaglandin H Synthase Expression in Cultured Endothelial Cells," Proc. Natl. Acad. Sci. USA 88: 2384–2397.

Yang, Y. et al. (1986) "Human IL–3 (Multi–CSF): Identification by Expression Cloning of a Novel Hematopoietic Growth Factor Related to Muring IL–3," Cell 47: 3–10.

* cited by examiner pUV 102 with inserted TK-NEO cassette

FIGURE 11A

SEQUENCE OF THE pUV OLIGONUCLEOTIDES pUV1:
5'TCGACCCGGGGGCCGCTGATCAGACGTCGGCCGGTACCGTGCACTACGTAAGATCTAA GCTT3' pUV2:
5'ACTAGTCTGCAGGCTAGCACTCTTCTGGTCCCCACAGACTCAGAGAGAACCCACCATGGA 3' pUV3:
5'AGACGCCAAAAACATCAAGAAAGGCCCGGCCATTCTATCCTCTAGAGGGGATCCAGC TG3' pUV4:
5'TAGATCTTACGTAGTGCACGGTACCGGCCGACGTCTGATCAGCGGCCCCCGGG3' pUV5:
5'GGTGGGTTCTCTCTGAGTCTGTGGGGACCAGAAGAGTGCTAGCCTGCGACTAGTAAGCT3' pUV6:
5'AATTCAGCTGGATCCCCTCTAGAGGATAGAATGGCCGGGCCTTTCTTGATGTTTTTGGCGT CTTCCAT3'

CONSTRUCTION OF pUV 001

CONSTRUCTION OF pUV100

FIGURE 15      SYNTHETIC HSV-TK PROMOTER

Oligo #1: 5'- AGCTTGGCCCCTAGGGCCACTAGTCTGCAGCTATGATGACACAA
ACCCCGCCCAGCGTCTTGTCATTGGCGA-3'

Oligo #2: 3'- ACCGGGGATCCCGGTGATCAGACTCGATACTACTGTGTTTGGGG
CGGGTCGCAGAACAGTAACCGCTTAAGCT-5'

Oligo #3: 5'- ATTCGAACACGCAGATGCAGTCGGGGGCGCGGTCCGAGGTC
CACTTCGCATATTAAGGTGACGCGTGTGGG-3'

Oligo #4: 3'- TGTGCGTCTACGTCAGCCCCCGCGCCAGGCTCCAGGTGAAG
CGTATAATTCCACTGCGCACACCCCGATC-5'

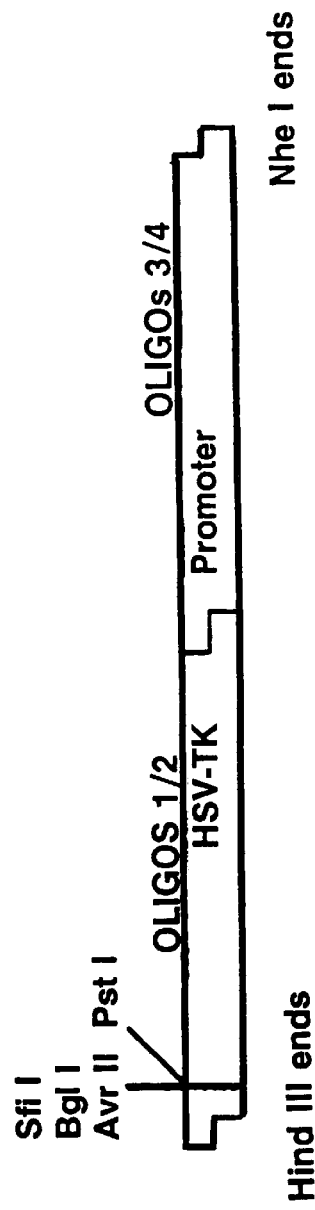

CONSTRUCTION OF pTKNEO

CONSTRUCTION OF pTKNEO3

Structure of the GM-CSF Clone

Key

S = Sal I
H = Hind III
E = Eco RI
B = Bst EII
R = Rsa I
↱ = start of transaction

FIGURE 21

Synthetic Oligo for GM-CSF/Luciferase ATG Fusion

Eco RI ends  Bst E II

OLIGO 1: 5'- AATTCGGTCACCATTAATCATTTCCTCTGTGTATTTAAGAGCTCTTTTGCCAGTGAGCCCAGTACACAG -3'

OLIGO 2:            3'- GCCAGTGGTAATTAGTAAAGGAGACACATAAATTCTCGAGAAAACGGTCACTCGGGTCATGTGTCTCTCTTTCCG -5'

ATG                                            Xba I ends

OLIGO 3: 5'- AGAGAAAGGCTAAAGTTCTCTGGAGGATGGAAGAGACGCCAAAAACATCAAGAAAAGGCCCGGCGCCATTCTATCCT -3'

OLIGO 4:    3'- ATTTCAAGAGACCTCCTACCTTCTGCGGTTTTTGTAGTTCTTTCCGGGCCGCGGGTAAGATAGGAGATC -5'

```
                    ATG      OLIGOS 3/4
                     |_____
                     |     LUCIFERASE    |___
                 ____|                       |
                |                            | Xba I ends
    OLIGOS 1/2  |
      _____|
     |  GM-CSF  |
 ____|          |
|               |
| Bst E II
|
Eco RI ends
```

FIGURE 22
Construction of pGMLS102 and pGMLS103
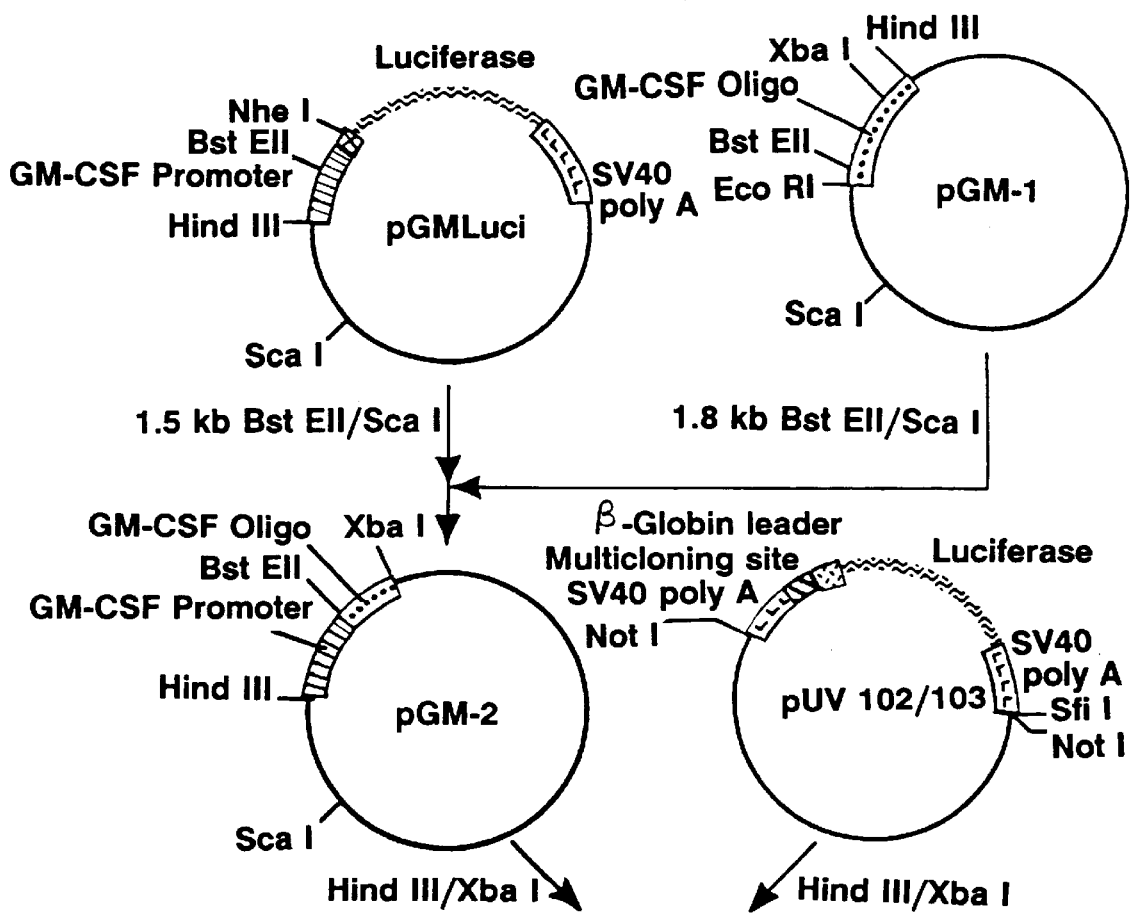
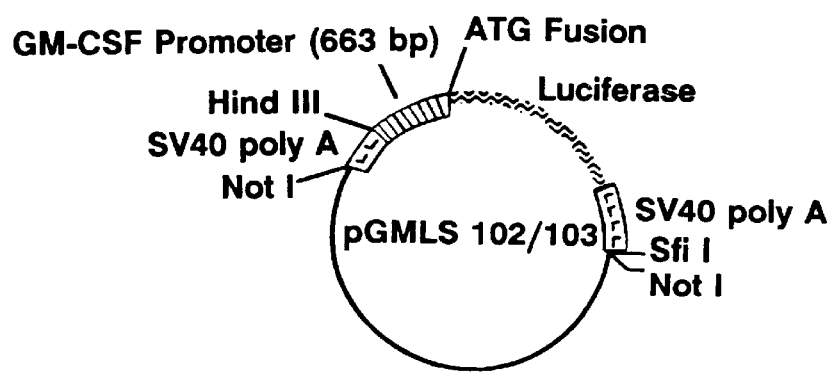

FIGURE 23  Construction of pGMLL102 and pGMLL103

Construction of CSF1-pTZ18

Construction of p100-RH

Construction of pCSF1-102

Construction of pGUV-140

Construction of pGUV 150

Construction of pEP- 7.5B

CONSTRUCTION OF pRE

Construction of IL-3-pTZ 18R

Construction of pUV-IL-3

EXAMPLES OF PRIMARY SCREEN LEAD CHEMICALS
SPECIFIC TRANSCRIPTIONAL INDUCERS

EXAMPLES OF PRIMARY SCREEN LEAD CHEMICALS SPECIFIC TRANSCRIPTIONAL INHIBITORS

METHODS OF PREPARING COMPOSITIONS COMPRISING CHEMICALS CAPABLE OF TRANSCRIPTIONAL MODULATORS

This application is a divisional of U.S. Ser. No. 08/306,925, filed Sep. 15, 1994, now abandoned, which is a continuation of U.S. Ser. No. 08/026,270, filed Mar. 4, 1993, now abandoned, which is a continuation of U.S. Ser. No. 07/382,711, filed Jul. 18, 1989, now abandoned.

BACKGROUND OF THE INVENTION

Throughout this application, various publications are referenced by Arabic numerals within parentheses. Full citations for these publications may be found at the end of the specification immediately preceding the claims. The disclosures of these publications in their entireties are hereby incorporated by reference into this application in order to more fully describe the state of the art as known to those skilled therein as of the date of the invention described and claimed herein.

The expression of a specific gene can be regulated at any step in the process of producing an active protein. Modulation of total protein activity may occur via transcriptional, transcript-processing, translational or post-translational mechanisms. Transcription may be modulated by altering the rate of transcriptional initiation or the progression of RNA polymerase (28). Transcript-processing may be influenced by circumstances such as the pattern of RNA splicing, the rate of mRNA transport to the cytoplasm or mRNA stability. This invention concerns the use of molecules which act by modulating the in vivo concentration of their target proteins via regulating gene transcription. The functional properties of these chemicals are distinct from previously described molecules which also affect gene transcription.

Researchers have documented the regulation of transcription in bacteria by low molecular weight chemicals (42, 36). Extracellular xenobiotics, amino acids and sugars have been reported to interact directly with an intracellular proteinaceous transcriptional activator or repressor to affect the transcription of specific genes.

Transcriptional regulation is sufficiently different between procaryotic and eucaryotic organisms so that a direct comparison cannot readily be made. Procaryotic cells lack a distinct membrane bound nuclear compartment. The structure and organization of procaryotic DNA elements responsible for initiation of transcription differ markedly from those of eucaryotic cells.

The eucaryotic transcriptional unit is much more complex than its procaryotic counterpart and consists of additional elements which are not found in bacteria. Eucaryotic transcriptional units include enhancers and other cis-acting DNA sequences (30, 19). Procaryotic transcription factors most commonly exhibit a "helix-turn-helix" motif in the DNA binding domain of the protein (29, 37). Eucaryotic transcriptional factors frequently contain a "zinc finger" (37, 12) or a "leucine zipper" (24) in addition to sometimes possessing the "helix-turn-helix" motif (26). Furthermore, several critical mechanisms at the post-transcriptional level such as RNA splicing and polyadenylation are not found in procaryotic systems (21, 35).

In higher eucaryotes, modulation of gene transcription in response to extracellular factors can be regulated in both a temporal and tissue specific manner (22). For example, extracellular factors can exert their effects by directly or indirectly activating or inhibiting transcription factors (22, 28).

Modulators of transcription factors involved in direct regulation of gene expression have been described, and include those extracellular chemicals entering the cell passively and binding with high affinity to their receptor-transcription factors. This class of direct transcriptional modulators include steroid hormones and their analogs, thyroid hormones, retinoic acid, vitamin $D_3$ and its derivatives, and dioxins, a chemical family of polycyclic aromatic hydrocarbons (12, 38, 9).

Dioxins are molecules generally known to modulate transcription, however, dioxins bind to naturally-occurring receptors which respond normally to xenobiotic agents via transcriptionally activating the expression of cytochrome P450, part of an enzyme involved in detoxification.

The clinical use of steroid hormones, thyroid hormones, vitamin $D_3$ and their analogs demonstrates that agents which modulate gene transcription can be used for beneficial effects, although these agents can exhibit significant adverse side effects. Obviously, analogs of these agents could have similar clinical utility as their naturally occurring counterparts by binding to the same ligand binding domain of such receptors.

Indirect transcriptional regulation involves one or more signal transduction mechanisms. The regulation typically involves interaction with a receptor, the receptor being part of a multistep intracellular signaling pathway, the pathway ultimately modulating the activity of nuclear transcription factors. This class of indirect transcriptional modulators include polypeptide growth factors such as platelet-derived growth factor, epidermal growth factor, cyclic nucleotide analogs, and mitogenic tumor promoters (18, 1, 2).

It is well documented that a large number of chemicals, both organic and inorganic, e.g. metal ions, can non-specifically modulate transcription.

Researchers have used nucleotide analogs in methods to modulate transcription. The mechanism involves incorporating nucleotide analogs into nascent mRNA or non-specifically blocking mRNA synthesis. Similarly, researchers have used alkylating agents, e.g. cyclophosphamide, or intercalating agents, e.g. doxorubicin, to non-specifically inhibit transcription.

Moreover, chemical inhibitors of hydroxymethyl-glutaryl CoA reductase, e.g. lovastatin, are known to modulate transcription by indirectly increasing expression of hepatic low density lipoprotein receptors as a consequence of lowered cholesterol levels.

Signal effector type molecules such as cyclic AMP, diacylglycerol, and their analogs are known to non-specifically regulate transcription by acting as part of a multistep protein kinase cascade reaction. These signal effector type molecules bind to domains on proteins which are thus subject to normal physiological regulation by low molecular weight ligands (10, 39).

The specific use of sterol regulatory elements from the LDL receptor gene to control expression of a reporter gene has recently been documented in PCT/US88/10095. One aspect of PCT/US88/10095 deals with the use of specific sterol regulatory elements coupled to a reporter as a means to screen for drugs capable of stimulating cells to synthesize the LDL receptor. PCT/US88/10095 describes neither the concept of simultaneously screening large numbers of chemicals against multiple target genes nor the existence of transcriptional modulators which (a) do not naturally occur in the cell, (b) specifically transcriptionally modulate expression of the gene of interest, and (c) bind to DNA or RNA or bind to a protein through a domain of such protein which is not a ligand binding domain of a receptor which naturally occurs in the cell, the binding of a ligand to which ligand binding domain is normally associated with the defined physiological effect. The main focus of PCT/US88/10095 is the use of the sterol regulatory elements from the LDL receptor as a means to inhibit expression of toxic recombinant biologicals.

The use of molecules to specifically modulate transcription of a gene of interest as described herein has not previously been reported and its use will bring surprise since available literature does not propose the use of a molecule, as described, in a method to specifically modulate transcription. Instead, the available literature has reported methods which define domains of transcriptional regulating elements of a gene of interest.

Further, the practice of using a reporter gene to analyze nucleotide sequences which regulate transcription of a gene of interest is well documented. The demonstrated utility of a reporter gene is in its ability to define domains of transcriptional regulatory elements of a gene of interest. Reporter genes which express proteins, e.g. luciferase, are widely utilized in such studies. Luciferases expressed by the North American firefly, Photinus pyralis and the bacterium, Vibrio fischeri were first described as transcriptional reporters in 1985 (8, 11)

A method to define domains of transcriptional regulating elements of a gene of interest typically has also involved use of phorbol esters, cyclic nucleotide analogs, concanavalin A, or steroids, molecules which are commonly known as transcriptional modulators. However, available literature shows that researchers have not considered using a transcription screen to identify specific transcriptional modulators. Apparently, success would be unlikely in doing so, however, we have demonstrated herein that this is not the case.

There is utility in developing the method of transcriptional modulation of a gene-of-interest by using such molecule as described herein. This method will allow the development of novel pharmaceuticals and circumvent many of the problems associated with the therapeutic use of recombinant biological factors.

Problems associated with the therapeutic use of recombinant biological factors include the technical difficulties of large scale protein purification, the high costs of protein production, the limited shelf-life of most proteins and in some cases a short biological half-life of the administered protein in the organism. Additionally, therapeutic delivery of proteins normally requires injection and frequently induces an immune reaction in situations where chronic administration is required. The method described herein provides a means of up-regulating the expression of proteins, e.g. membrane receptors, which are not readily amenable to administration as injectable biologicals.

Furthermore, chemical molecules specifically regulating the activity of one member of a group of closely related proteins are difficult to produce. Molecules, structurally related at the protein level, may possess distinct regulatory elements at the DNA level which control their expression. Thus, molecules such as the chemical transcriptional modulators defined herein can provide a greater opportunity for specifically modulating the activity of structurally related proteins. One example is the ras oncogene family, where the H-, N- and K-ras proteins are highly related but wherein the three genes have distinct structures.

Finally, the molecules described herein may also serve to mimic normal physiological response mechanisms, typically involving the coordinated expression of one or more groups of functionally related genes. Therefore, determining whether a molecule can specifically transcriptionally modulate the expression of a gene of interest and the ultimate clinical use of the molecule provides a therapeutic advantage over the use of single recombinant biologicals, or drugs which bind directly to the final target protein encoded by the gene-of-interest.

SUMMARY OF THE INVENTION

The present invention provides a method of transcriptionally modulating the expression of a gene of interest, the expression of which is associated with a defined physiological or pathological effect within a multicellular organism. The method comprises contacting a cell which is capable of expressing the gene with an amount of a molecule effective to transcriptionally modulate expression of the gene and thereby affect the level of the protein encoded by the gene which is expressed by the cell.

Molecules useful in the practice of the invention are characterized as follows (a) do not naturally occur in the cell, (b) specifically transcriptionally modulate expression of the gene of interest, and (c) bind to DNA or RNA or bind to a protein through a domain of such protein which is not a ligand binding domain of a receptor which naturally occurs in the cell, the binding of a ligand to which ligand binding domain is normally associated with the defined physiological or pathological effect.

Additionally, this invention provides a method of determining whether a molecule, not previously known to be a modulator of protein biosynthesis, is capable of transcriptionally modulating the expression of a gene of interest. The method comprises contacting a sample which contains a predefined number of cells with a predetermined amount of a molecule to be tested. Each such cell comprises DNA consisting essentially of (i) a modulatable transcriptional regulatory sequence of the gene of interest, (ii) a promoter of the gene of interest, and (iii) a reporter gene which expresses a polypeptide capable of producing a detectable signal, coupled to, and under the control of, the promoter, and the contacting is carried out under conditions such that the molecule, if capable of acting as a transcriptional modulator of the gene of interest, causes a measureable detectable signal to be produced by the polypeptide expressed by the reporter gene and the amount of the signal produced may be quantitatively determined. The amount of produced signal so determined is compared with the amount of produced signal detected in the absence of any molecule being tested or upon contacting the sample with any other molecule so as to thereby identify the molecule as one which causes a change in the detectable signal produced by the polypeptide expressed by the reporter gene and thus identify the molecule as a molecule capable of transcriptionally modulating the expression of the gene of interest.

The present invention still further provides a method for transcriptionally modulating in a multicellular organism the expression of a gene of interest, the expression of which is associated with a defined physiological or pathological effect in the organism. The method comprises administering to the organism an amount of a molecule effective to transcriptionally modulate expression of the gene and thus affect the defined physiological or pathological effect. A molecule useful in the method: (a) does not naturally occur in the organism, (b) specifically transcriptionally modulates expression of the gene of interest, and (c) binds to DNA or RNA or binds to a protein through a domain of such protein which is not a ligand binding domain of a receptor which naturally occurs in the organism, the binding of a ligand to which ligand binding domain is normally associated with the defined physiological or pathological effect.

BRIEF DESCRIPTION OF THE FIGURES

FIG. 11*a* provides the nucleotide sequences of six oligonucletides, pUV-1 through pUV-6, which were annealed, ligated, and inserted into the SalI/EcoR1 sites of the plasmid pTZ18R.

FIG. 15 provides the nucleotide sequences of oligos 1–4 used for the construction of a synthetic HSV-Thymidine Kinase promoter and provides a diagrammatic representation of the HSV-TK promoter.

FIG. 21 provides the nucleotide sequence of oligonucleotides 1 through 4 and provides a diagrammatic representation of GM-CSF upstream sequences fused with the ATG of the coding region of the luciferase gene from the firefly, *Photinus pyralis*.

FIG. 22 is a diagrammatic representation of the construction of the plasmids pGMLS102 and pGMLS103 from plasmid pUV 102 and a 0.7 kb fragment from pGM-2 and from pUV 103 and a 0.7 kb fragment from pGM-2, respectively.

DETAILED DESCRIPTION OF THE INVENTION

Figure 1:
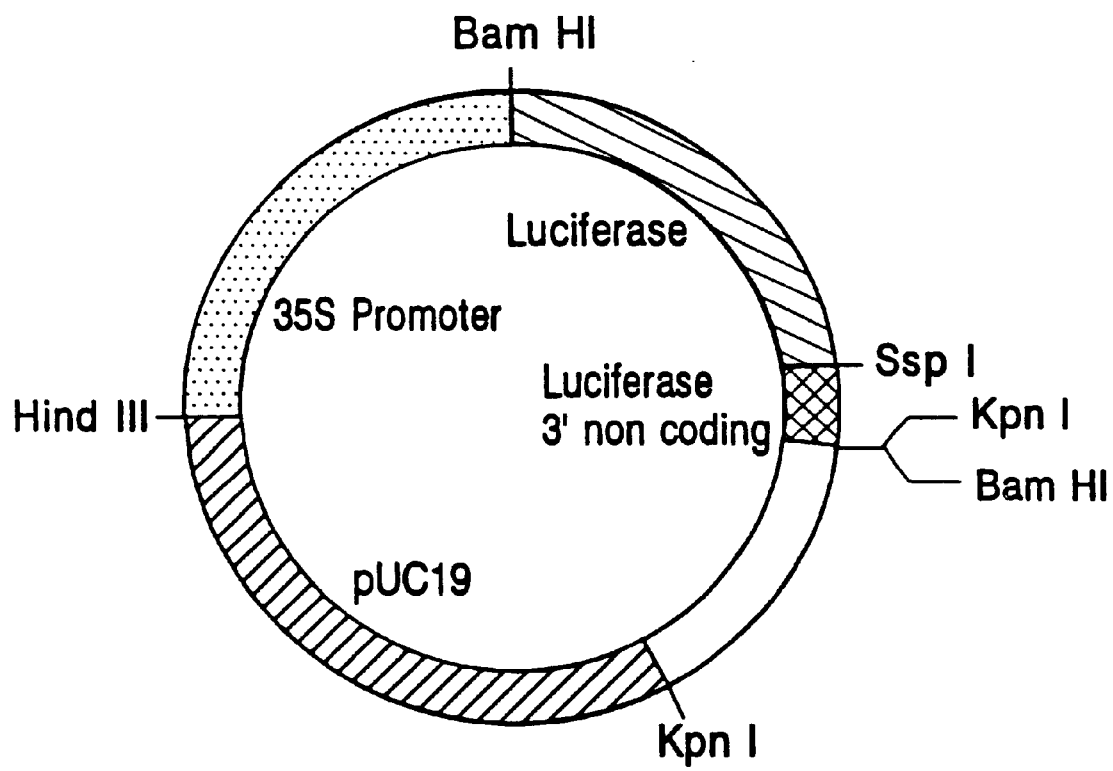
FIG. 1 is a partial restriction enzyme cleavage map of the plasmid pD0432 which contains the luciferase gene from the firefly, *Photinus pyralis*.

The present invention provides a method of transcriptionally modulating the expression of a gene of interest, the expression of which is associated with a defined physiological or pathological effect within a multicellular organism. The method comprises contacting a cell which is capable of expressing the gene with an amount of a molecule effective to transcriptionally modulate the expression of the gene. Modulating the expression of the gene affects the level of the protein encoded by the gene which is expressed by the cell.

The term "physiological effect" as used herein is defined as an effect characteristic of, or appropriate to, an organism's healthy or normal functioning. Further, the term "pathological effect" as used herein is defined as an effect altered or caused by disease.

Molecules useful in the practice of the invention are characterized as follows (a) do not naturally occur in the cell, (b) specifically transcriptionally modulate expression of the gene of interest, and (c) bind to DNA or RNA or bind to a protein through a domain of such protein which is not a ligand binding domain of a receptor which naturally occurs in the cell, the binding of a ligand to which ligand binding domain is normally associated with the defined physiological or pathological effect.

This invention, in addition to the above-described molecules, is intended to encompass the use of homologs and analogs of such molecules. In this context, homologs are molecules having substantial structural similarities to the above-described molecules and analogs are molecules having substantial biological similarities regardless of structural similarities.

The phrase "specifically transcriptionally modulate expression of the gene of interest" as used herein involves modulating the expression of the gene of interest without modulating the expression of other genes in the cell in a way which would cause an adverse effect on the organism containing the cell. However, within this definition where the drug is used to treat, for example, parasitic infection, drug application is intended to cause an adverse effect on the cells of the parasite (which may contain the gene of interest), but not on the cells of the host organism. In this context, a gene of interest may constitute a single gene or a limited number of genes whose expression can be functionally coordinated.

Moreover, the phrase "transcriptionally modulate the gene of interest" infers a notion of directness. Thus, as used herein, "transcriptionally modulate expression of a gene of interest" by a molecule means the effect upon transcription of the gene resulting from either (a) direct binding of the molecule to DNA or RNA, a DNA- or RNA-binding protein, and/or a DNA- or RNA-binding protein complex, or (b) direct binding of the molecule to a protein which directly chemically modifies a DNA- or RNA-binding protein or protein complex.

As used herein "chemically modifies" a DNA- or RNA-binding protein or protein complex means to modify the protein or protein complex through a chemical reaction, including but not limited to, phosphorylation, glycosylation, methylation, acetylation, adenoribosylation, acylation, myristylation, reduction, oxidation, covalent oligomerization or polymerization or proteolytic cleavage.

The invention provides a cell capable of expressing the gene of interest which is obtained from a multicellular organism. The cell may be a human cell, an animal cell, a plant cell or any other eucaryotic cell.

Further, in the practice of the invention, the gene of interest whose expression is associated with a defined physiological or pathological effect within a multicellular organism, may be a human gene.

Moreover, the gene of interest may encode a hematopoietic protein. Hematopoietic proteins may include, but are not limited to, colony stimulating factors and erythropoietin (EPO).

Examples of colony stimulating factors useful in the practice of this invention include, but are not limited to, granulocyte-macrophage colony stimulating factor (GM-CSF), granulocyte colony stimulating factor (G-CSF), and macrophage colony stimulating factor (M-CSF).

Further, the gene of interest of the invention may encode an interleukin (IL).

The gene of interest may also encode a growth hormone. Examples of growth hormones include, but are not limited to, human, bovine, porcine, avian, ovine, piscine, and equine growth hormones. Additionally, the gene of interest may also encode polypeptide analogs of the above-identified growth hormones.

The present invention also provides a viral gene as the gene of interest. The viral gene may be a retroviral gene. Retroviral genes of the invention may be from the HIV, HTLV-1, or HTLV-2 virus.

In the practice of the invention the viral gene may be a gene from a hepatitis virus, a herpes virus, a papilloma virus, a cytomegalovirus, or an animal virus.

Animal viruses of the invention may include, but are not limited to, pseudorabies, Marek's, Newcastle's Disease, and IBR viruses.

The gene of interest, whose expression is associated with a defined physiological or pathological effect within a multicellular organism, may also be a plant gene. The plant gene may encode an agronomically important trait. Examples of agronomically important traits may include, but are not limited to, germination, sprouting, flowering, fruit ripening, salt tolerance, herbicide resistance, pesticide resistance, fungicide resistance, temperature resistence, and growth.

Additionally, in the practice of the invention the gene of interest may be a protozoan gene. Examples of protozoans may include, but are not limited to, a selection from the group consisting of Trypanosoma, Plasmodium, Leishmania, Giardia, Entamoeba, Toxoplasma, Babesia, and Cryptosporidiosis.

Moreover, the gene of interest whose expression is associated with a defined physiological or pathological effect within a multicellular organism, may be a helminth gene.

Further, the gene of interest may also be an oncogene. Examples of oncogenes may include, but are not limited to, the phl-abl oncogene, the neu oncogene, or the src oncogene. Additionally, the oncogene may be selected from the group consisting of H-ras, N-ras, and K-ras oncogenes.

The present invention additionally provides that the gene of interest, whose expression is associated with a defined physiological or pathological effect within a multicellular organism, may encode a naturally occurring receptor. The naturally occurring receptor may be the human low density lipoprotein (LDL) receptor. Further, the receptor may be the receptor for a hemapoietic protein. Examples of hematopoietic proteins may include, but are not limited to, a selection from the group consisting of M-CSF, G-CSF, GM-CSF, and EPO.

The naturally occurring receptor encoded by the gene of interest may also be the receptor for an interleukin (IL). Examples of an IL may include, but are not limited to, a selection from the group consisting of IL-1, IL-2, IL-3, IL-4, IL-5, IL-6, IL-7 and IL-8.

Additionally, in the practice of the invention, the naturally occurring receptor may be a cell surface protein which mediates infection of the cell by a virus. Examples of viruses may include, but are not limited to, HIV, HTLV-1, HTLV-2, a hepatitis virus, a herpes virus, a papilloma virus, a cytomegalo virus and a rhinovirus.

Molecules useful for the practice of the invention bind to DNA or RNA or bind to a protein through a domain of such protein which is not a ligand binding domain of a receptor which naturally occurs in the cell, the binding of a ligand to which ligand binding domain is normally associated with the defined physiological or pathological effect. Typically, the protein to which the molecules of the invention bind is not the protein encoded by the gene of interest.

Typically, a ligand, in the context of this invention, is a molecule with a molecular weight of less than 5000 daltons, more typically less than 2,000 daltons.

This invention also provides a method of determining whether a molecule not previously known to be a modulator of protein biosynthesis is capable of transcriptionally modulating the expression of a gene of interest. The method comprises contacting a sample which contains a predefined number of cells with a predetermined amount of a molecule to be tested. Each cell comprises DNA consisting essentially of (i) a modulatable transcriptional regulatory sequence of the gene of interest, (ii) a promoter of the gene of interest, and (iii) a reporter gene which expresses a polypeptide capable of producing a detectable signal, coupled to, and under the control of, the promoter. The polypeptide expressed by the reporter gene produces the detectable signal under conditions such that the molecule, if capable of acting as a transcriptional modulator of the gene of interest, causes a measureable detectable signal to be produced by the polypeptide expressed by the reporter gene.

Quantitatively determining the amount of the signal produced requires comparing the amount of signal produced compared to the amount of produced signal detected in the absence of any molecule being tested or upon contacting the sample with any other molecule. The comparison permits the identification of the molecule as one which causes a change in the detectable signal produced by the polypeptide expressed by the reporter gene acid thus identifying the molecule as a molecule capable of transcriptionally modulating the expression of the gene of interest.

The phrase "a modulatable transcriptional regulatory sequence of a gene of interest" as used herein concerns a DNA sequence capable of regulating the initiation of transcription from the promoter of the gene of interest.

Molecules useful in the practice of this invention have the following characteristics. The molecule does not naturally occur in the cell. The molecule specifically transcriptionally modulates expression of the gene of interest. Further, the molecule binds to DNA or RNA or binds to a protein through a domain of such protein which is not a ligand binding domain of a receptor which naturally occurs in the cell. The binding of a ligand to the ligand binding domain is normally associated with the defined physiological or pathological effect.

The term "promoter" of a gene of interest is defined herein as a minimal DNA sequence necessary for specific initiation of transcription.

In the practice of the invention the sample may comprise cells in monolayers or cells in suspension. The cells of the invention may comprise human, animal, or plant cells.

Further, the invention provides that the predefined number of cells contained in the sample may be from about $5 \times 10^2$ to about $5 \times 10^5$ cells, preferably from about $10^3$ to about $5 \times 10^4$ cells.

The invention also provides that the predetermined amount of the molecule to be tested may be based on the volume of the sample. Further, the predetermined amount of the molecule to be tested may be from about 0.1 nM to about 5 mM, typically from about 0.1 $\mu$M to about 500 $\mu$M, more typically less than about 100 $\mu$M.

Further, the invention provides that contacting a sample which contains a predefined number of cells with a predetermined amount of a molecule to be tested may be effected from about 1 to about 24 hours, typically from about 2 to about 12 hours. Moreover, contacting a sample which contains a predefined number of cells with a predetermined amount of a molecule to be tested may be effected with more than one predetermined amount of the molecule to be tested. The molecule to be tested may be, but is not limited to, a purified molecule.

The modulatable transcriptional regulatory sequence in the DNA contained in the cell sample may comprise a cloned genomic regulatory sequence. Further, the modulatable transcriptional regulatory sequence may comprise less than about 100 kilobases, typically less than about 50 kilobases, preferably less than about 10 kilobases, and more preferably less than about 2 kilobases.

DNA in the cell sample may consist essentially of more than one modulatable transcriptional regulatory sequence.

The invention provides that the reporter gene in the DNA contained in the cell sample, which expresses a polypeptide capable of producing a detectable signal coupled to, and under control of, the promoter, may be inserted downstream of the endogenous promoter of the gene of interest by homologous recombination.

The invention also provides the use of a reporter gene whose product is easily detectable, a reporter gene located adjacent to, or in the vicinity of, a promoter and adjacent to, or in the vicinity of, modulatable transcriptional regulatory sequences of the gene of interest.

The reporter gene may encode a luciferase, chloramphenicol acetyltransferase, beta glucuronidase, beta galactosidase, neomycin phosphotransferase, or guanine xanthine phosphoribosyltransferase.

The present invention also provides a screening method for determining whether a molecule not previously known to be a modulator of protein biosynthesis is capable of transcriptionally modulating the expression of a gene of interest which comprises separately contacting each of a plurality of substantially identical samples, e.g. more than about $10^4$ samples, preferably more than about $10^5$ samples, each of the substantially identical samples containing a predefined number of cells, with a predetermined amount of a different molecule to be tested.

The screening method also provides a quantitative testing range wherein at least about $10^3$ samples per week are contacted with different molecules.

Moreover, the invention provides a method of essentially simultaneously screening molecules to determine whether the molecules are capable of transcriptionally modulating one or more genes of interest in a panel of such genes. The method comprises essentially simultaneously screening the molecules against each of the genes of interest by separately contacting each of a plurality of substantially identical samples, each of which contains a predefined number of cells, with a predetermined amount of a different molecule to be tested.

The invention also provides a method for transcriptionally modulating in a multicellular organism, the expression of a gene of interest, the expression of which is associated with a defined physiological or pathological effect in the organism. The method comprises administering, e.g. oral administration, administration as a suppository, topical contact, intravenous, intramuscular or subcutaneous administration, to the organism an amount of a molecule effective to transcriptionally modulate expression of the gene thereby affecting the defined physiological or pathological effect. The molecule (a) does not naturally occur in the organism, (b) specifically transcriptionally modulates expression of the gene of interest, and (c) binds to DNA or RNA or binds to a protein through a domain of such protein which is not a ligand binding domain of a receptor which naturally occurs in the organism. Moreover, the binding of a ligand to the ligand binding domain is normally associated with the defined physiological or pathological effect.

In the practice of the invention, examples of a multicellular organism include, but are not limited to, a human, an animal, or a plant.

The defined pathological effect may be associated with a disorder and the modulated expression of the gene of interest may be associated with amelioration of the disorder. Further, examples of disorders include but are not limited to, a selection from the group consisting of cancer, a hematopoietic dysfunction, diabetes, tissue inflammation, atherosclerosis, viral infections, dysfunctions of memory or learning, and dysfunctions in a cholesterol or other metabolic pathway.

Additionally, the method for transcriptionally modulating in a multicellular organism the expression of a gene of interest provides that growth may be the defined physiological effect and the organism is an animal such as a cow, a pig, a bird, a fish, a sheep, or a horse.

Further, the method for transcriptionally modulating in a multicellular organism the expression of a gene of interest provides that the agronomically important trait may be the defined physiological or pathological effect.

This invention is illustrated in the Experimental Details and Results sections which follow. These sections are set forth to aid in an understanding of the invention but are not intended to, and should not be construed to, limit in any way the invention as set forth in the claims which follow.

EXPERIMENTAL DETAILS

MATERIALS AND METHODS

A. Cell Culture

All media and reagents used for routine cell culture were purchased from Gibco (Grand Island, N.Y.), Hazelton (Lenexa, Kans.), or Whittaker Mass. Biologicals (Walkersville, Md.). Fetal calf serum (FCS) was from Hyclone (Logan, Utah), and nutrients used for serum-free defined media were purchased from Sigma (St. Louis, Mo.), Boehringer Mannheim (Indianapolis, Ind.), Bachem (Torrance, Calif.) and Collaborative Research (Bedford, Mass.).

NIH/3T3 fibroblast cells (ATCC number CRL 1658) were used for transfection of plasmids containing the mouse mammary tumor virus (MMTV) promoter linked to firefly luciferase coding sequences (see below). Cells were propagated in Dulbecco's modified Eagle's medium (DMEM) obtained from Gibco, Grand Island, N.Y. and supplemented with 10% FCS. For high-throughput (HTP) screening, transfected NIH/3T3 clones were transferred to serum free defined medium consisting of Iscove's modified Eagle's medium (IMEM) and Ham's F12 medium (1:1) supplemented with growth factors, hormones and nutrients as described previously (43).

A rat pituitary cell line, designated GC, (4, 25) was used for transfection of plasmids containing the human growth hormone promoter (see below) and was maintained in DMEM and Ham's F12 medium (1:1), supplemented with 12.5% FCS. For HTP screening, transfected GC clones were transferred to serum free defined medium consisting of DMEM and Ham's F12 medium (1:1) supplemented with growth factors, hormones and nutrients as described previously (17, 5).

A human bladder carcinoma cell line (U5637, ATCC number HTB 9) was used for transfection of plasmids containing the human Granulocyte-Colony Stimulating Factor (G-CSF) promoter (see below) and was maintained in RPMI medium supplemented with 10% FCS. For HTP screening, transfected 5637 clones were transferred to a serum free defined medium identical to that used for the NIH/3T3 clones.

G418 (Geneticin, Gibco) at 0.2 mg/ml was routinely added to both serum and serum free defined media for selection and maintenance of cell lines transfected with the neomycin resistance gene.

B. Plasmid Construction and Molecular Cloning of Promoter-Reporter Fusion Constructs to be Transfected into Cells Used for a 2,000-Chemical Transcription Screen This section describes (a) the molecular cloning of the human G-CSF promoter and adjacent 5' transcriptionally modulatable regulatory sequences and (b) the making of constructs where these regulatory sequences or those of the human growth hormone (hGH) gene or those of the mouse mammary tumor virus (MMTV) long terminal repeat (LTR) control the expression of the firefly luciferase gene. These constructs were transfected into cells as described in Section E and used for a high-throughput pilot screen of 2,000 chemicals to identify chemicals acting as specific transcriptional modulators (see Section G and "Results").

Unless otherwise indicated cloning procedures were performed essentially according to Maniatis et al. (1982) (28). Oligonucleotides were synthesized by the beta-cyanoethyl phosphoramidite method according to protocols provided by the manufacturer of the DNA-synthesizer (Model 380A, Applied Biosystems (Foster City, Calif.).

1. Construction of the MMTV Promoter-Luciferase fusion plasmid (pMluci)

Figure 2:
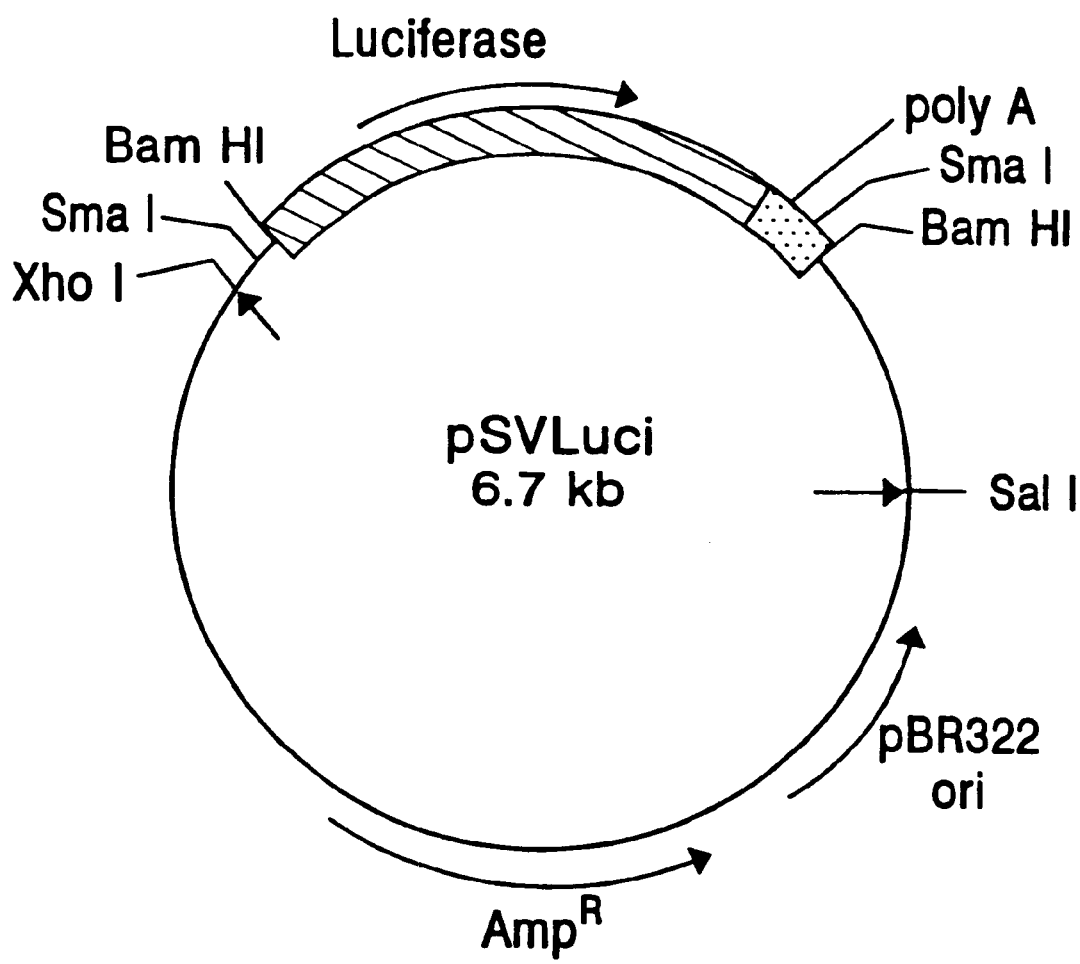
FIG. 2 is a partial restriction enzyme cleavage map of the plasmid pSVLuci which contains the luciferase gene from the firefly, *Photinus pyralis*.
Figure 3:
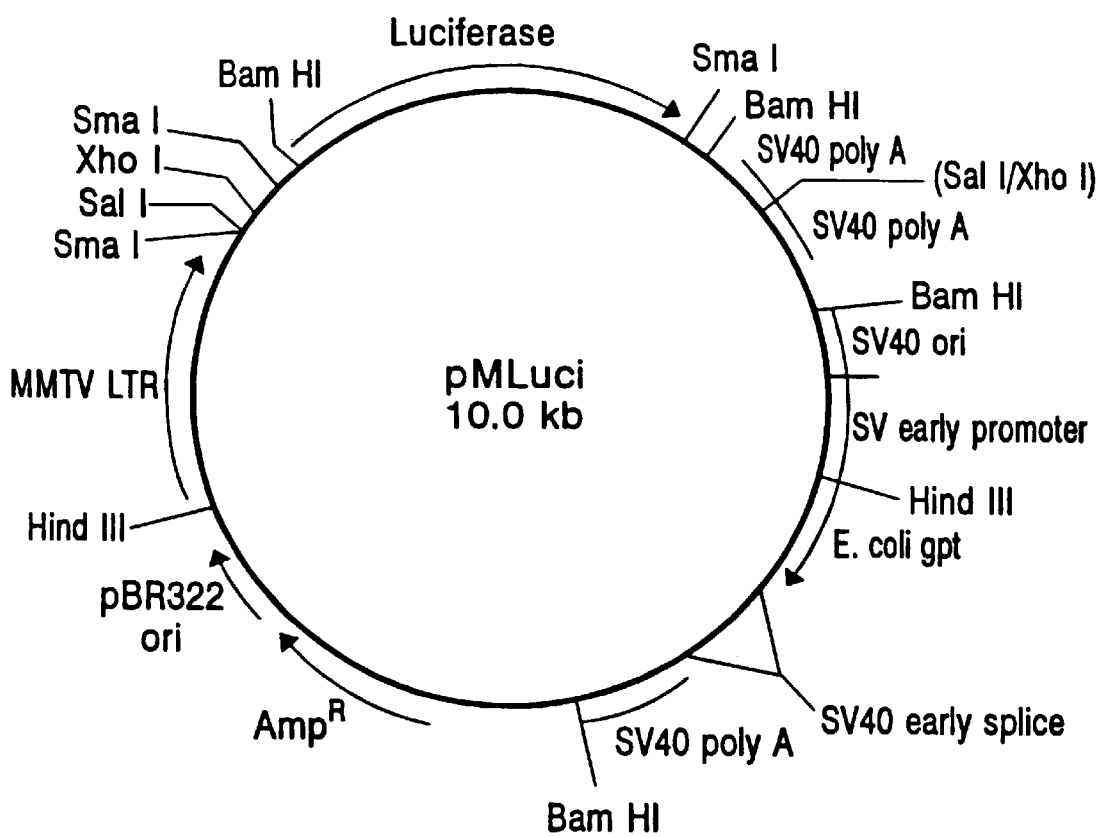
FIG. 3 is a partial restriction enzyme cleavage map of the plasmid pMLuci which contains the luciferase gene of the firefly, *Photinus pyralis* and the mouse mammary tumor virus long terminal repeat.

The firefly luciferase gene was removed from the plant expression plasmid pDO432 (33) (FIG. 1) as a 1.9 kb BamHI fragment and cloned into the BamHI site of pSVL (Pharmacia, Piscataway, N.J.), a mammalian expression vector containing the SV40 promoter. The resulting plasmid (pSVLuci; FIG. 2) was digested with XhoI and SalI to produce a 2.4 kb fragment containing the luciferase coding sequences and the SV40 late polyadenylation site. This fragment was inserted into the XhoI site of pMSG (Pharmacia, Piscataway, N.J.), a eukaryotic expression vector containing the MMTV promoter. The resulting MMTV promoter-luciferase fusion plasmid (pMLuci; FIG. 3) was used to transfect NIH/3T3 cells as described below (section E1). Similar constructs can be made using luciferase vectors from Clontech (Palo Alto, Calif.).

Figure 4:
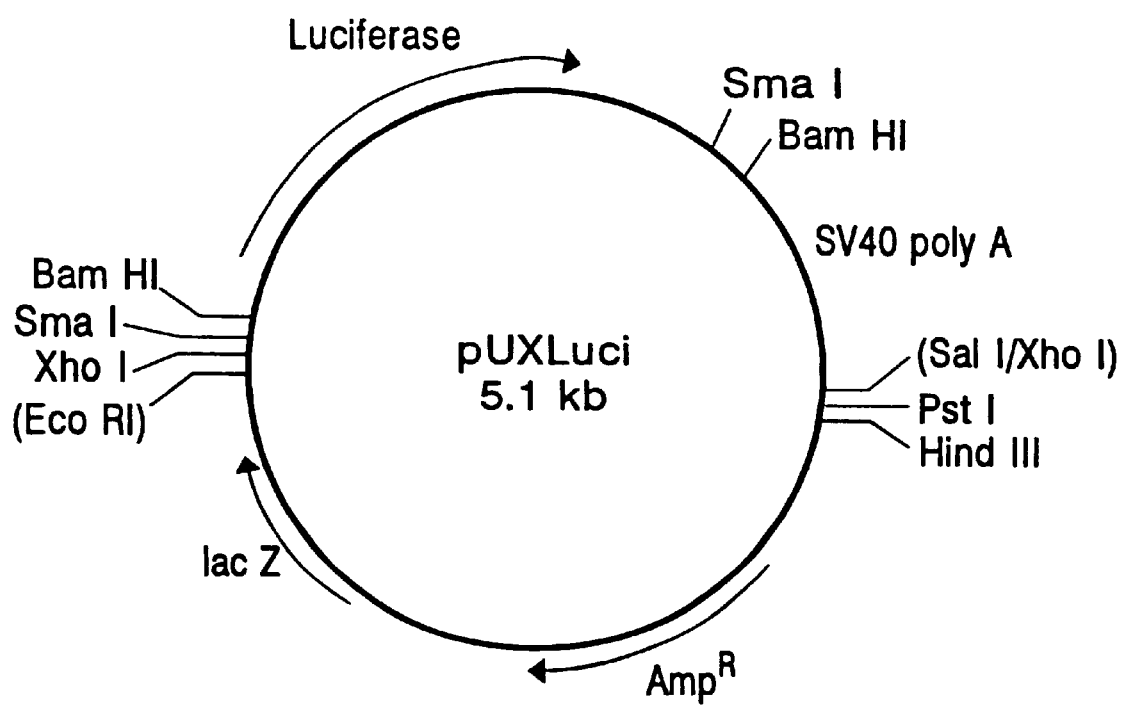
FIG. 4 is a partial restriction enzyme cleavage map of the plasmid pUXLuci which contains the luciferase gene from the firefly, *Photinus pyralis*.
Figure 5:
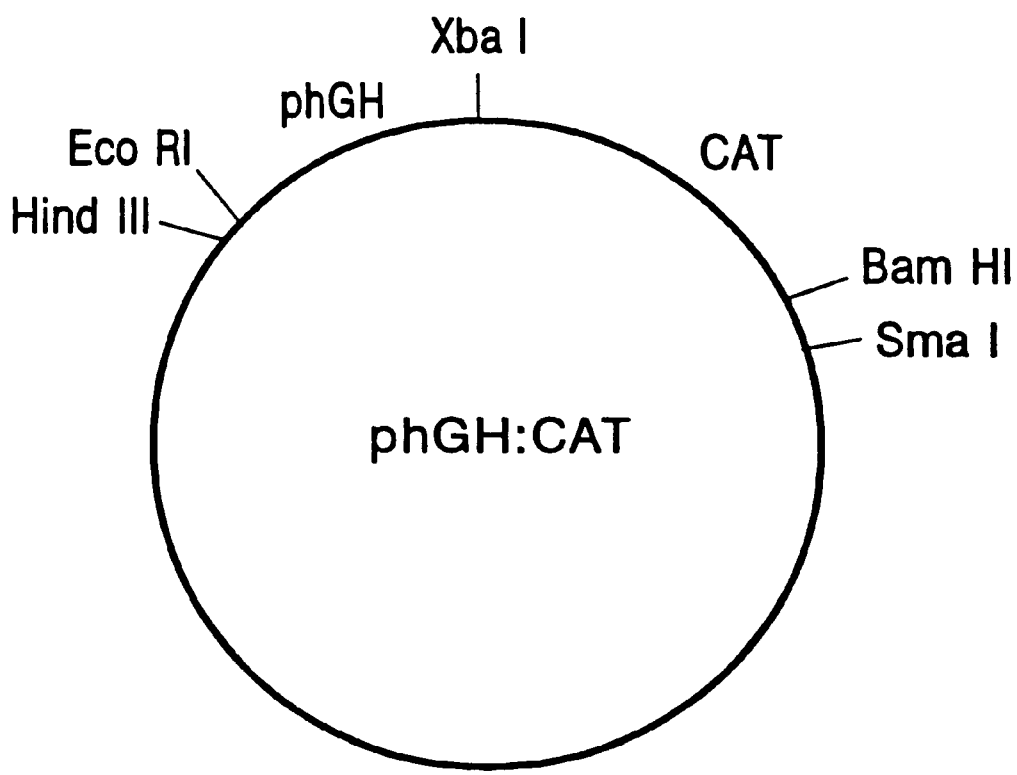
FIG. 5 is a partial restriction enzyme cleavage map of the plasmid phGH:CAT which contains the CAT gene and human growth hormone promoter sequences.
Figure 6:
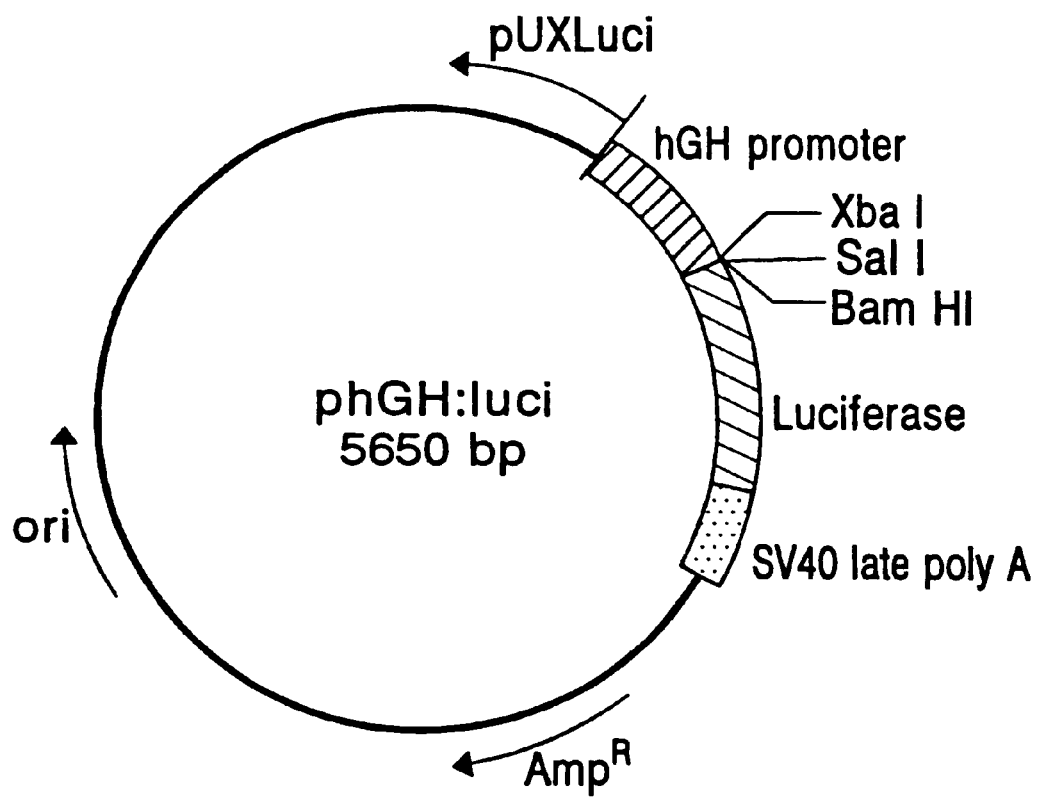
FIG. 6 is a partial restriction enzyme cleavage map of the plasmid phGH-Luci which contains the luciferase gene from the firefly, *Photinus pyralis* and human growth hormone promoter sequences.

2. Construction of the human growth hormone (hGH) promoter-luciferase fusion plasmid The SalI-XhoI fragment of pSVLuci (FIG. 2) containing the luciferase coding sequences and the SV40 late polyadenylation site was inserted into pUC 8 (Biorad, Richmond, Calif.), which had been linearized by a SmaI/HinCII digestion and ligated to XhoI linkers (New England Biolabs, Beverly, Mass.). The new plasmid thus generated (pUXLuci; FIG. 4) was linearized by XhoI digestion followed by incubation with the Klenow fragment of *E. coli* DNA polymerase and the four deoxyribonucleotides to fill in the single-stranded ends of the vector. This linear (5.1 KB) form of pUXLuci was then ligated to the filled-in 550bP HindIII-XbaI fragment of the plasmid phGH:CAT (FIG. 5) (25). Human growth hormone promoter sequences located on the HindIII-XbaI fragment were thus fused to the luciferase coding sequences located on pUXLuci generating the plasmid phGH-Luci (FIG. 6), which was used in transfections of GC cells as described below (Section E2).

3. Construction of the human Granulocyte-Colony stimulating factor (hG-CSF) Promoter-Luciferase fusion plasmid (pG-Lucl)

Figure 7:
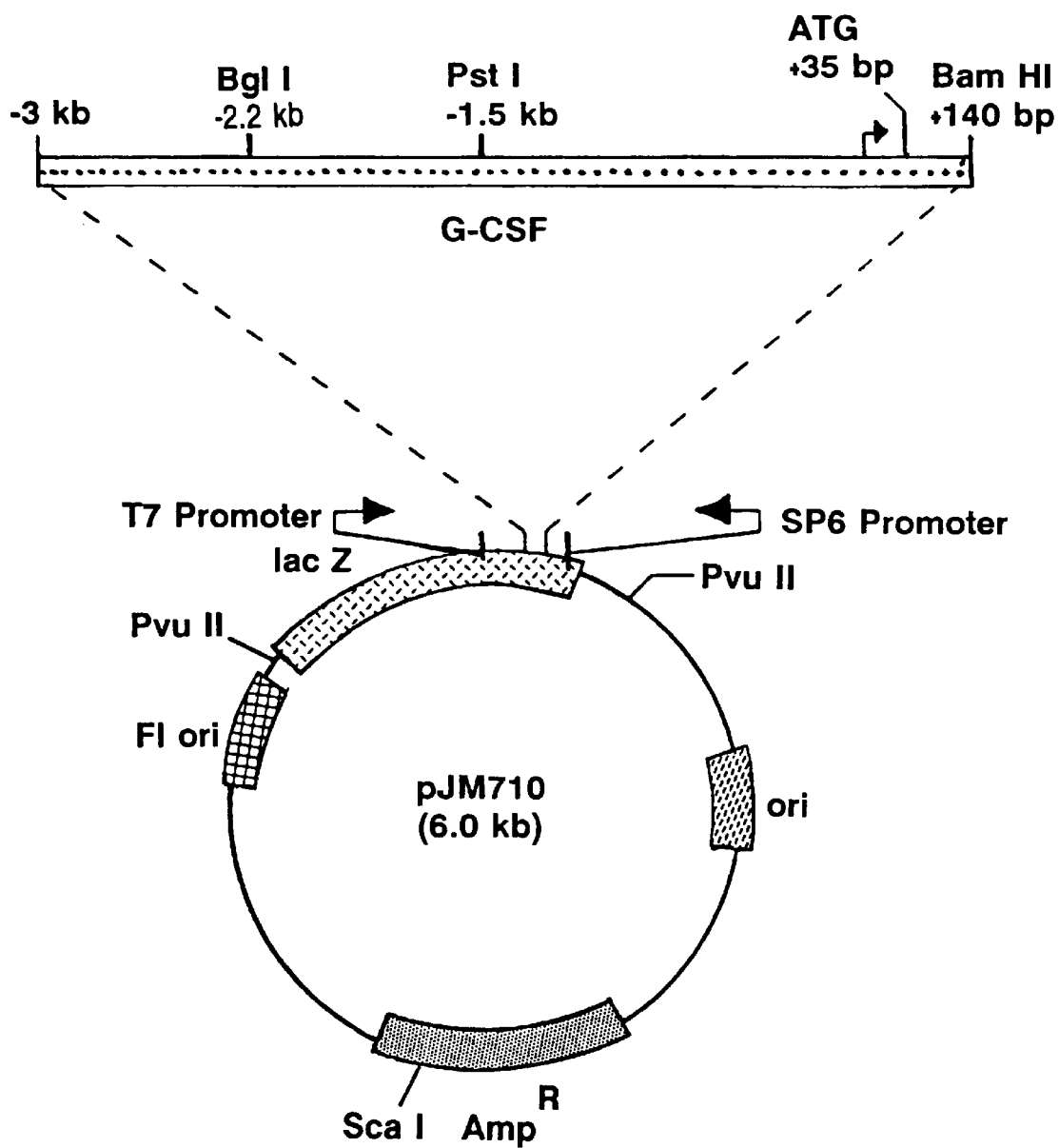
FIG. 7 is a partial restriction enzyme cleavage map of the plasmid pJM710 which contains G-CSF upstream sequences.
Figure 8:
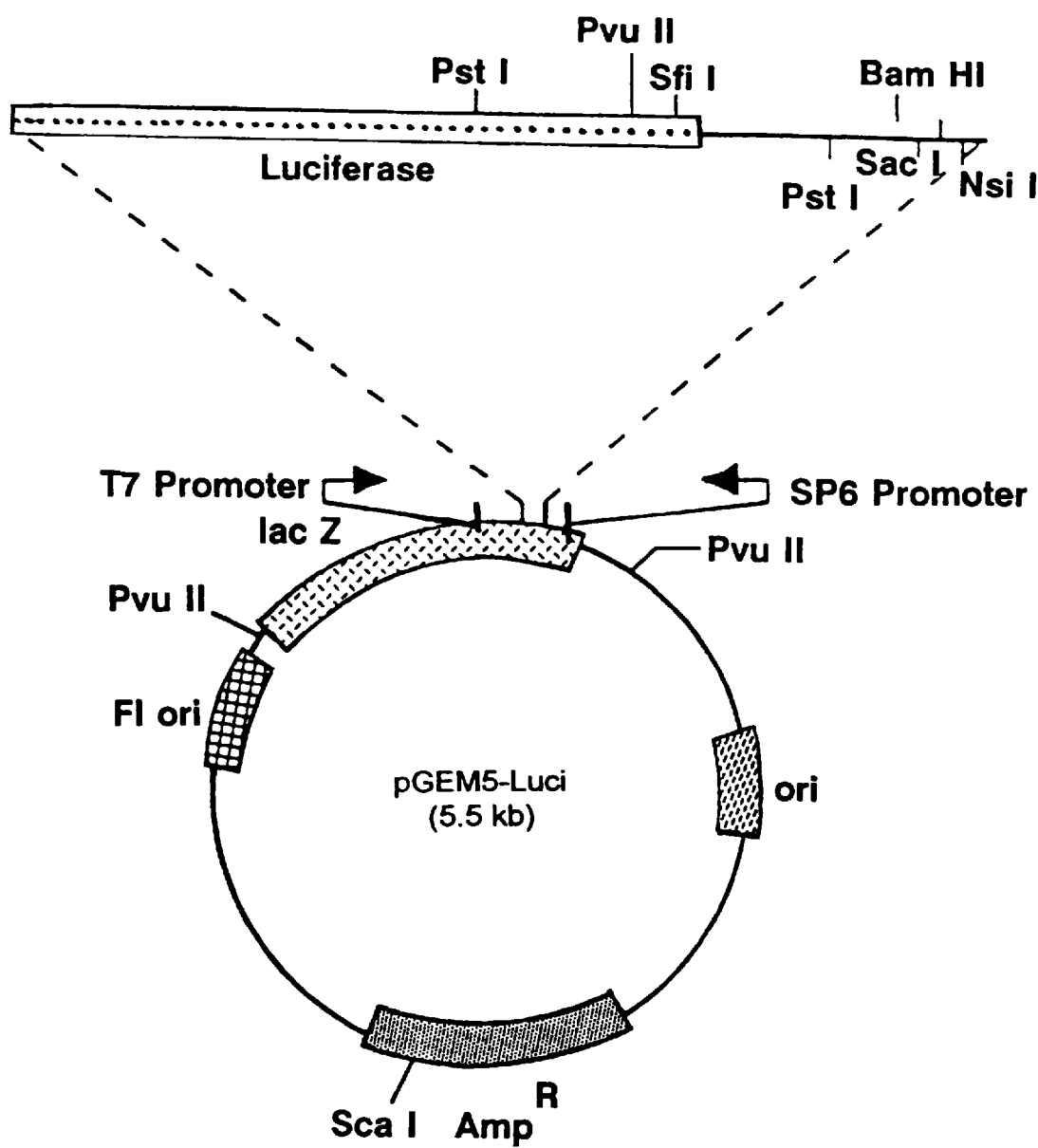
FIG. 8 is a partial restriction enzyme cleavage map of the plasmid pGEM5-Luci which contains the luciferase gene from the firefly, *Photinus pyralis*.
Figure 9:
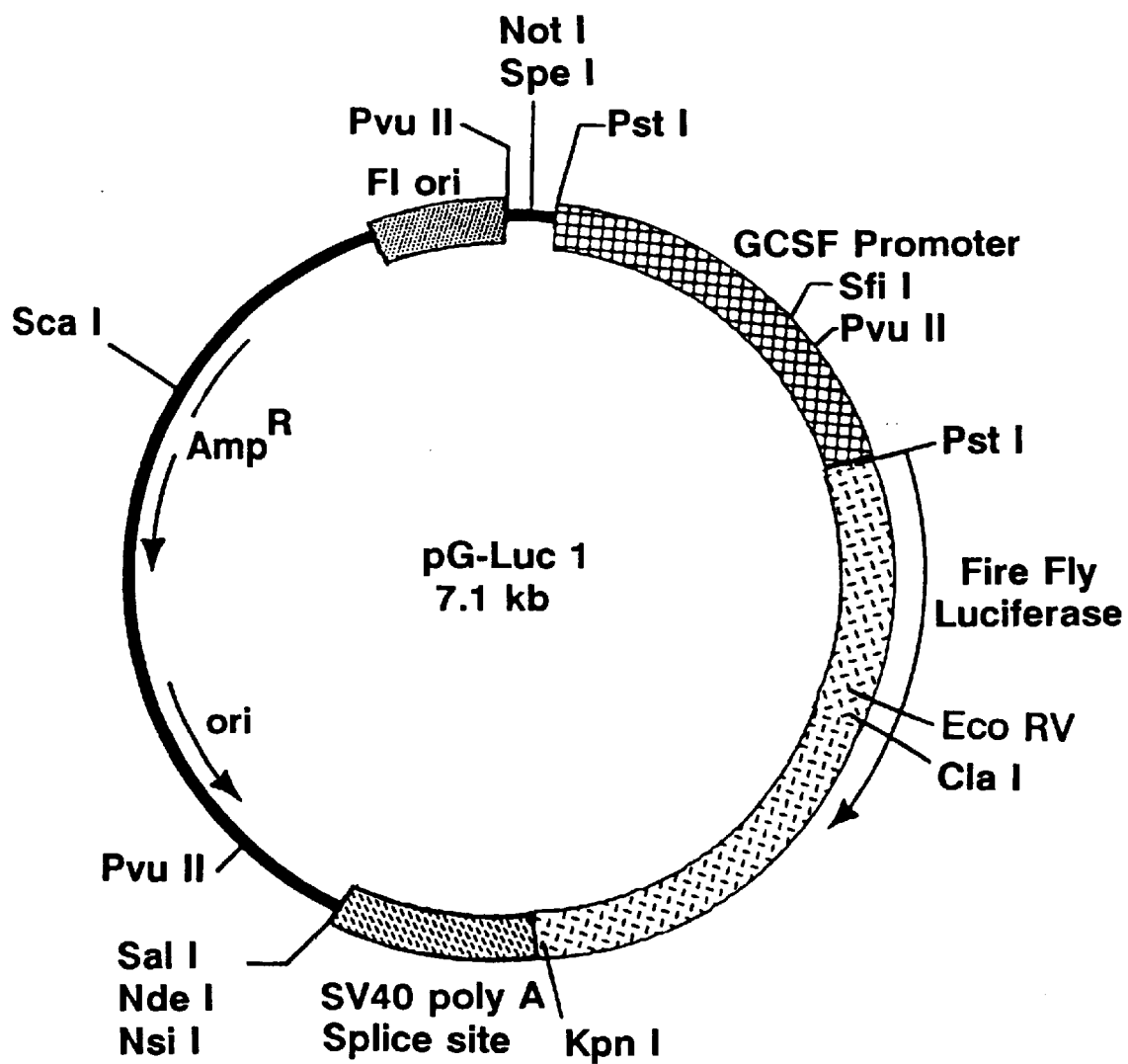
FIG. 9 is a partial restriction enzyme cleavage map of the plasmid PG-Luc 1 which contains both the luciferase gene from the firefly, *Photinus pyralis*, and G-CSF upstream sequences.

Information on the G-CSF upstream and coding sequences was published by Nagata et al. (1986) and was used to synthesize 5 oligonucleotide probes (OL-1 to OL-5) to screen a human leukocyte genomic DNA library (Clontech, Palo Alto, Calif.) according to the supplier's instructions. The sequences of the oligonucleotide probes were:

5' GCTTTTTGTTCCAACCCCCCTGCATT 3' (OL-1);

5' CCCTGCATTGTCTTGGACACCAAAT 3' (OL-2);

5' GCGCTCCAGGAGAAGCTGGTGAGT 3' (OL-3);

5' AAGCTGATGGGTGAGTGTCTTGGC 3' (OL-4);

5' ATCAGCGGCTCAGCCTTCTT 3' (OL-5);

The sequences of OL-1, OL-2 and OL-5 recognize the G-CSF promoter region, OL-4 recognizes the first intron/exon junction and OL-3 recognizes sequences within the second exon (32). One of the clones isolated from the leukocyte library using these oligonucleotide probes contains a 3.5 kb SalI-BamHI fragment of G-CSF genomic sequence consisting of 3.3 kb of promoter sequence and two hundred base pairs of the coding region. This fragment was inserted into the vector pGEM-7-Zf (Promega, Madison, Wis.) which had previously been digested with SalI/BamHI, resulting in the vector pJM710 (FIG. 7). pJM710 was then digested with PstI, and the resulting 1.6 kb fragment containing G-CSF upstream sequences and the first 15 bases of the G-CSF leader sequence was inserted into the PstI site of pGEM5-Luci (FIG. 8) to generate pG-Lucl (FIG. 9). This construct was then used for transfections of 5637 human bladder carcinoma cells as described below in section E3. pGEM5-Luci (FIG. 8) had previously been constructed by inserting the XbaI/SalI fragment from pSVLuci (FIG. 2) containing the luciferase coding sequence and the SV40 late polyadenylation signal into pGEM 5-Zf (Promega, Madison Wis.) digested with XhoI/SalI.

C. Construction of the OSI Mammalian Expression Shuttle Vector

Figure 10:
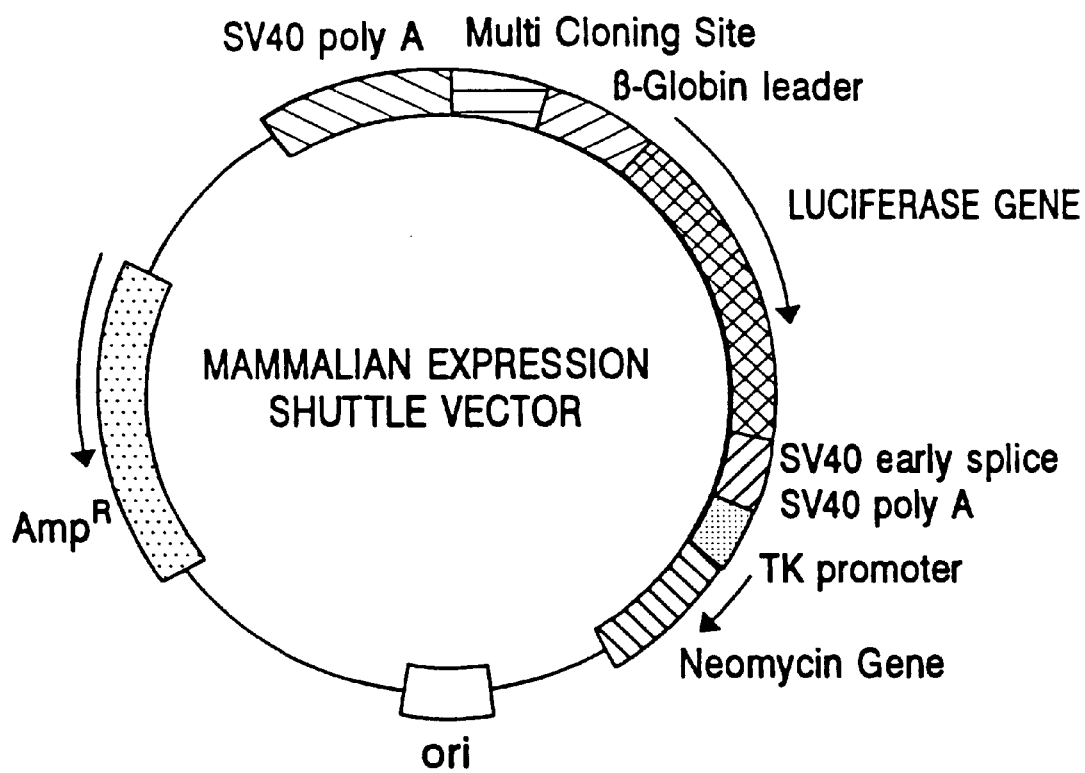
FIG. 10 is a view of the mammalian expression shuttle vector pUV102 with its features. The mammalian expression shuttle vector was designed to allow the construction of the promoter-reporter gene fusions and the insertion of a neomycin resistance gene coupled to the herpes simplex virus thymidine kinase promoter (TK-NEO).

A mammalian expression shuttle vector was designed to allow the construction of the promoter-reporter gene fusions to be used in high-throughput screens to identify transcriptionally modulating chemicals. Features of the plasmid are shown in FIG. 10. The shuttle vector was constructed in several steps. Initially six oligonucleotides (pUV-1 through pUV-6) were synthesized (see FIG. 11a for sequence). The sequences of pUV-1, pUV-2 and pUV-3 correspond to a multicloning site, the β-globin leader sequence and the first 53 bases of the firefly luciferase coding region. The sequences of pUV-4, pUV-5 and pUV-6 are complementary to the first three oligonucleotides. The pUV oligonucleotides were annealed, ligated and inserted into the SalI/EcoRI sites of pTZ18R (Pharmacia, Piscataway, N.J.) (FIG. 11(b)). The resulting vector was then digested with SmaI/PvuII and the oligonucleotide containing fragment was cloned into the bluescript KS(+) plasmid (Stratagene, La Jolla, Calif.), previously digested with PvuII, to yield pUV001 (FIG. 11(b)). Several fragments were ligated into pUV001 to create pUv100. The luciferase coding sequences (except first 53 bases) and polyadenylation site were obtained as a 1.8 kilobase XbaI/XmaI fragment from pMLuci (section B-1, FIG. 3). The SV40 early splice site and the SV40 late polyadenylation site were obtained as an 871 bp XmaI/BamHI fragment from pMSG (Pharmacia, Piscataway N.J., FIG. 12). Both DNA fragments were cloned into pUV001, previously digested with XbaI/BamHI to yield pUV100 (FIG. 12).

Figure 13:
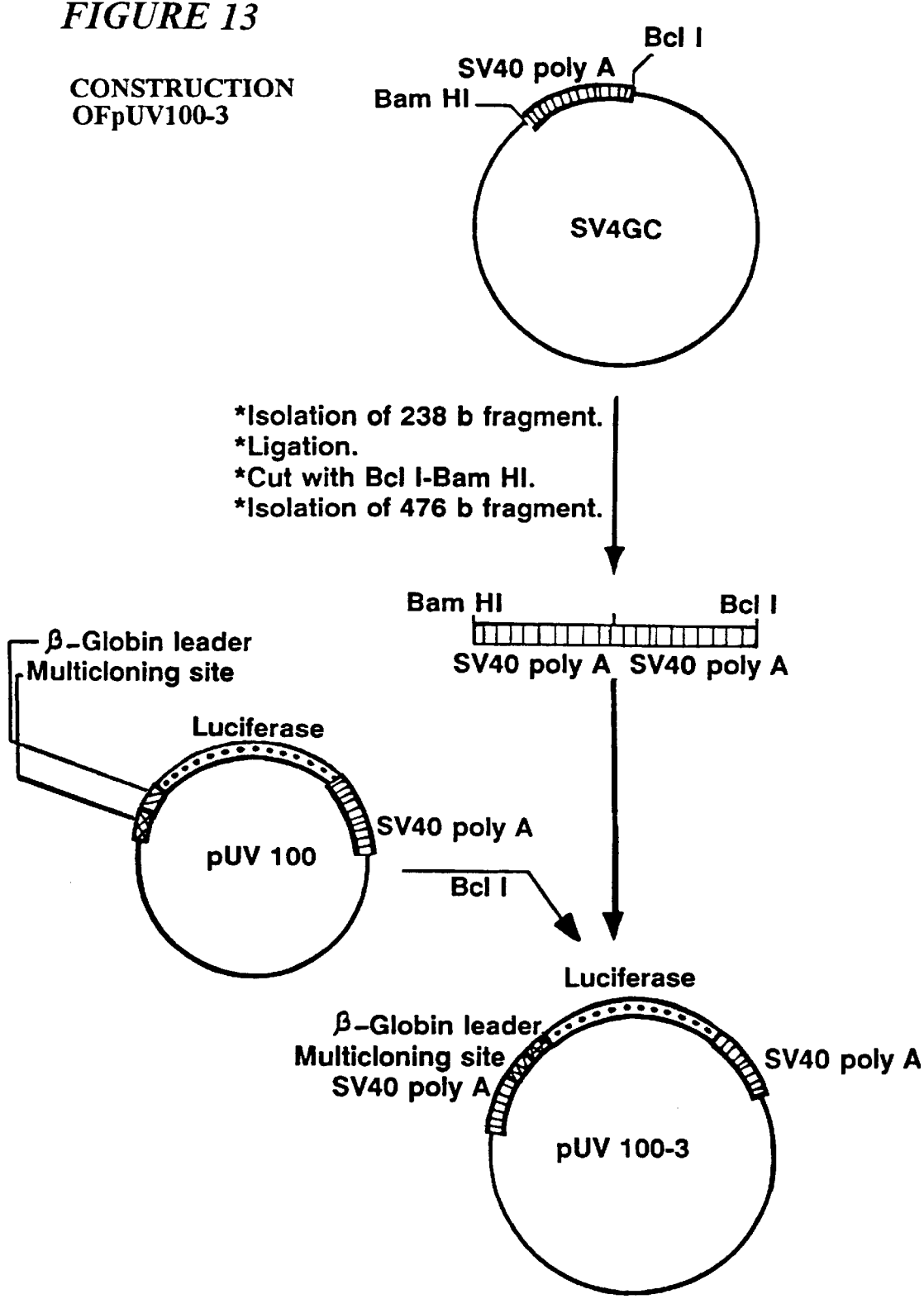
FIG. 13 is a diagrammatic representation of the construction of the plasmid pUV100-3 from the plasmid pUV100 and a 476 b fragment containing a dimeric SV40 polyadenylation site.
Figure 14:
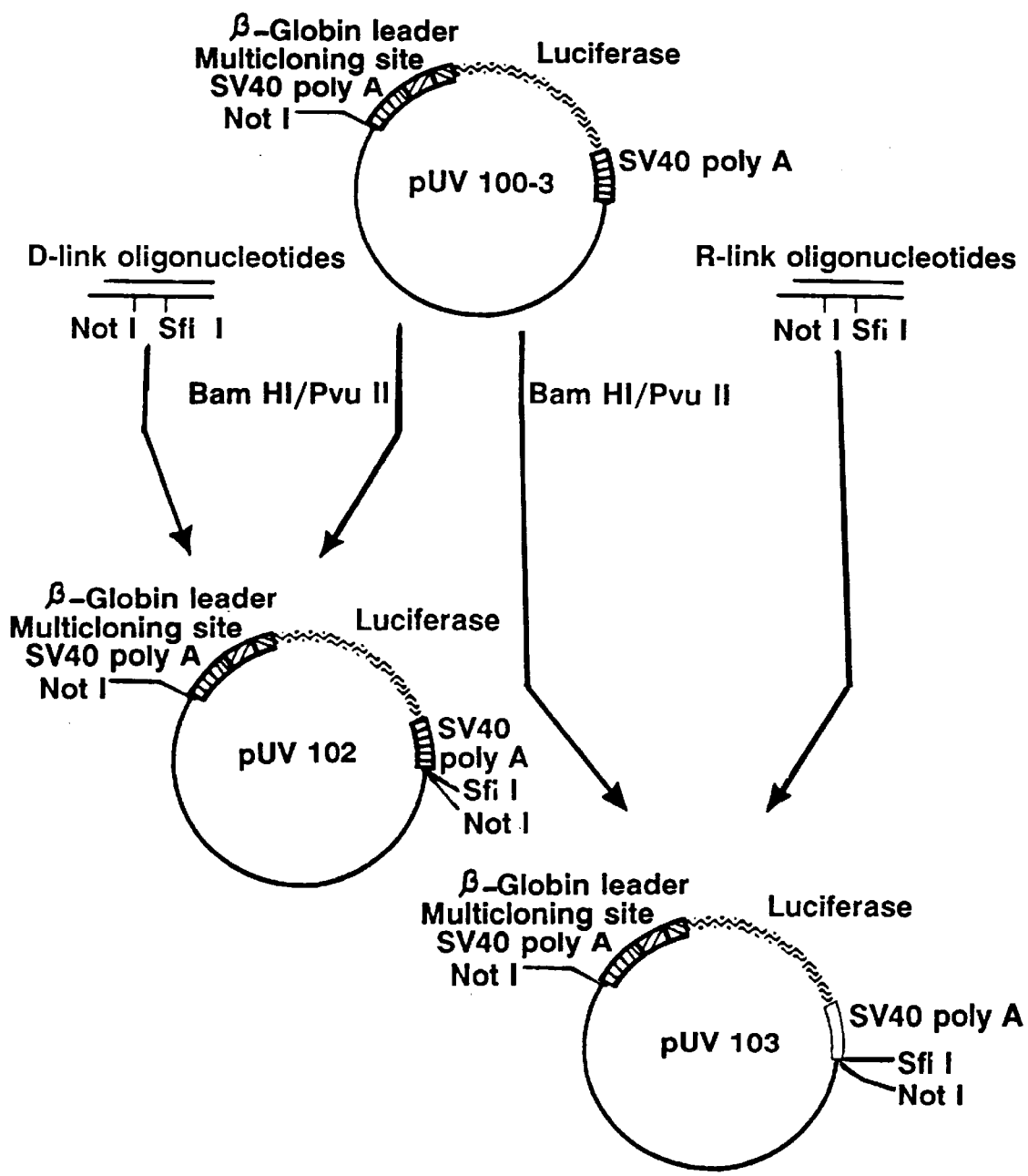
FIG. 14 is a diagrammatic representation of the construction of the plasmids pUV102 and pUV103 from the plasmid pUV100-3 and D-link oligonucleotides and the plasmid pUV100-3 and R-link oligonucleotides, respectively.

A 476 b fragment containing a dimeric SV40 polyadenylation site was then cloned into the BclI site of pUV100 (FIG. 13). To do this, a 238 bp BclI/BamHI fragment was obtained from SV40 genomic DNA (BRL), ligated, digested with BclI/BamHI, gel isolated, and inserted into pUV100, resulting in the vector pUV100-3 (FIG. 13). Linkers containing one SfiI and one NotI restriction site were then cloned into the PvuII/BamHI sites of pUV100-3. Two sets of linkers were synthesized containing the SfiI site in opposite orientations (oligonucleotides D-link1 and D-link2 and oligonucleotides R-link1 and R-link2). The sequences of the oligonucleotides were: 5' GATCGGCCCCTAGGGC-CGCGGCCGCAT 3' (D-link1) 5' ATGCGGCCGCGGC-CCTAGGGGCC 3' (D-link2) 5' GATCGGC-CCTAGGGGCGGCCGCAT 3' (R-link1) 5' ATGCGGCCGCGGCCCCCTAGGGCC 3' (R-link2)
The plasmid that contains D-link oligonucleotides was named pUV102 and the plasmid that contains R-link oligonucleotides was named pUV103 (FIG. 14).

Figure 16:
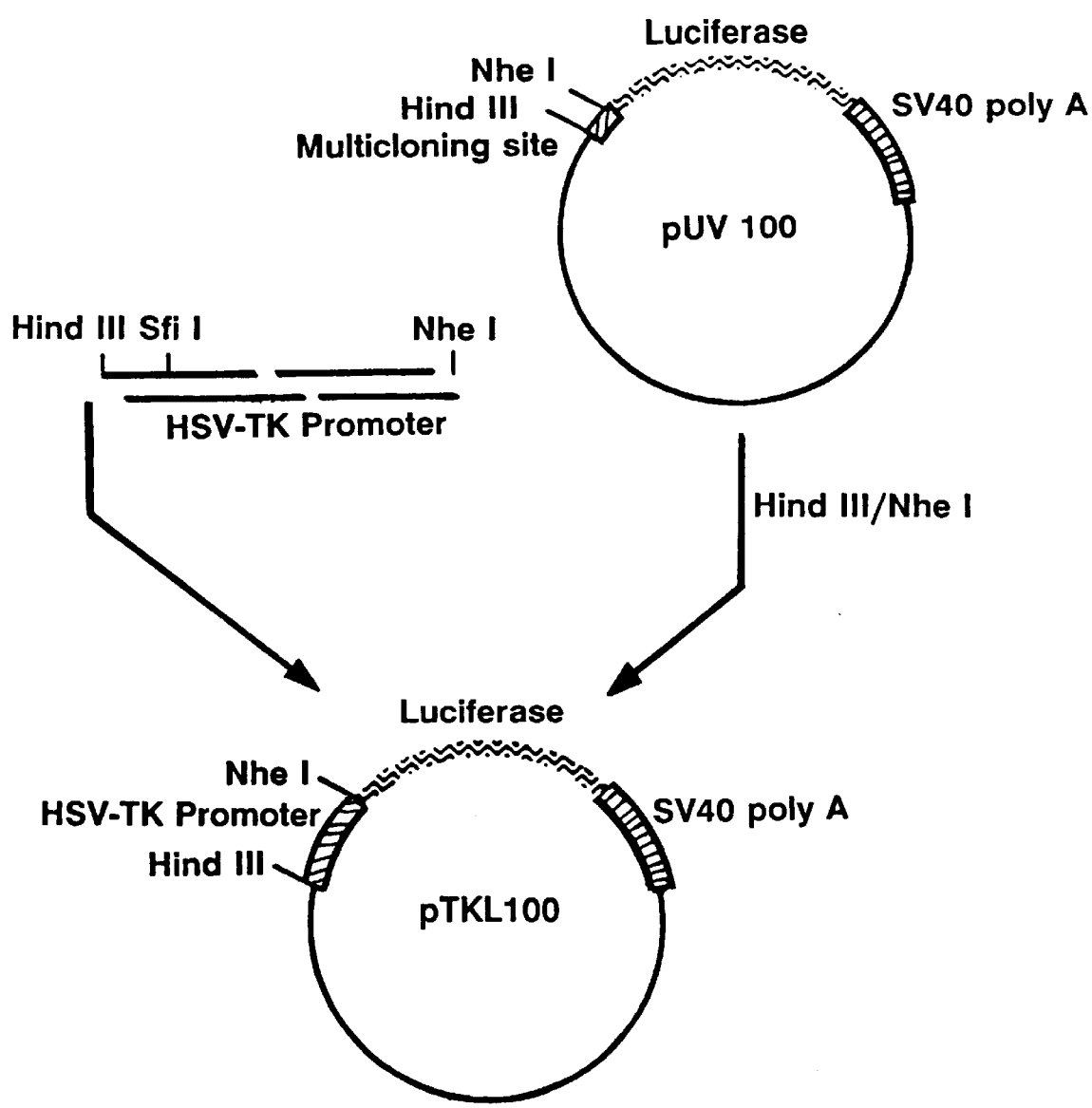
FIG. 16 is a diagrammatic representation of the construction of the plasmid pTKL100 which contains the luciferase gene from the firefly, *Photinus pyralis* and the HSV-TK promoter sequence.
Figure 17:
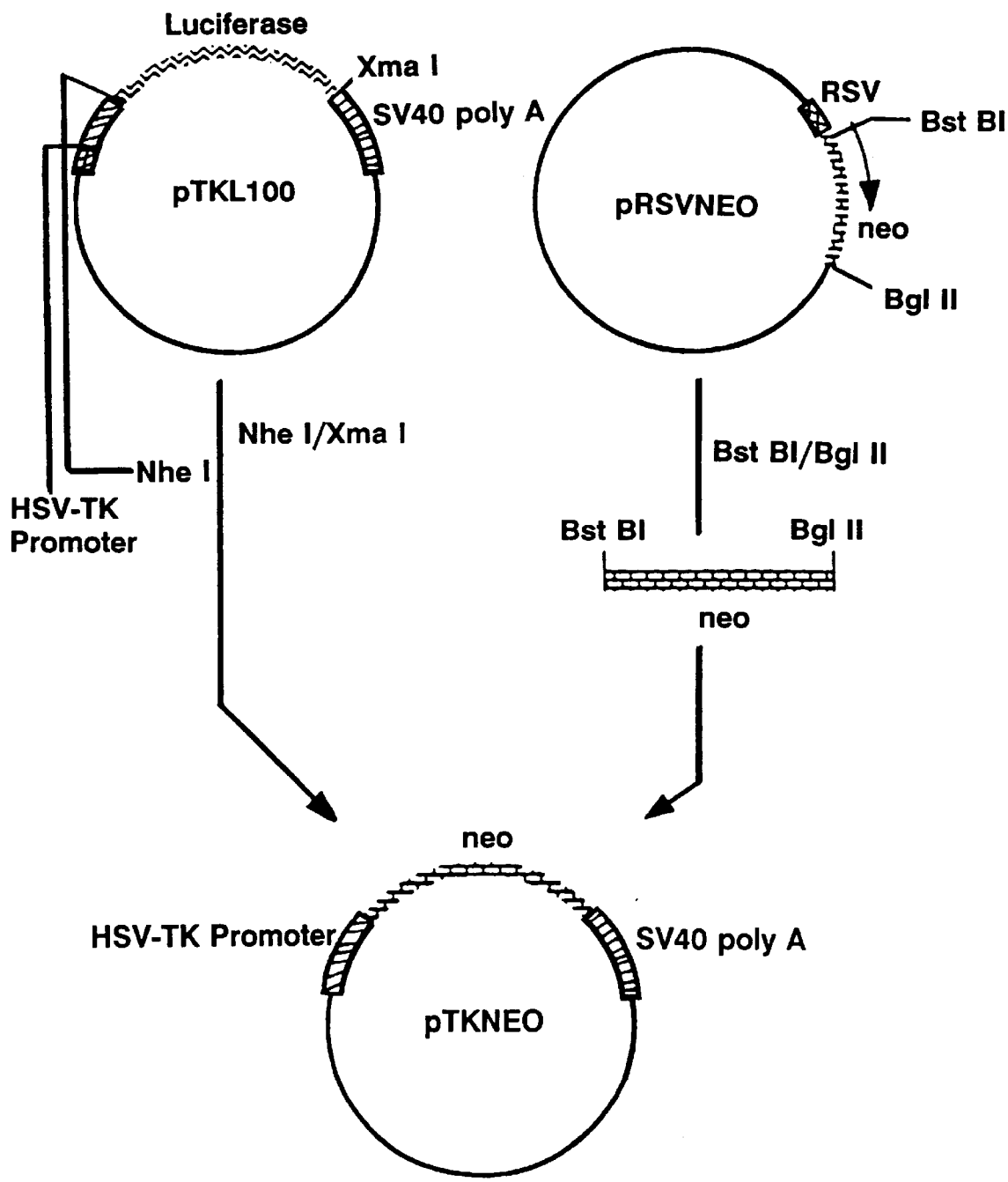
FIG. 17 is a diagrammatic representation of the construction of the plasmid pTKNEO which contains the neo gene, from a ≈3.5 kb NheI/XmaI fragment from pTKL100, and the ≈0.9 kb BstBI/BglII fragment containing the neo coding region from pRSVNEO.
Figure 18:
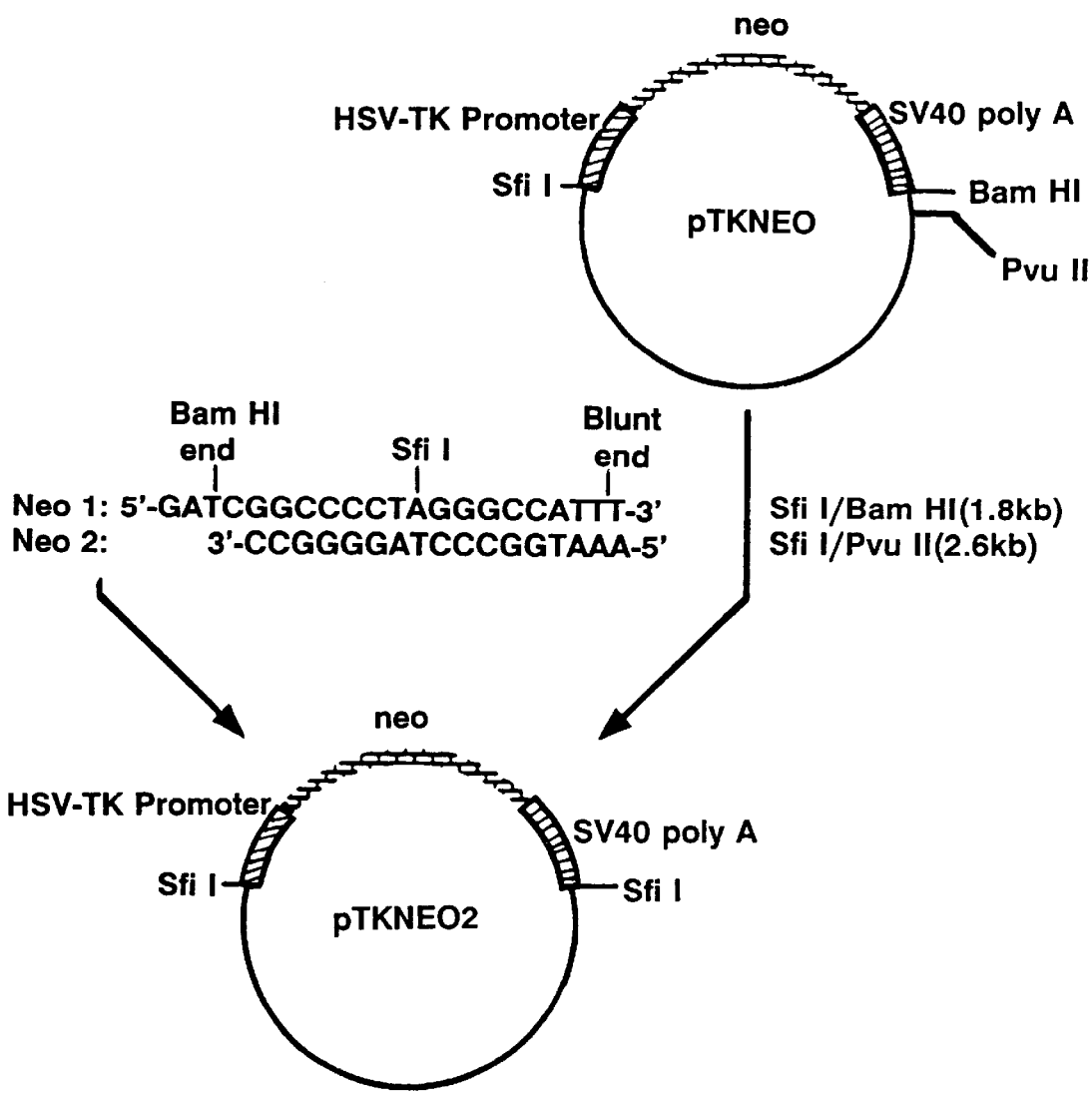
FIG. 18 is a diagrammatic representation of the construction of the plasmid pTKNEO2 from the plasmid pTKNEO and the oligonucleotides Neo 1 and 2.
Figure 19:
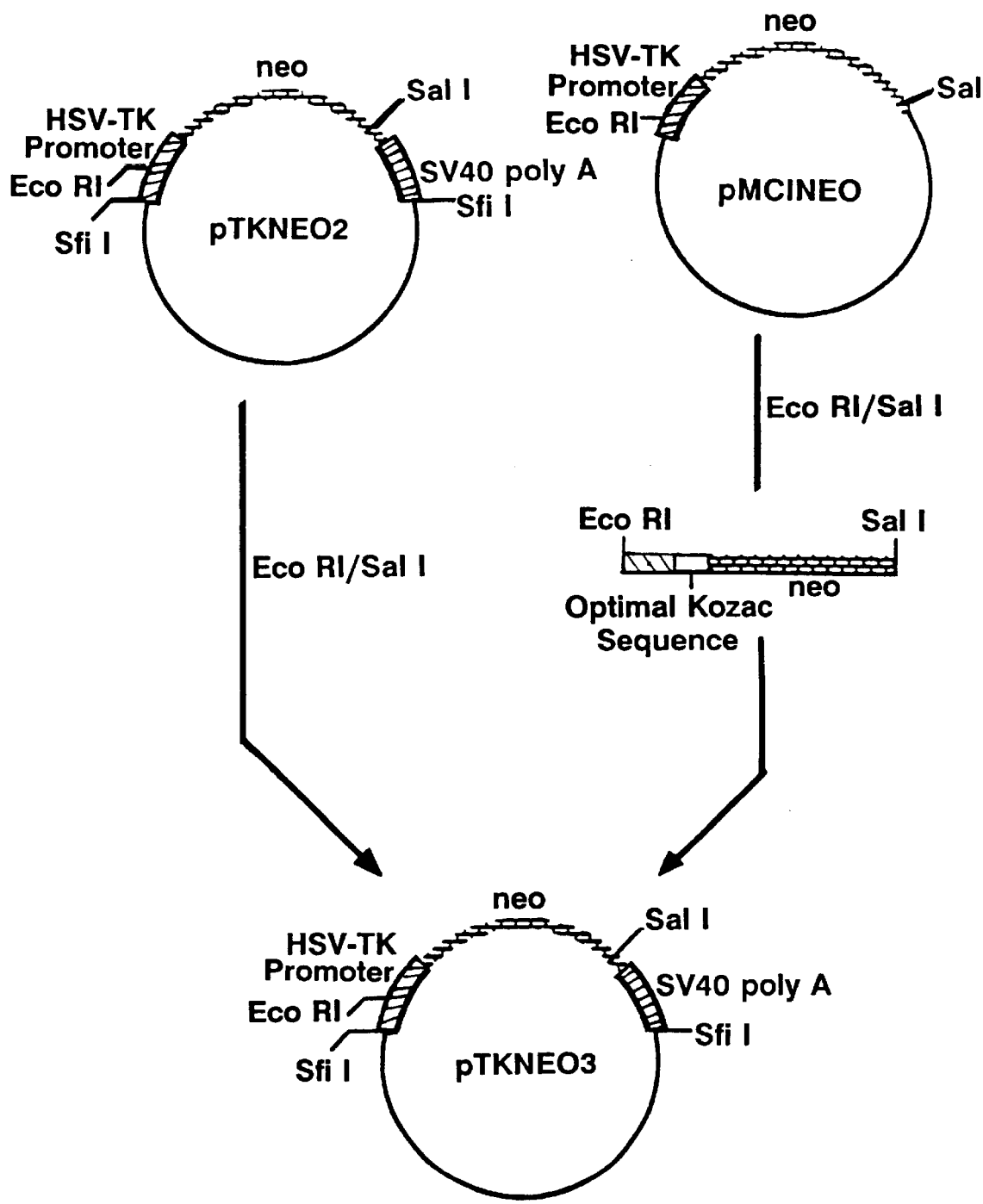
FIG. 19 is a diagrammatic representation of the construction of the plasmid pTKNEO3 from the plasmid PTKNEO2 and a ≈0.9kb EcoR1/SalI fragment from pMC1NEO.

The neomycin resistance gene (neo) was then placed under control of the Herpes Simplex Virus thymidine kinase (HSV-TK) promoter to generate a resistance cassette which is free of known enhancer sequences. To do this the HSV-TK promoter was synthesized using four oligonucleotides (FIG. 15) designed according to published sequence information (31), and including an SfiI restriction site 5' of the HSV-TK sequences. These oligonucleotides were phosphorylated, annealed, ligated and inserted into pUV100 digested previously with HindIII/NheI, generating the vector pTKL 100 (FIG. 16). After verifying the HSV-TK sequence, the ≈3.5 kb NheI/SmaI fragment was isolated from pTKL100, and the ≈0.9 kb BstBI/BglII fragment containing the neo coding region was isolated from pRSVNEO (14). These two fragments were filled in with Klenow polymerase and ligated to form PTKNEO (FIG. 17). An additional SfiI site was then inserted 3' of the neo gene by isolating the ≈1.8 kb SfiI/BamHI and ≈2.6 kb SfiI/PVUII fragments of pTKNEO and conducting a three way ligation along with a synthesized SfiI oligonucleotide generating pTKNEO2 (FIG. 18). The HSV-TK/NEO vector containing an optimized Kozac sequence was also utilized (Stratagene, La Jolla, Calif., pMC1NEO). An additional vector was constructed by replacing the ≈0.9 kb EcoRI/SalI fragment of pTKNEO2 with the ≈0.9 kb EcoRI/SalI fragment from pMC1NEO. This vector was termed pTKNEO3. (FIG. 19).

D. Molecular Cloning of Hematopoietic Promoters and Insertion into the OSI Mammalian Expression Shuttle Vector

1. Strategy

This section describes: (a) the molecular cloning of transcriptionally modulatable regulatory sequences of several genes of interest (in this case members of the family of hematopoietic growth factors) and (b) the making of constructs where these regulatory sequences now control the expression of the luciferase gene. To make such constructs, several kilobases of sequence upstream of the transcription start site, along with 5' untranslated sequences up to the translation start site (ATG), of a gene of interest were inserted 5' of the luciferase coding region. In this way constructs can be made where all sequences upstream of their translation start site are from the gene of interest, and all coding sequences are from the luciferase gene. How this was accomplished for the hematopoietic growth factor genes is described in sections D2-6.

2. Human Granulocyte-Macrophage Colony Stimulating Factor (GM-CSF)

Figure 20:
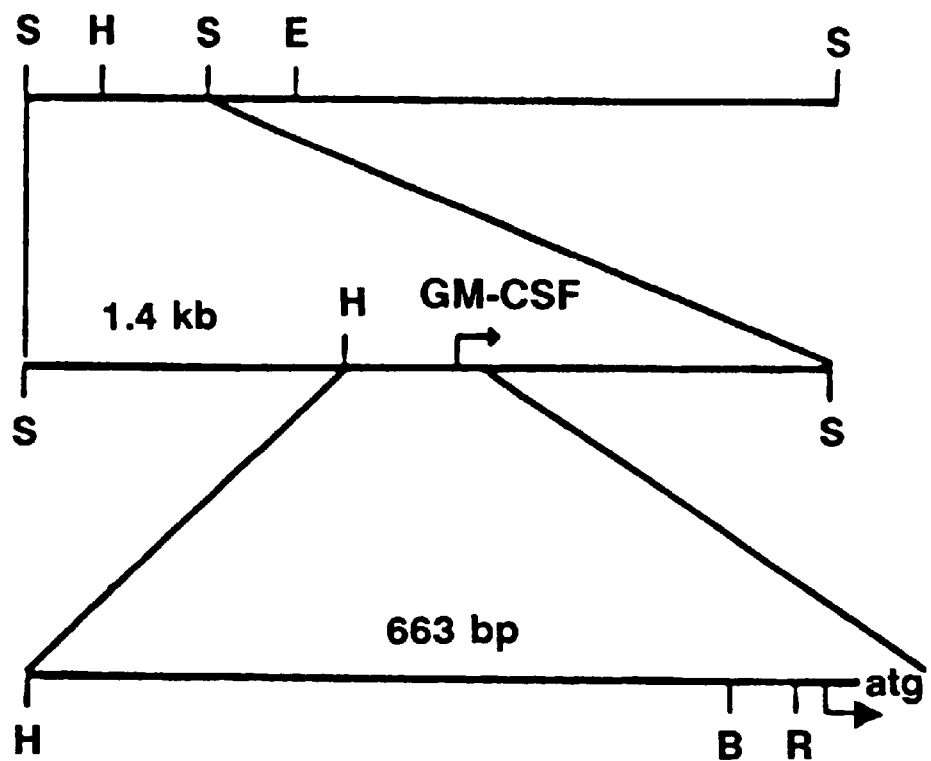
FIG. 20 is a partial restriction enzyme cleavage map of a human genomic clone which contains the entire GM-CSF coding region.

Cloning of GM-CSF promoter sequences was performed by using oligonucleotide probes based on the GM-CSF genomic sequence (20). Two DNA oligonucleotide probes were synthesized, one corresponding to GM-CSF sequences 5' of the coding region (5' GGTGACCACAAAATGC-CAGGGAGGCGGG 3') and the other to sequences in the first exon (5' GCAGGCCACAGTGCCCAAGAGACAG-CAGCAGGCT 3'). The oligonucleotide probes were used to screen a human leukocyte cell genomic DNA library (Clontech, Palo Alto, Calif.) following the manufacturer's instructions. One clone was obtained which contains the entire GM-CSF coding region along with 2 kb of upstream sequences (see FIG. 20).

Figure 23:
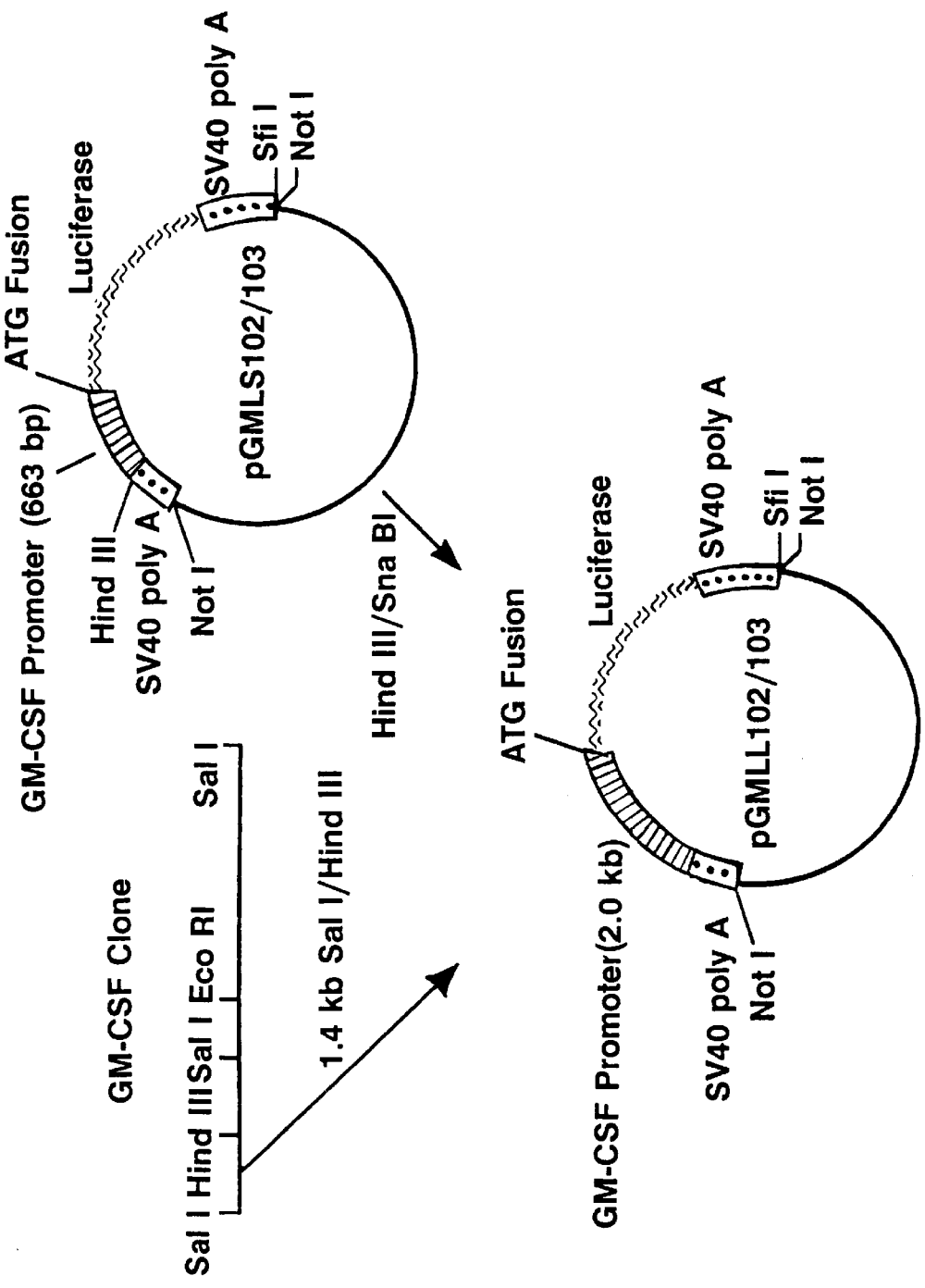
FIG. 23 is a diagrammatic representation of the construction of plasmids pGMLL102 and pGMLL103 from the plasmid pGMLS102 and the GM-CSF clone and the plasmid pGMLS103 and the GM-CSF clone, respectively.

All routine subcloning procedures were performed as described by Maniatis et al. (1982), (28) unless otherwise noted. The ≈0.7 kb HindIII/RsaI fragment of the GM-CSF clone (FIG. 20) was inserted into pUC 18 previously digested with HindIII/HincII. The ≈0.7 kb HindIII/SmaI fragment was then isolated from the resulting vector and cloned into pUV 100 digested previously with HindIII/SnaBI, thereby generating pGMLUCI (FIG. 22.) In order to correctly fuse the GM-CSF ATG with the coding region of luciferase, four oligonucleotides (FIG. 21) were synthesized, phosphorylated, annealed, ligated, and inserted into pUC19 previously digested with Eco RI/XbaI, generating pGM-1 (FIG. 22). pGM-1 was then sequenced (Sequenase Kit, US Biochemicals, Cleveland, Ohio) using the M13 forward (U.S. Biochem.) and reverse primers (Pharmacia, Piscataway, N.J.) to ensure that there were no mutations in the synthesized oligonucleotides. The ≈1.8 kb BstEII/ScaI fragment from pGM-1 was then isolated and ligated to the ≈1.5 kb BstEII/ScaI fragment from PGMLUCI to generate pGN-2 (FIG. 22). pGM-2 was then digested with Hind III/XbaI and the ≈0.7 kb fragment was cloned into pUV 102 and pUV 103 previously digested with HindIII/XbaI. This generated pGMLS102 and pGMLS103 (FIG. 22), which contain 663 bp of GM-CSF sequence 5' of the ATG fused directly to the second (correct) ATG of luciferase and the rest of the luciferase coding region. An additional ≈1.4 kb of upstream sequences were cloned into this construct by isolating the ≈1.4 kb SalI/HindIII fragment from the GM-CSF clone (FIG. 20), blunting the SalI end by filling in with Klenow polymerase, and inserting the fragment into pGMLS102 and pGMSL103 previously digested with HindIII/SnaBI. This step generated pGMLL102 and PGMLL103, respectively (FIG. 23). Finally, the pTKNEO2 and PTKNEO3 ≈1.8 kb SfiI fragments were cloned directly into the SfiI site of pGMLL103 to generate pGMLL103 NEO2 and pGMLL103 NEO3.

3. Human Macrophage Colony Stimulating Factor (M-CSF or CSF-1)

Sequence information on the M-CSF gene (23) was used to synthesize an oligonucleotide probe (CSF1-a) to screen a human leukocyte genomic DNA library (Clontech, Palo Alto, Calif.) according to the supplier's instructions. The sequence of the oligonucleotide probe was:

5' CCGGCGCGGTCATACGGGCAGCTGG 3' (CSF1-a)

Figure 24:
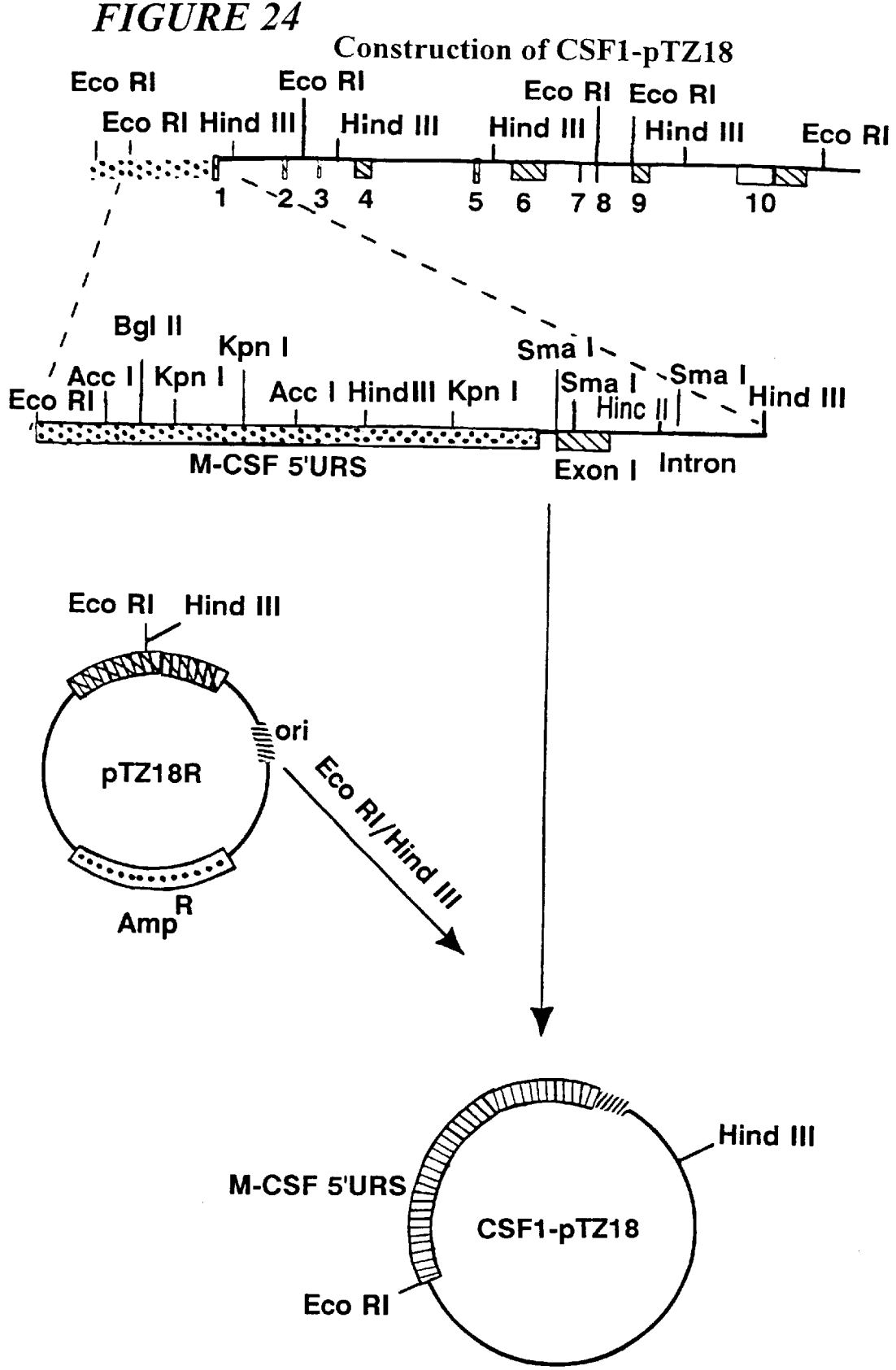
FIG. 24 is a diagrammatic representation of the construction of the plasmid CSF1-pTZ18 from the plasmid pTZ18R and a gene fragment comprising the first exon and 5' flanking region of M-CSF.
Figure 25:
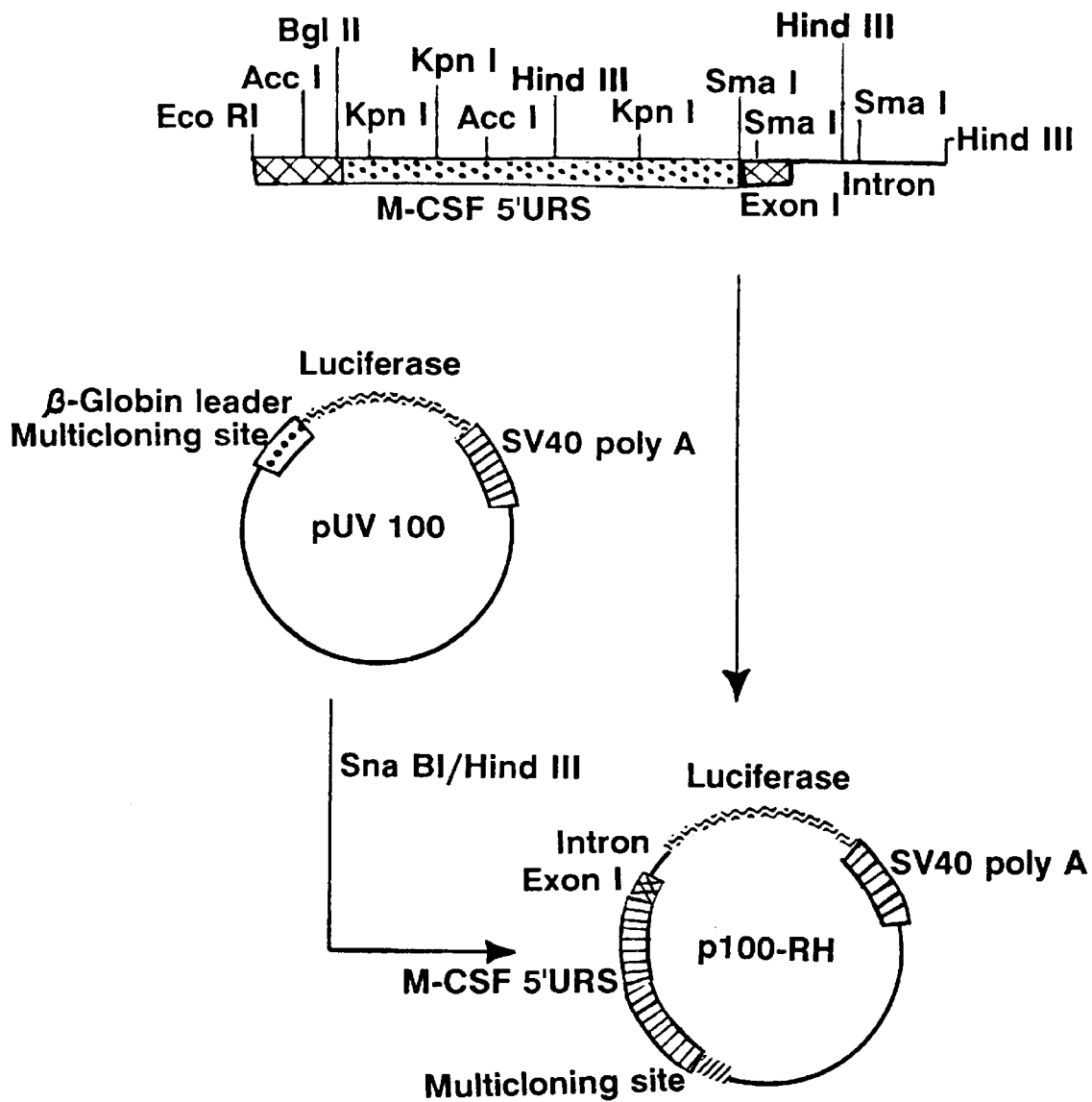
FIG. 25 is a diagrammatic representation of the construction of the plasmid p100-RH from the plasmid pUV100 and the gene fragment comprising the first exon and 5' flanking region of M-CSF from the plasmid CSF1-pTZ18.

The sequence of this probe corresponds to sequences within the second exon of the M-CSF gene. One of the clones isolated from the leukocyte library contains a 5 kb EcoRI/HindIII fragment which includes the first exon and 5' flanking region of M-CSF. This fragment was inserted into the pTZ18R vector (Pharmacia, Piscataway N.J.) which had been previously digested with EcoRI/HindIII resulting in the vector CSF1-pTZ18 (FIG. 24). The same fragment was isolated from CSF1-pTZ18, blunt ended at the EcoRI end, and inserted into the pUV100 vector which had been previously digested with SnaBI/HindIII, resulting in the vector p100-RH (FIG. 25). The M-CSF untranslated leader sequence (23) was then fused to the first codon of the luciferase coding region as follows: (a) a 740 bp PstI/PvuII fragment was isolated from CSF1-pTZ18 containing 570 bp of the M-CSF promoter and 170 bp of the untranslated leader sequence; (b) oligonucleotides containing sequences from the 3' end of the M-CSF leader sequence and the 5' end of the luciferase coding region were synthesized:

5' CTGCCCGTATGGA 3' (CSF-luci5)

Figure 11B:
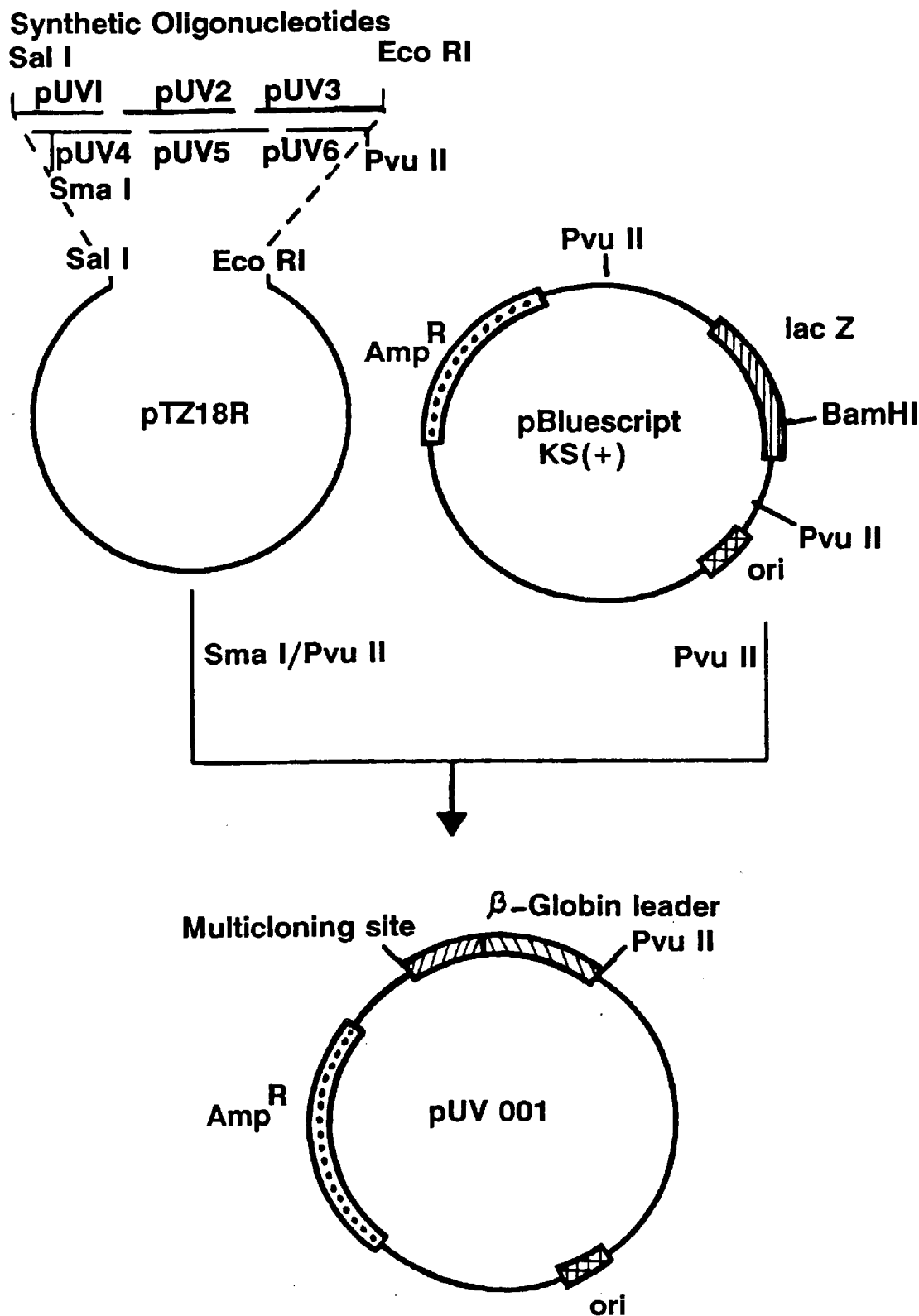
FIG. 11*b* is a diagrammatic representation of the construction of the plasmid pUV001 from the plasmids pTZ18R and pBluescript KS(+).
Figure 12:
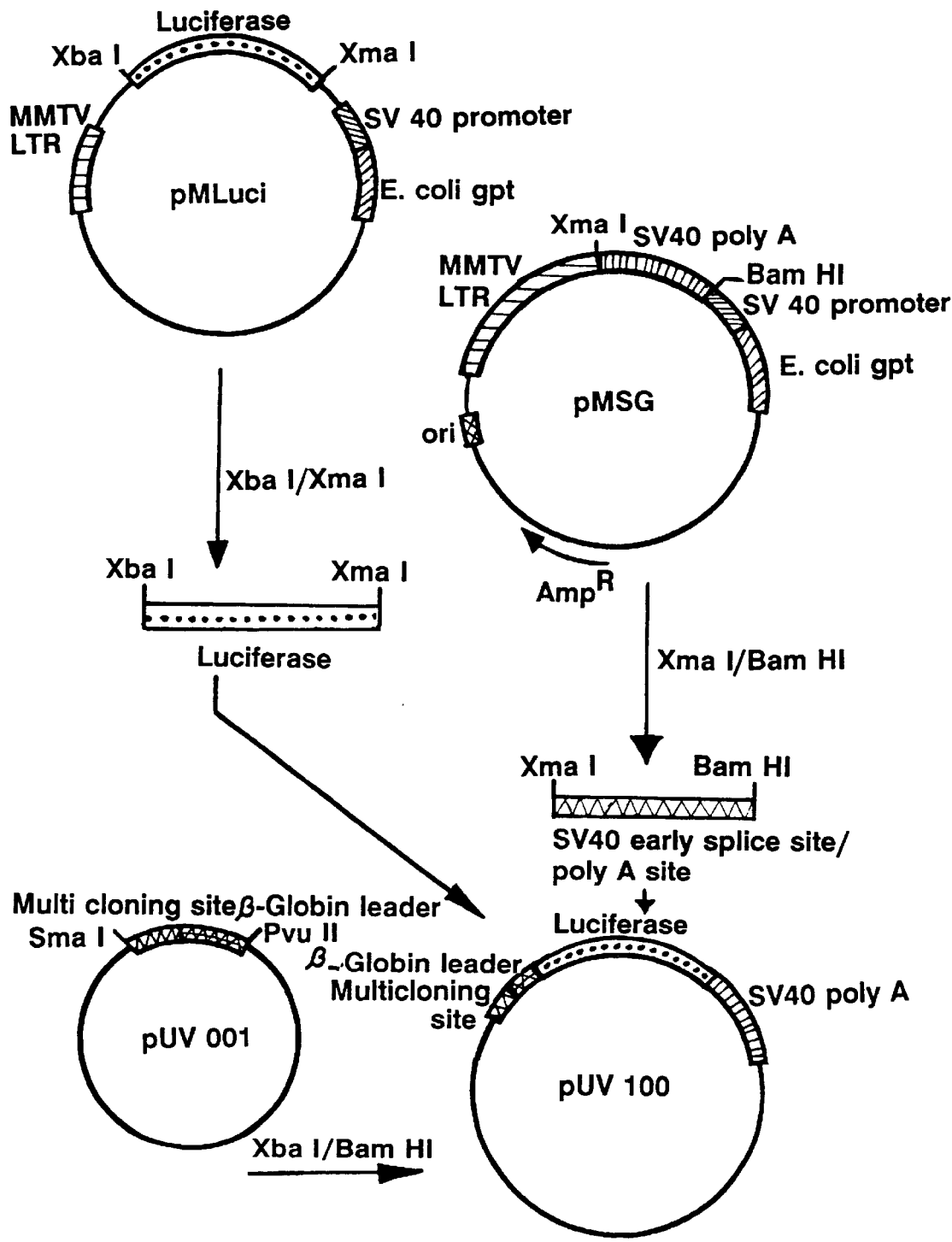
FIG. 12 is a diagrammatic representation of the construction of the plasmid pUV100 from the plasmid pUVO01 and two DNA fragments, the XbaI/XmaI fragment from pMLuci and the XmaI/BamHI fragment from pMSG.
Figure 26:
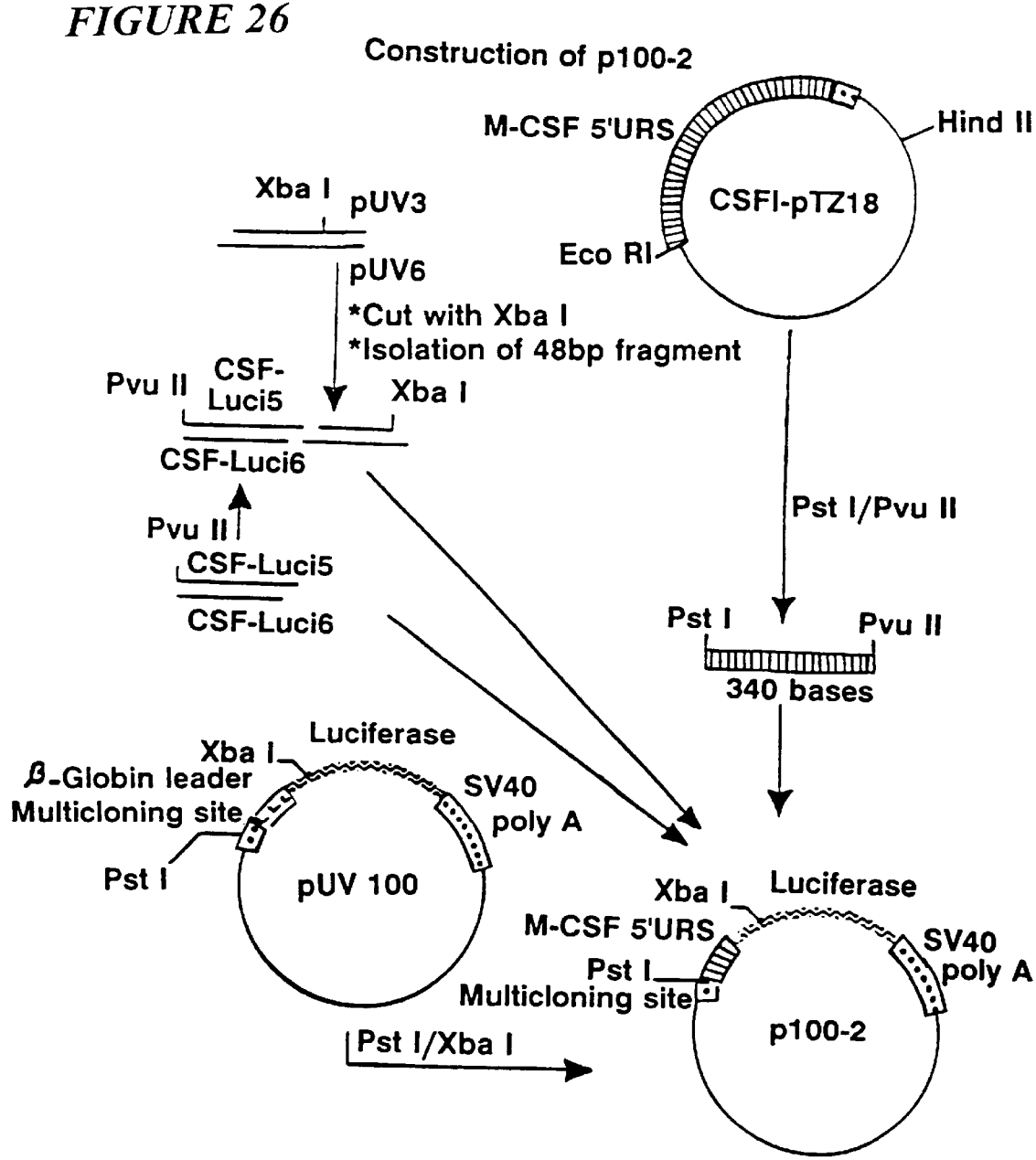
FIG. 26 is a diagrammatic representation of the construction of the plasmid p100-2 by insertion of a PSTI/PVUII fragment from CSFI-pTZ18 and synthetic oligonucleotides into the plasmid pUV100.
Figure 27:
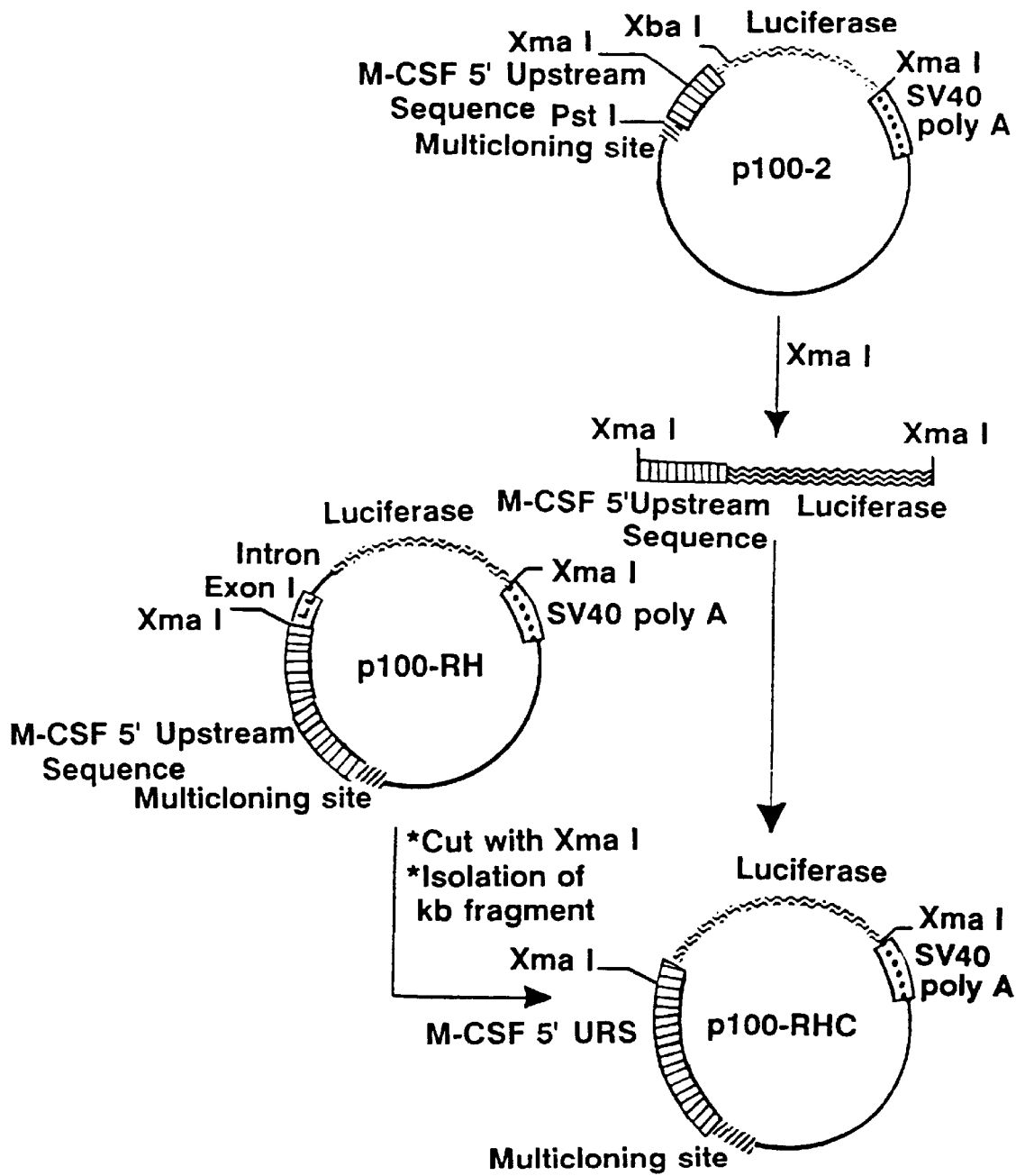
FIG. 27 is a diagrammatic representation of the construction of p100-RHC by insertion of short M-CSF 5' upstream sequences fused to the luciferase coding sequence into the plasmid p100-RH containing a longer M-CSF 5' upstream fragment.
Figure 28:
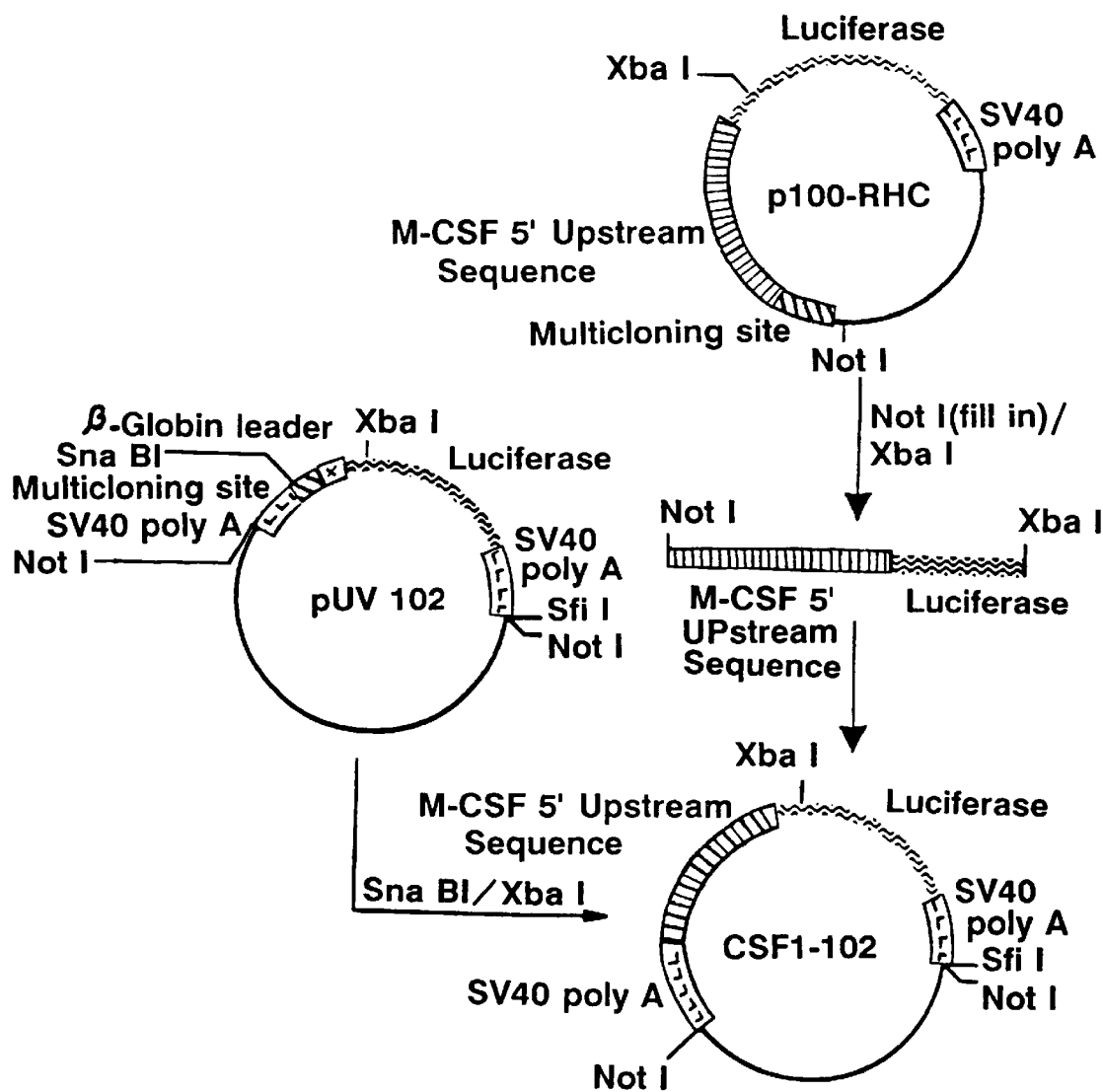
FIG. 28 is a diagrammatic representation of the construction of pCSF1-102 from a 5 kb NotI/Xba I fragment isolated from p100-RHC and inserted into pUV102.

5' ACGGGCAG 3' (CSF-luci6);

(c) oligonucleotides pUV3 and pUV6 (previously used to construct pUV001, FIG. 11(b)) were annealed, and digested with XbaI to release a 48 bp fragment which contains 48 bases of the luciferase coding region; (d) DNA fragments and oligonucleotides (from a, b and c) were ligated and inserted into pUV100 previously digested with PstI/XbaI to yield p100-2 (FIG. 26). A construct containing a larger M-CSF promoter fragment (5 kb) was also made. A 2 kb XmaI fragment was isolated from the plasmid p100-2. This fragment contains the 3' end of the M-CSF leader sequence fused to the luciferase start codon. The 2 kb XmaI fragment was inserted in p100-RH previously digested with XmaI, to yield p100-RHC (FIG. 27). The fused 5 kb M-CSF promoter-luciferase construct was then inserted into pUV102 as follows: a 5 kb NotI/XbaI fragment (blunt ended at the NotI end) was isolated from p100-RHC and inserted into pUV102, previously digested with SnaBI/XbaI, to generate CSF1-102 (FIG. 28). This construct was then used for transfections of 5637 human bladder carcinoma cells.

4. Human Granulocyte Colony Stimulating Factor (G-CSF)

Figure 29:
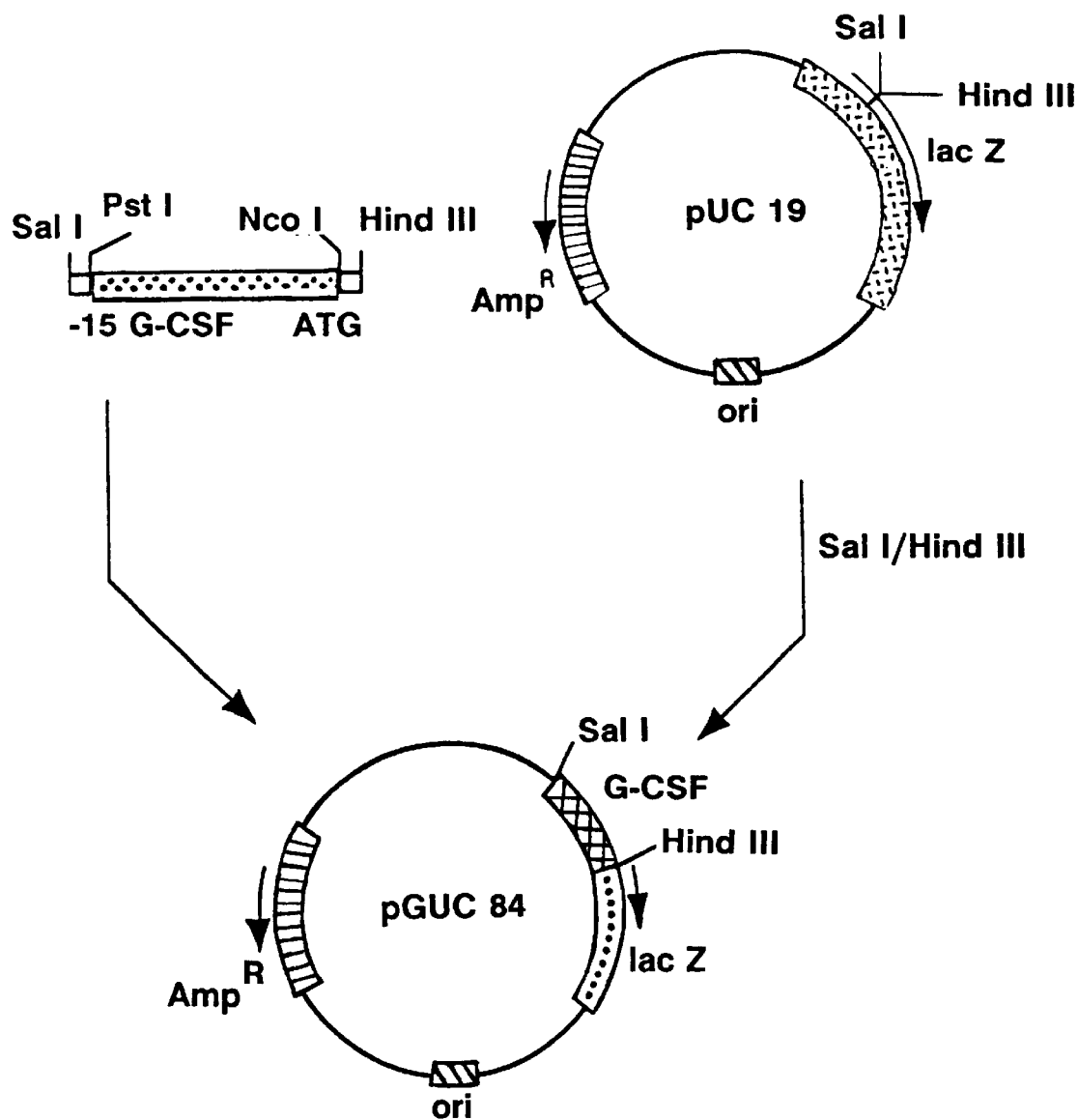
FIG. 29 is a diagrammatic representation of the construction of pGUC84 from oligonucleotides containing the G-CSF leader sequence from +15 to the ATG cloned into the plasmid pUC19.
Figure 30:
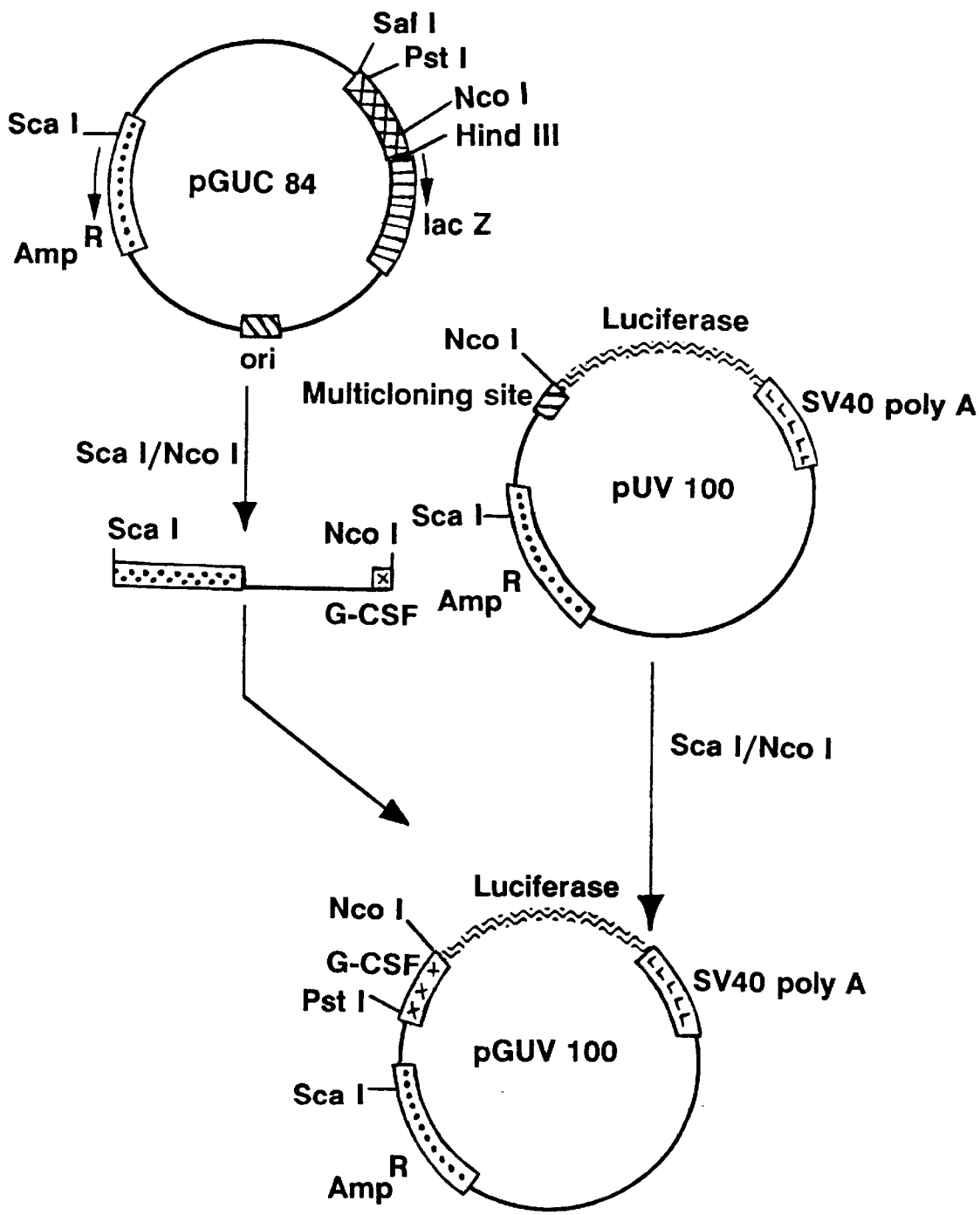
FIG. 30 is a diagrammatic representation of the construction of pGUV100 from the NcoI/ScaI fragment from pGUC84 containing G-CSF leader sequences cloned into the plasmid pUV100.
Figure 31:
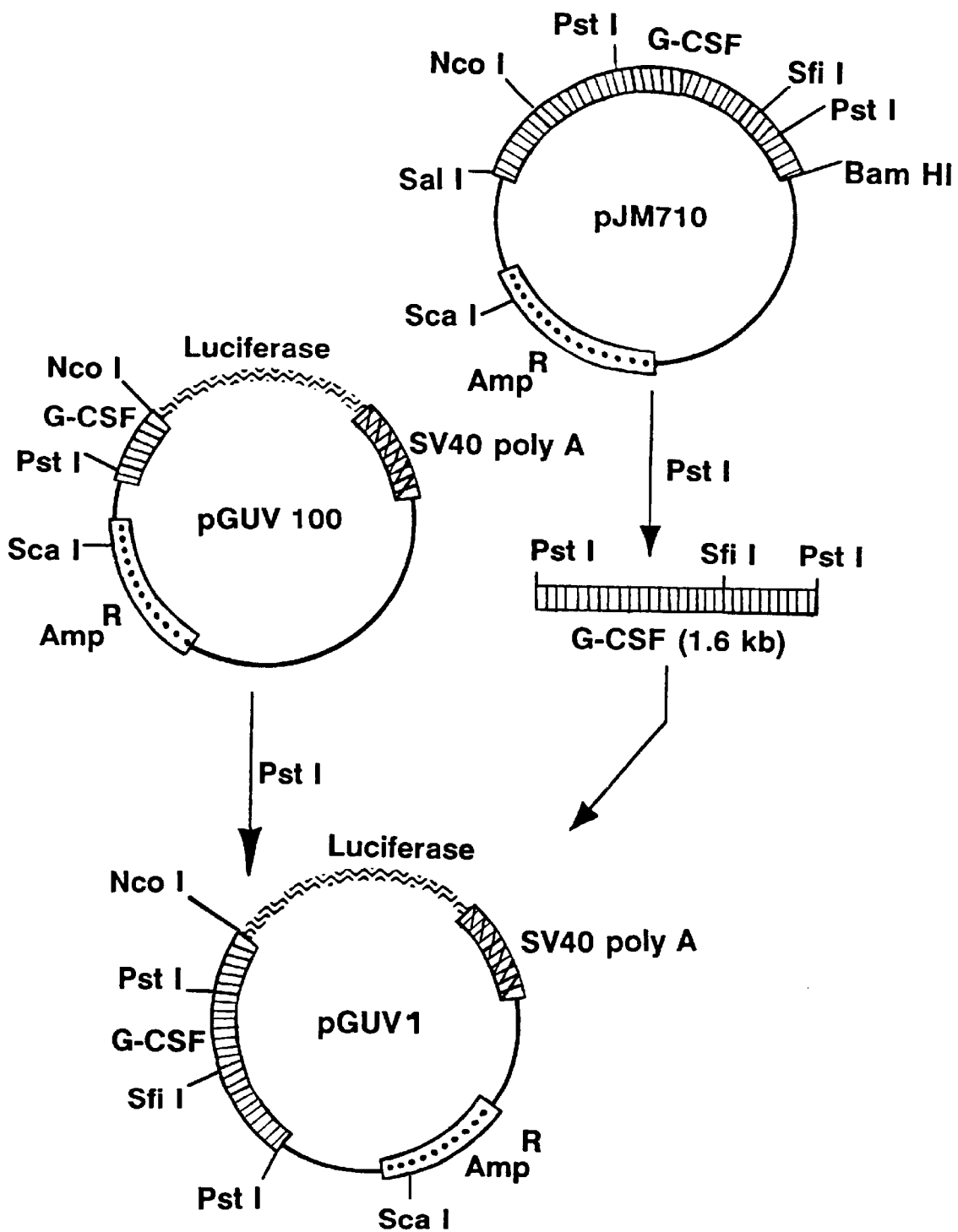
FIG. 31 is a diagrammatic representation of the construction of pGUV1 from the Pst I fragment of the G-CSF promoter from the plasmid pJM710 inserted into the Pst I site in pGUV 100.
Figure 32:
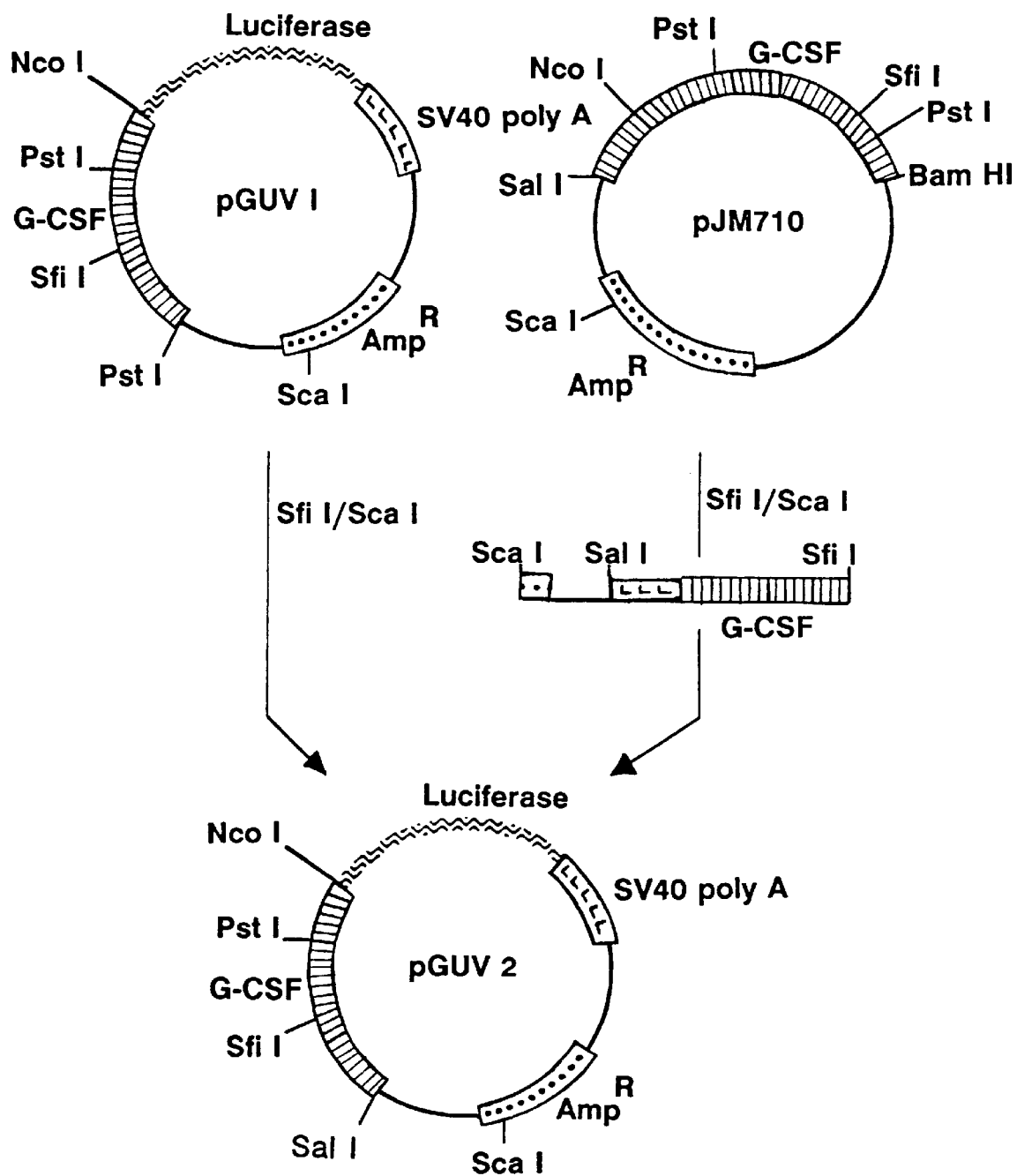
FIG. 32 is a diagrammatic representation of the construction of the plasmid pGUV-2 by insertion of more G-CSF upstream sequences from pJM710 into pGUV1.
Figure 33:
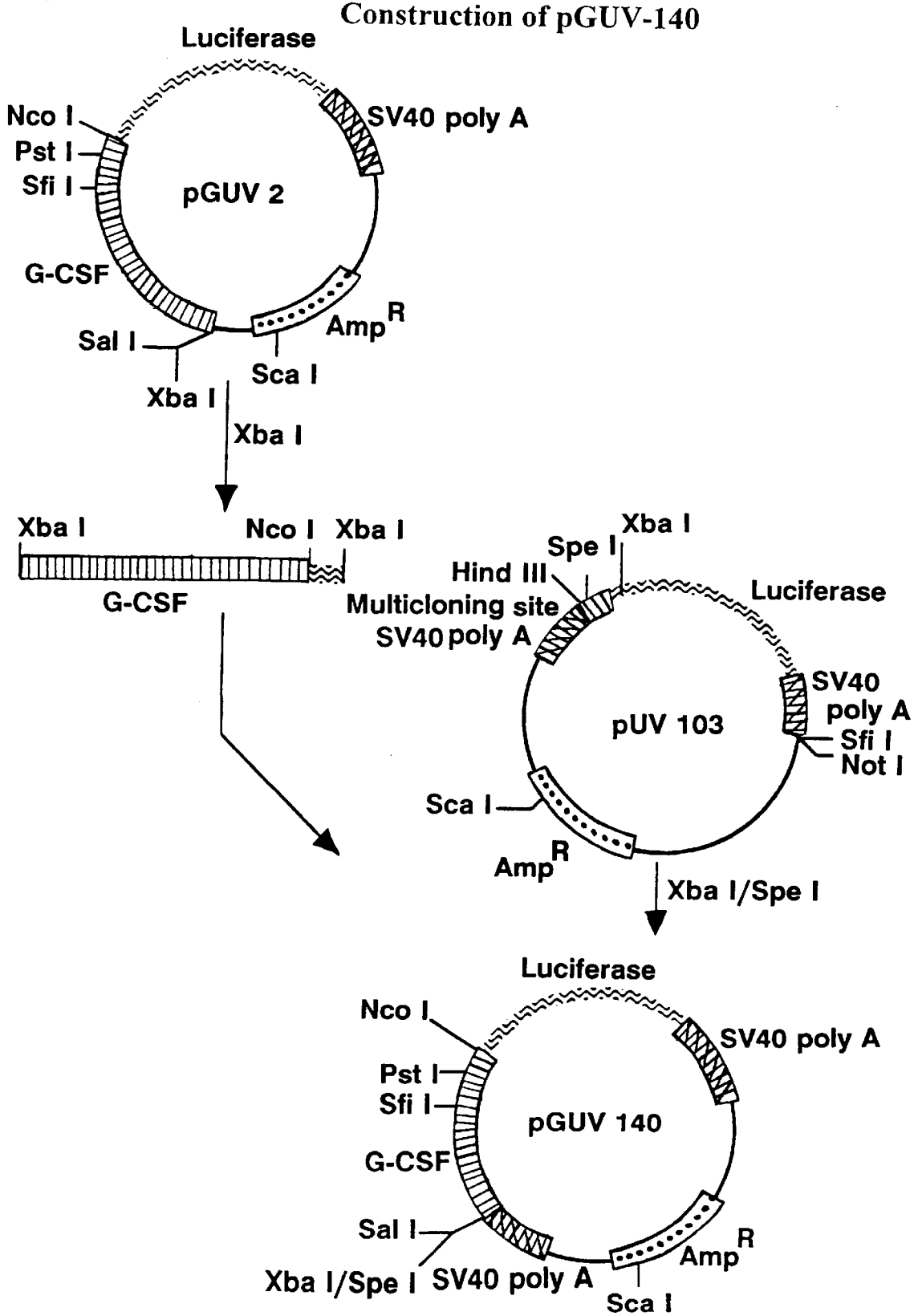
FIG. 33 is a diagrammatic representation of the construction of the plasmid pGUV140 from the XbaI fragment from pGUV2 containing the G-CSF-luciferase fusion and the plasmid pUV103.
Figure 34:
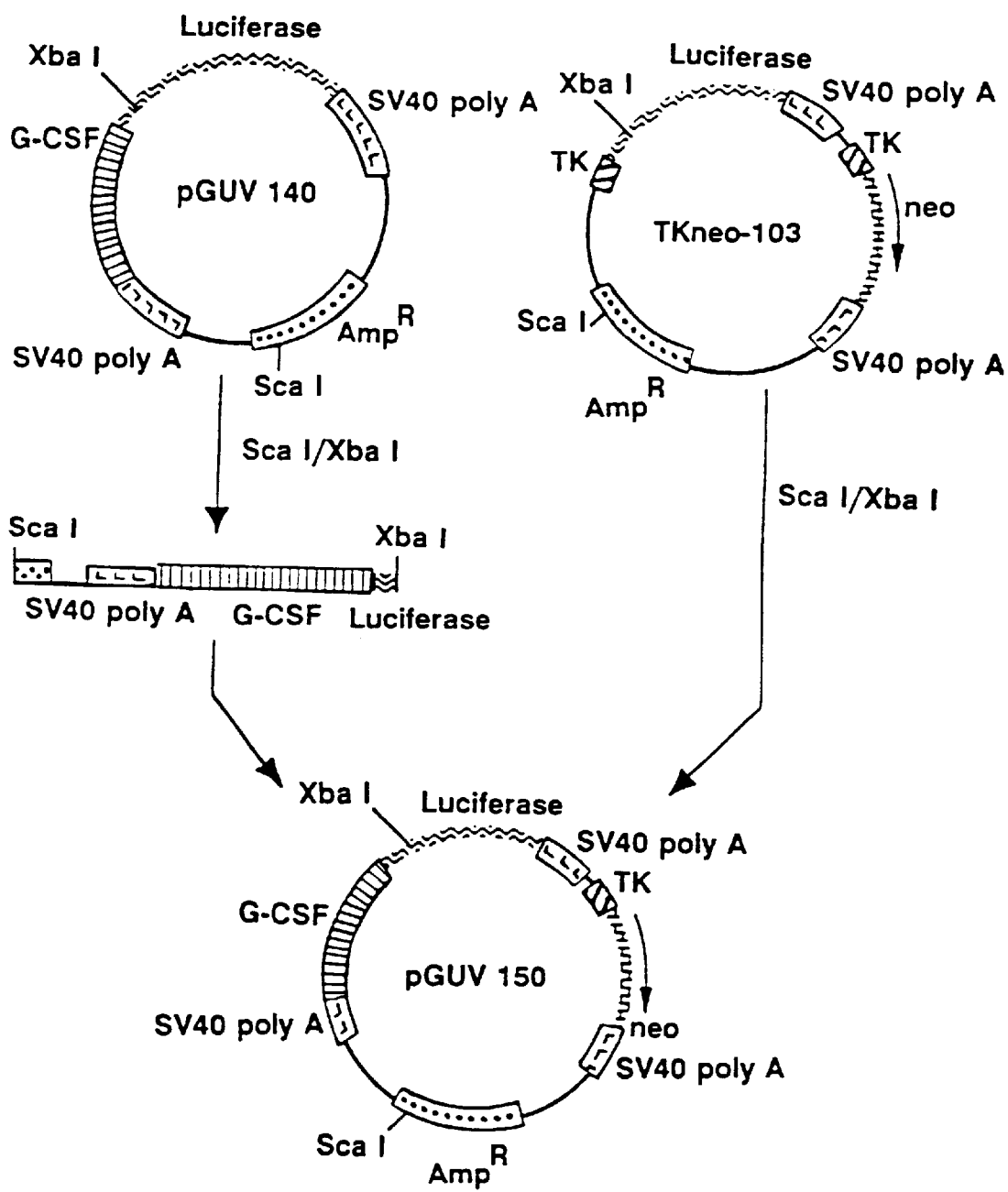
FIG. 34 is a diagrammatic representation of the construction of the plasmid pGUV150 from the ScaI/XbaI fragment from pGUV140 which contains the G-CSF-luciferase fusion and the plasmid pTKNEO-103.

Cloning of G-CSF sequences is described in Experimental Details, section B-3. In order to correctly fuse the G-CSF upstream sequences to the luciferase start codon, oligonucleotides were synthesized which contain the G-CSF leader sequence from +15 to the ATG (32), and were cloned into pUC19 to create pGUC84 (FIG. 29). The sequence of the inserted fragment was determined and was found to be as expected. The G-CSF-oligonucleotide-containing NcoI/ScaI fragment from pGUC84 was then isolated and ligated to the luciferase-containing NcoI/ScaI fragment from pUV100 to create pGUV100 (FIG. 30). Following this, the PstI fragment of the G-CSF promoter was isolated from pJM710 (FIG. 7) and inserted into the PstI site in pGUV100 generating pGUV1(FIG. 31). The rest of the G-CSF promoter clone was added by ligating the G-CSF-luciferase containing SfiI/ScaI fragment from pGUV1 to the appropriate SfiI/ScaI fragment from pJM710, creating the plasmid pGUV2 (FIG. 32). The XbaI fragment from pGUV2 containing the G-CSF-luciferase fusion was then cloned into pUV103 previously digested with XbaI/SpeI, generating pGUV140 (FIG. 33). Finally, a TK-Neo cassette (Section C) was included by ligating the ScaI/XbaI fragment from pGUV140 which contains the G-CSF-luciferase fusion into pTKNEO103 previously digested with ScaI/XbaI, yielding the final vector pGUV150 (FIG. 34).

5. Erythropoietin (EPO)

Information on the EPO upstream and coding sequences has been published (27) and was used to synthesize two oligonucleotide probes (EP06 and EP08) to screen a human leukocyte genomic DNA library (Clontech, Palo Alto, Calif.) according to the supplier's instructions. The sequences of the oligonucleotide probes were:

5' AATGAGAATATCACTGTCCCAGACAC-CAAAGTTAATTTCTATGCC TGGAA 3' (EP08)

5' TTCCAGGCATAGAAATTAAC 3' (EP06)

Figure 35:
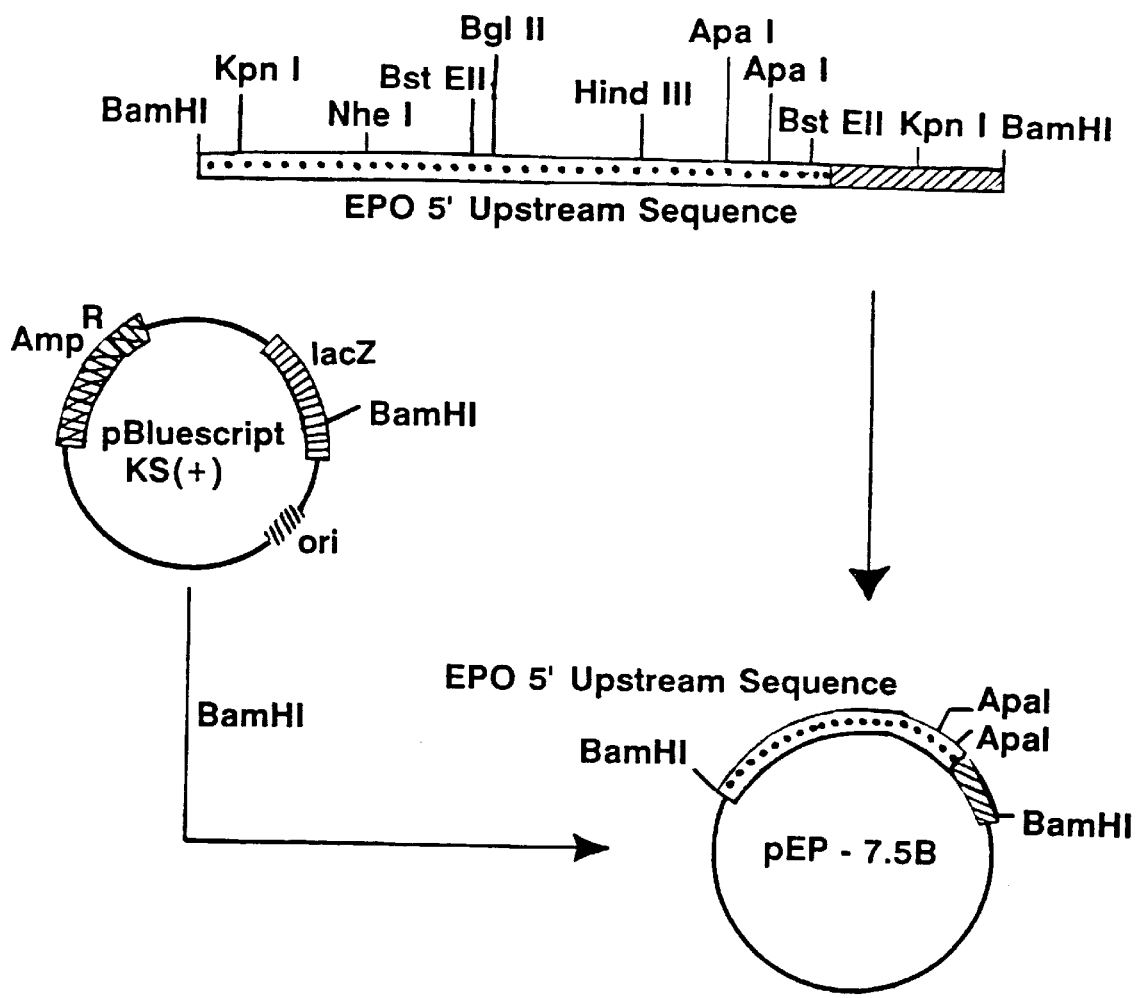
FIG. 35 is a diagrammatic representation of the construction of the plasmid pEP-7.5B from a 7.5 kb BamH1 fragment consisting of 6.2 kb of the EPO promoter region and the first three EPO exons and the plasmid pBluescript KS(+).

EP08 is complementary to sequences within the third exon of the EPO gene (27). EP06 is complementary to the 3' end of EP08 and was used as a primer for filling in the complementary strand of EP08 with labelled nucleotides, thereby generating a probe for cloning. One of the clones isolated from the leukocyte genomic DNA library contained a 7.5 kb BamHI fragment consisting of 6.2 kb of the EPO promoter region and the first three EPO exons. This fragment was inserted into the plasmid Bluescript KS(+) (Stratagene, La Jolla, Calif.), previously digested with BamHI, resulting in the vector pEP-7.5B (FIG. 35). The Epo leader sequence was fused to the start codon of the luciferase gene by using four synthetic oligonucleotides (EP09 to EP012). The sequences of the oligonucleotides were:

5' CCCGGTGTGGTCACCCGGCGCGCCCCAG-GTCGCTG AGGGACCCCGGCCAGGCGCGGA 3' (EP09)

5' CATCTCCGCGCCTGGCCGGGGTCCCT-CAGCGACCT GGGGCGCGCCGGGTGACCA-CACCGGGGGGCC 3' (EP010)

5' GATGGAAGACGCCAAAAACATCAA-GAAAGGCCCGG CGCCATTCTATCCT 3' (EP011)

5' CTAGAGGATAGAATGGCGCCGGGC-CTTTCTTGATG TTTTTGGCGTCTTC 3' (EP012)

Figure 36:
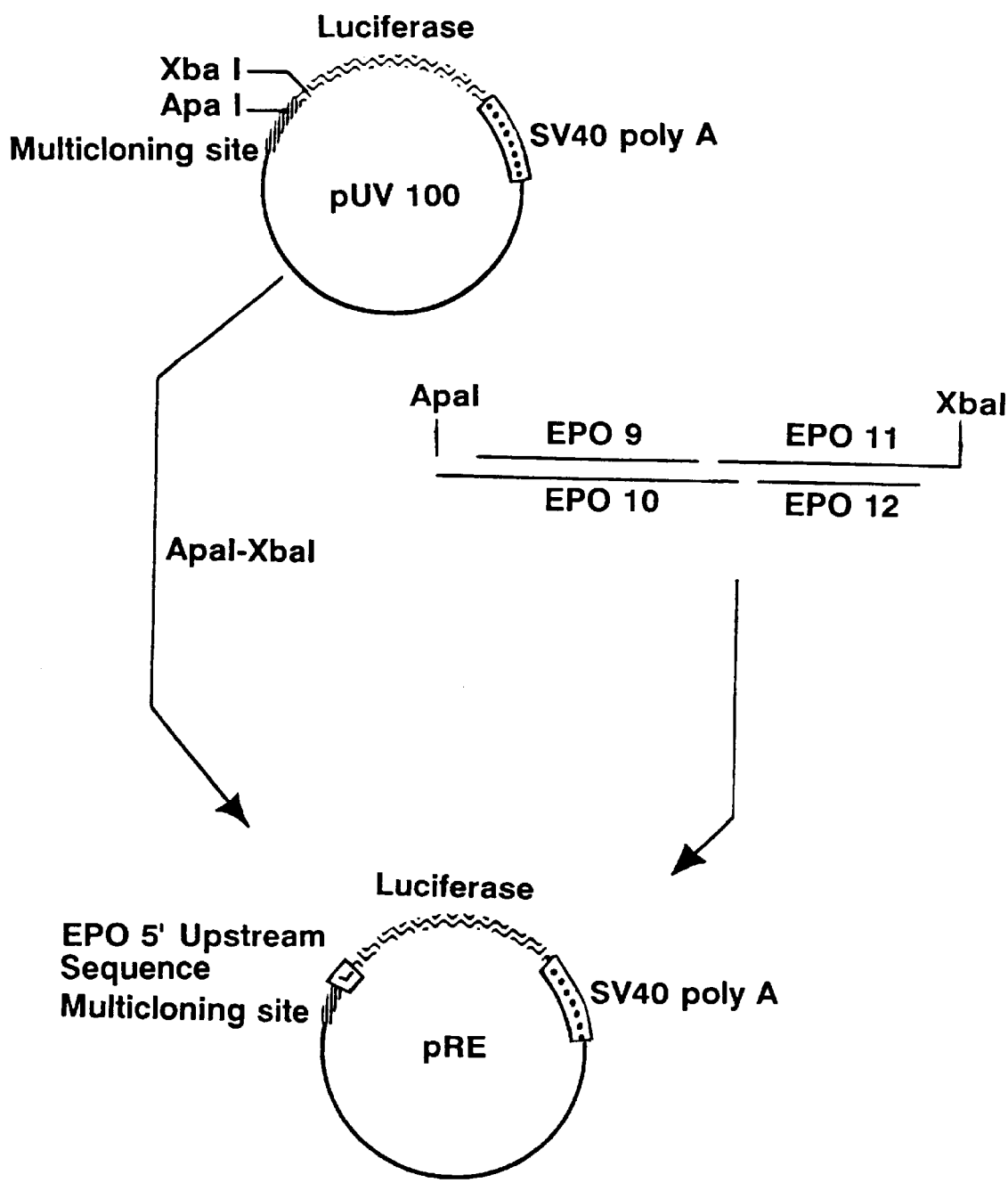
FIG. 36 is a diagrammatic representation of the construction of the plasmid pRE from oligonucleotides EPO 9–12 and the plasmid pUv100.
Figure 37:
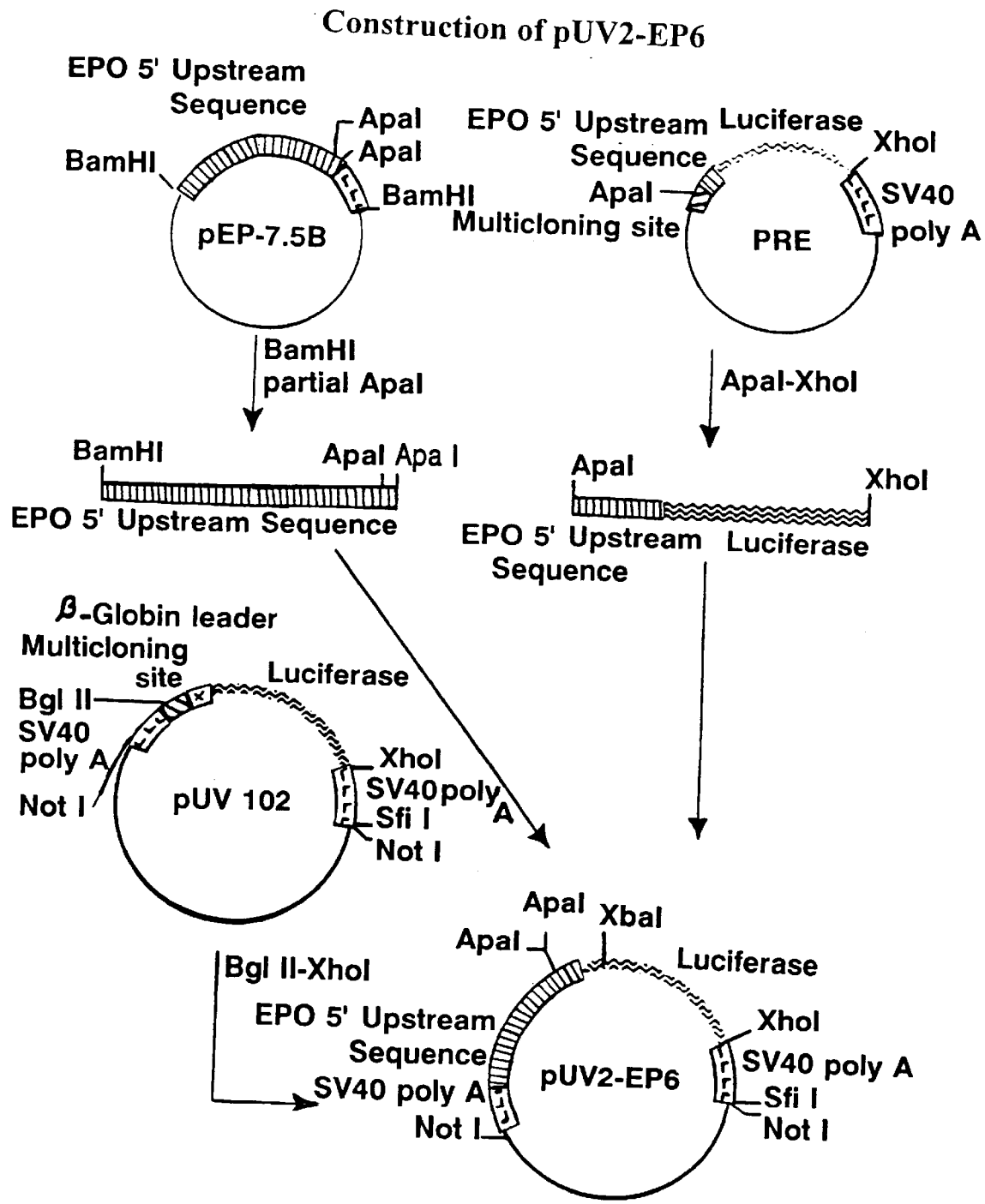
FIG. 37 is a diagrammatic representation of the construction of the plasmid pUV2-EP6 from a 6 kb fragment of EPO upstream sequences and the plasmid pUV 102.

The sequences of EP09 and EP011 consist of 63 bases upstream of the EPO translational start site fused to the first 53 bases of the luciferase coding region. EP010 and EP012 oligonucleotides are complementary to EP09 and EP011, respectively. These oligonucleotides were inserted into the plasmid pUV100 previously digested with ApaI/XbaI to generate the vector pRE (FIG. 36). 6 kb of EPO upstream sequence was cloned into pUV102 by inserting a 6.2 kb BamHI/partial ApaI fragment from pEP-7.5 B and a 1.7 kb ApaI/XhoI fragment from pRE into pUV102 previously digested with BglI/XhoI, yielding pUV2-EP6 (FIG. 37). The 1.8 kb SfiI fragment from pTKNEO3 (FIG. 19) was then inserted into pUV2-EP6 previously digested with SfiI, generating pEP6.0-102-TKNEO.

6. Interleukin-3 or Multi-CSF (IL-3)

Figure 38:
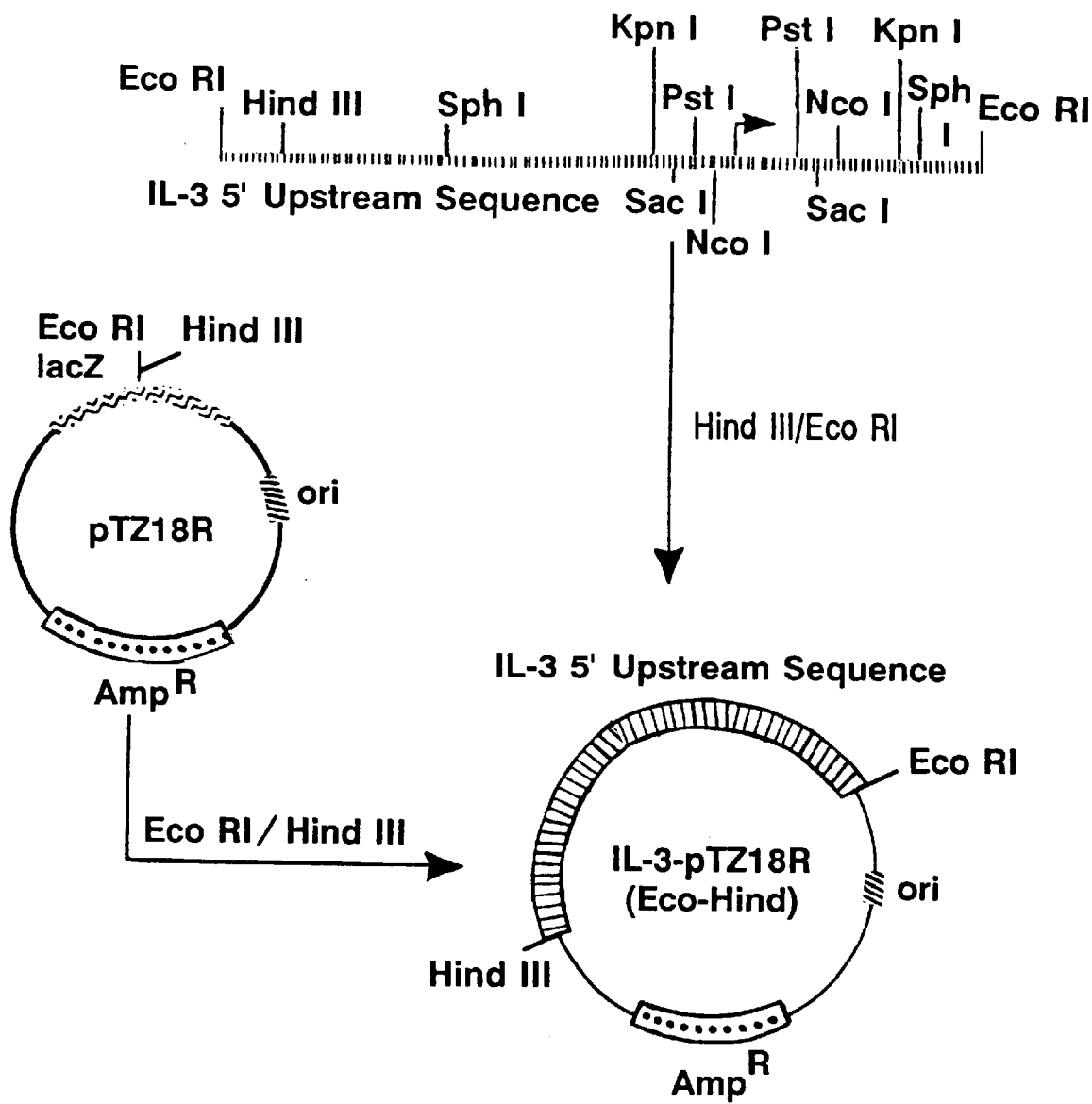
FIG. 38 is a diagrammatic representation of the construction of the plasmid IL-3-pTZ18R from IL-3 upstream sequences and the plasmid pTZ18R.
Figure 39:
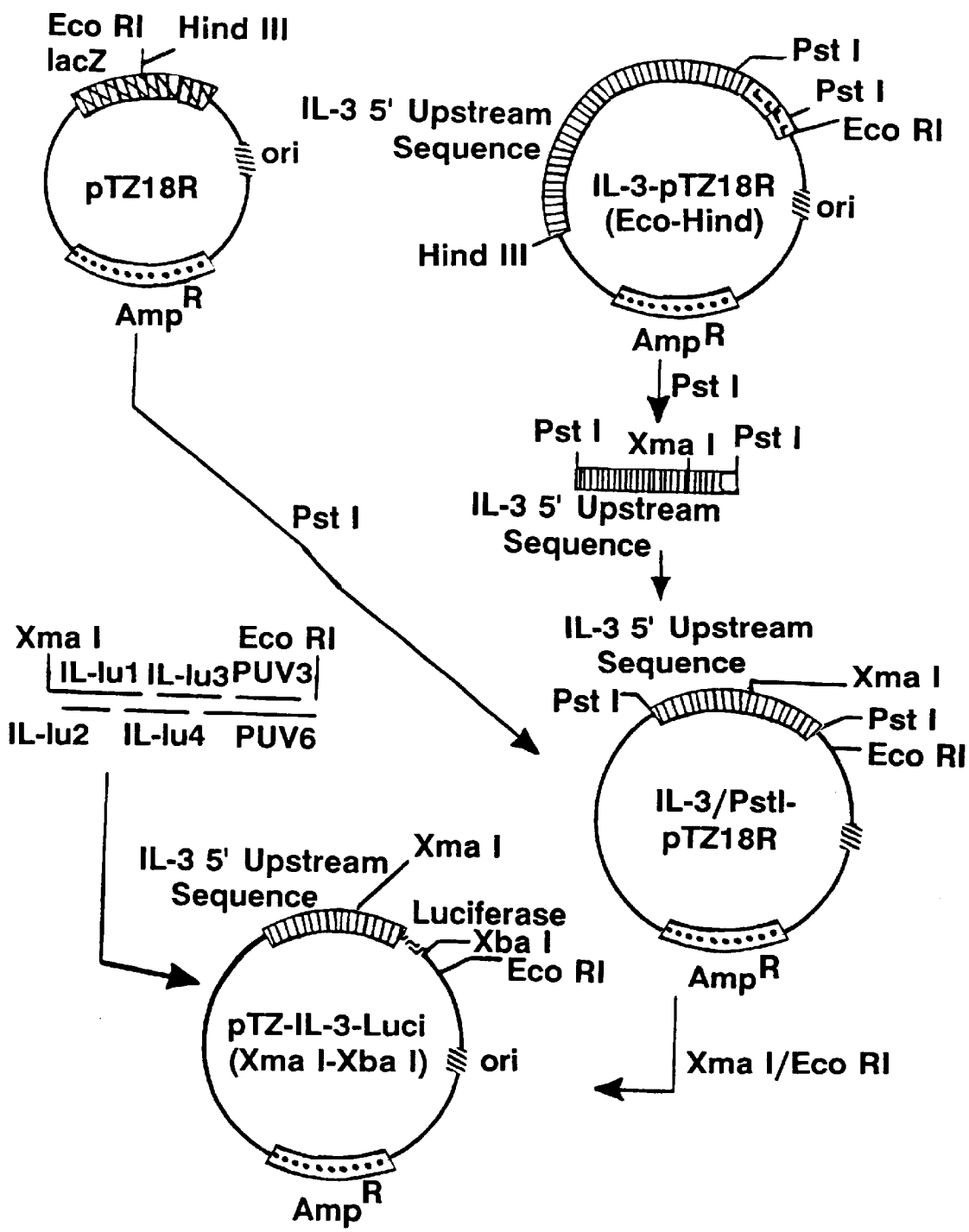
FIG. 39 is a diagrammatic representation of the construction of the plasmid pTZ-IL-3-Luci from oligonucleotides IL-lu-1 to IL-lu-4, pUV-3 and pUV-6 and the plasmid IL3/PstI-pTZ18R.

Information on the IL-3 promoter and coding sequences (40-41) was used to synthesize an oligonucleotide probe (IL-3 II) to screen a human leukocyte genomic DNA library (Clontech, Palo Alto, Calif.) according to the supplier's instructions. The sequence of the oligonucleotide probe was:

5' TAAGTGTGTTATAATTTCATCGATCATGTT 3' (IL-3 II)

which corresponds to sequences within the first exon of IL-3. One of the clones isolated from the leukocyte library using the IL-3 II probe contained an 8 kb HindII/EcoRI fragment of IL-3 sequence consisting of 6.4 kb of upstream sequences and 2 kb of the coding region. This fragment was inserted into the vector pTZ18R (Pharmacia, Piscataway N.J.) previously digested with HindIII/EcoRI, resulting in the vector IL-3-pTZ18R (Eco-Hind) (FIG. 38). The IL-3 leader sequence was fused to the first codon of the luciferase gene as follows. A 900 bp PstI fragment was isolated from IL-3-pTZ18R (Eco-Hind). This fragment contains 700 bp of the IL-3 promoter along with exon 1 of IL-3 (FIG. 39), and was inserted into PTZ18R (Pharmacia, Piscataway, N.J.) previously digested with PstI, resulting in the vector IL3/PstI-pTZ18R (FIG. 39).

Four oligonucleotides (IL-lu-1 to IL-lu-4) were synthesized, with the following sequences:

5' CCGGGGTTGTGGGCACCTTGCTGCTGCA-CATATAAGGCGGGAGGTTGTTG CCAACTCTTC 3' (IL-lu-1)

5' AGTTGGCAACAACCTCCCGCCTTATAT-GTGCAGCAGCAAGGTGCCCACAA CC 3' (IL-lu-2)

5' AGAGCCCCACGAAGGACCAGAACAAGA-CAGAGTGCCTCCTGCCGATCCAA ACATGGA 3' (IL-lu-3)

5' GTTTGGATCGGCAGGAGGCACTCTGTCT-TGTTCTGGTCCTTCGTGGGGCT CTGAAG 3' (IL-lu-4)

Figure 40:
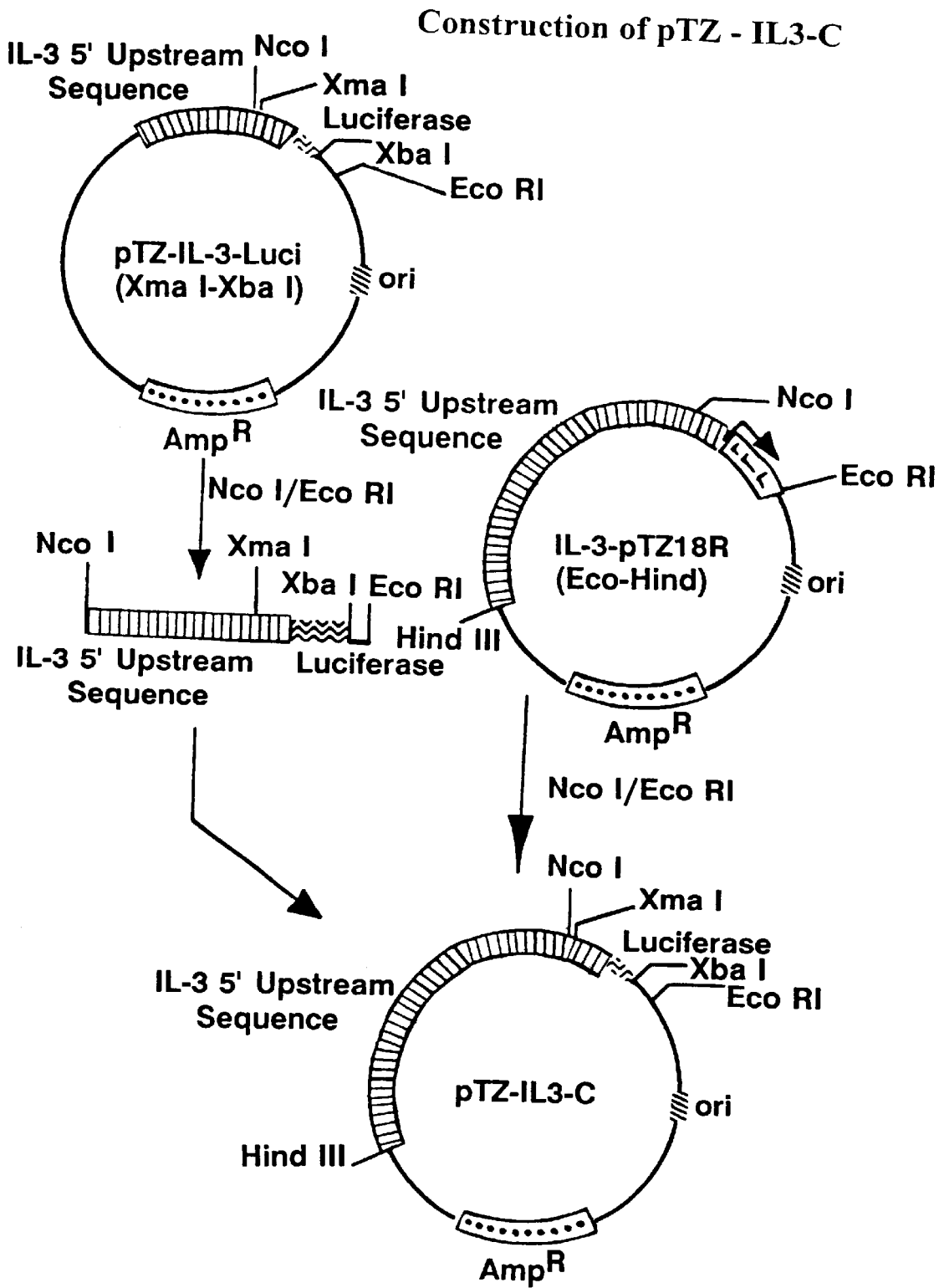
FIG. 40 is a diagrammatic representation of the construction of the plasmid pTZ-IL3-C from a 500 kb NcoI/EcoR1 fragment from pTZ-IL-3-Luci and the plasmid IL-3-pTZ18R.
Figure 41:
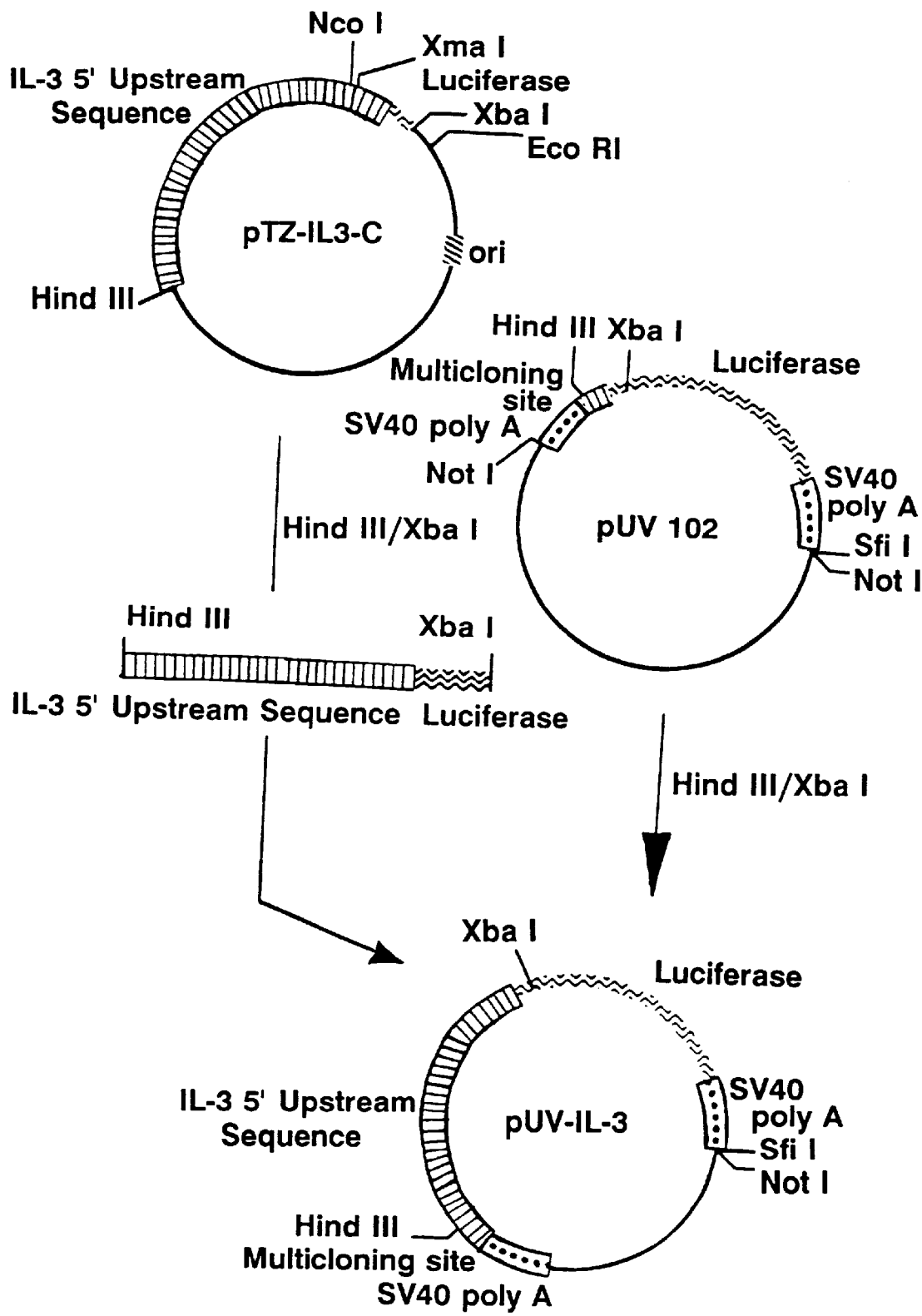
FIG. 41 is a diagrammatic representation of the construction of the plasmid pUV-IL-3 from a 6.4 kb Hind III/XbaI fragment from pTZ-IL3-C and the plasmid pUV102.

The sequences of IL-lu-1 and IL-lu-3 correspond to 112 bases of the 3' end of the IL-3 promoter fused to the first 5 bases of the luciferase coding region. IL-lu-2 and IL-lu-4 oligonucleotides are complementary to IL-lu-I and IL-lu-3, respectively. Oligonucleotides IL-lu-1 to IL-lu-4 along with oligonucleotides pUV-3 and pUV-6 (see Section C) were annealed, ligated and inserted into IL3/PstI-pTZ18R previously digested with XmaI/EcoRI, to generate pTZ-IL-3-Luci (XmaI-XbaI) (FIG. 39). A 6 kb IL-3 promoter fragment was cloned into pUV102 as follows: a 500 kb NcoI/EcoRI fragment was isolated from pTZ-IL-3-Luci (XmaI/XbaI) and inserted into IL-3-pTZ18R (EcoRI/HindIII) previously digested with NcoI/EcoRI to yield pTZ-IL3-C (FIG. 40). A 6.4 kb HindIII/XbaI fragment was then obtained from pTZIL3-C and inserted into pUV102 previously digested with HindIII/XbaI, resulting in the vector pUV-IL-3 (FIG. 41). Finally, the 1.8 kb SfiI fragment from pTKNE03 (FIG. 19) was inserted into pUV-IL-3 previously digested with SfiI, generating the vector pIL3-102-TKNEO.

E. Construction of Single Cell Clones Containing Various Promoter-Luciferase Fusion Constructs 1. pMluci pMluci (FIG. 3) and pSV2Neo, an antibiotic resistance plasmid (34), were co-transfected into NIH/3T3 mouse fibroblast cells using the calcium phosphate precipitation method (15) with a commercially available kit (Pharmacia, Piscataway N.J.). Two days later, cells were transferred to media containing 0.4 mg/ml G418 and were grown for an additional 10–14 days. G418-resistant clones were isolated by standard methods. Once sufficient cell numbers were obtained, clones were analyzed based on several criteria: constitutive luciferase production, induction of luciferase expression by dexamethasone (1 $\mu$M, Sigma, St. Louis, Mo.), satisfactory attachment to microtiter plates used in the high-throughput screen (see section G) and acceptable standard deviation in multiple luciferase expression assays (see below for assay protocol). This analysis was carried out using the luciferase assay conditions described in sections F and G. Of the clones which satisfied the above criteria for the high throuphput screen, one clone, M10, was selected for use.

2. phGH-LUCI phGH-LUCI (FIG. 6) and pRSVNeo, an antibiotic resistance plasmid (14), were co-transfected into GC rat pituitary cells as described above. Selection of G418-resistant cell clones was described above except for using a concentration of 0.2 mg/ml G418. Analysis of the cell clones was performed as above, except that known inducers of hGH expression (10–100 nM rat growth hormone releasing factor (rGRF, Bachem, Torrance, Calif.) and 10 $\mu$M forskolin (Sigma, St. Louis, Mo.) were used in place of dexamethasone. One clone, 532, was selected for further use in the high throuhgput screen.

3. pG-LUC1 pG-LUC1 (FIG. 9) and pRSVNeo were co-transfected into 5637 human bladder carcinoma cells as described above. Selection of G418 resistant clones was as described above except for using a concentration of 0.1 mg/ml G418. Analysis of cell clones was performed as above except that a known inducer of G-CSF expression (1–5$\mu$g/ml lipopolysaccharide (LPS), *E. coli* serotype 055:b5, Difco, Detroit, Mich. or Sigma, St. Louis, Mo.) was used in place of dexamethasone. One clone, G21, was selected for use.

F. Liquid Scintillation Counter Bioluminescence Assay

To assay for luciferase expression in transient expression assays in the various transfected clones, cells were incubated with various transcriptional inducers in serum free defined media, washed 3 times with Dulbecco's phosphate-buffered saline (D-PBS, Gibco) and lysed in Lysis Buffer 1 (50 mM Tris acetate pH7.9, 1 mM EGTA, 10 mM magnesium acetate, 1 mg/ml bovine serum albumin [BSA], 0.5% Brij 58, 2 mM ATP, 100 mM dithiothreitol [DTT]). All reagents were obtained from Sigma except for DTT which was from Boehringer Mannheim. After lysis, cell debris was sedimented by brief centrifugation, and 950 $\mu$l of supernatant extract were added to a glass scintillation vial. Samples were counted individually in an LKB (Gaithersburg, Md.) scintillation counter on a setting which allows measurement of individual photons by switching off the coincidence circuit. The reaction was started by addition of 50 $\mu$l of 2 mM luciferin (Sigma, St. Louis, Mo. or Boehringer Mannheim, Indianapolis Ind.) in Buffer B (Buffer B-Lysis Buffer 1 without Brij 58, ATP and DTT) to the 950 $\mu$l of lysate. Measurement was started 20 seconds after luciferin addition and continued for 1 minute. Results were normalized to protein concentration using the Bradford protein assay (BioRad, Richmond Calif.) or to cell numbers using Trypan Blue (Sigma) exclusion counting in a hemocytometer (see section G).

G. High-Throughput (HTP) Screening

Cell plating: Dynatech Microlite 96 well plates were custom pretreated for cell attachment by Dynatech Laboratories, Inc.(Chantilly, Va.). Alternatively, the 96 well plates were treated with 50 $\mu$l per well of human fibronectin (hFN, 15 $\mu$g/ml in PBS, Collaborative Research, Bedford, Mass.) overnight at 37° C. hFN-treated plates were washed with PBS using an Ultrawash 2 Microplate Washer (Dynatech Labs), to remove excess hFN prior to cell plating. M10, 532, and G21 cells maintained in their respective serum media (with 0.2 mg/ml G418) were washed with PBS, harvested by trypsinization, and counted using a hemocytometer and the Trypan Blue exclusion method according to protocols provided by Sigma, St. Louis, Mo. Chemical Company. Cells were then diluted into serum free defined media (with 0.2 mg/ml G418), and 0.2 ml of cell suspension per well was plated onto Dynatech treated plates (532 and G21) or hFN-treated plates (M10) using a Cetus Pro/Pette (Cetus, Emeryville Calif.). Plates were incubated overnight at 37° C. in a humidified 5% $CO_2$ atmosphere.

Addition of Chemicals to Cells: Chemicals from the Oncogene Science file were dissolved in DMSO at concentrations of 3–30 mg/ml. A liquid handling laboratory work station (RSP 5052, Tecan U.S. Chapel Hill, N.C.) was used to dilute the chemicals (three dilutions; 5 fold, 110 fold, and 726 fold). 10 µl of each dilution were added to each of quadruplicate samples of cells contained in the wells of 96-well Dynatech Microlite Plates. Cell plates were then shaken on a microplate shaker (Dynatech, medium setting, 30 sec.) and incubated for 6 hours at 37° C., 5% $CO_2$.

Bioluminescence Assay: After incubation with OSI-file chemicals, cell plates were washed 3 times with PBS using an Ultrawash 2 Microplate Washer (Dynatech Labs) and 75 µl of Lysis Buffer 2 were added to each well (Lysis Buffer 2 is the same as Lysis buffer 1 exept that the ATP and DTT concentrations were changed to 2.67 mM and 133 mM, respectively). Bioluminescence was initiated by the addition of 25 µl 0.4 µM Luciferin in Buffer B to each well, and was measured in a Dynatech ML 1000 luminometer following a 1 minute incubation at room temperature. Data were captured using Lotus-Measure (Lotus) software and processed by custom-designed macros written in Lotus.

H. Isolation of Total Cellular RNA

Total cellular RNA was isolated from the G21 cell clone or from untransfected 5637 cells following incubation for 6 hours with various transcriptionally modulating chemicals identified in the high-throughput screen. Cells were grown in serum free medium as described above. Total cellular RNA was isolated using the RNAZol method (CINNA/BIOTECX, Friendswood, Tex., Laboratories International, Inc.). Cells were resuspended and lysed with RNAZol solution (1.5 ml/9 cm petri dish) and the RNA was solubilized by passing the lysate a few times through a pipette. Chloroform was added to the homogenate (0.1 ml/1 ml), and samples were shaken for 15 seconds followed by a 5 minute incubation on ice. After centrifuging for 10 minutes, the upper phase was collected and an equal volume of isopropanol was added. Samples were incubated for 45 minutes at −20° C., and the RNA was pelleted for 15 minutes at 12,000×g at 4° C. The RNA pellet was then washed with 70% ethanol and dried briefly under vacuum.

I. Northern Blotting

Total cellular RNA was isolated from 5637 cells following incubation with chemicals as described above and electrophoresed in a 1% Agarose-lM Formaldehyde gel. The RNA was transferred to Duralon-UV nylon filters (Stratagene, La Jolla, Calif.) using the manufacturer's recommended protocol. The filters were prehybridized for 4 hours (prehybridizing solution=5×SSC, 50 mM sodium pyrophosphate, 10×Denhardt's solution, 10% dextran sulfate, 7% SDS and 250 µg/ml denatured ssDNA) and then hybridized in the same solution for 16 hours at 65° C. in the presence of G-CSF or Beta-Actin (Oncor, Gaithersburg, Md.) specific probes. The G-CSF probe was a 0.6 kb AflII to Xhol fragment which contained most of exon 5 of the human G-CSF gene. The β-actin probe was used as a control probe to normalize for the total amount of RNA. The probes were labeled with alpha-$^{32}$P dCTP using a random primed DNA labeling kit (Amersham, Arlington, Ill.). Following hybridization, filters were first probed with, G-CSF-and Fusion reprobed with B-Actin Probe were washed three times at room temperature with 1×SSC, 0.13% SDS and three times at 65° C. with 0.2×SSC, 0.1% SDS. Filters were first probed with G-CSF-and then reprobed with β-actin-probe. Exposure to x-ray films was performed overnight. Bands were excised and counted in a liquid scintillation counter (LKB, Gaithersburg, Md.), and counts obtained with the G-CSF specific probe were normalized relative to the counts obtained with the B-Actin specific probe.

RESULTS

A. Validation of Cell Lines

Figure 42:
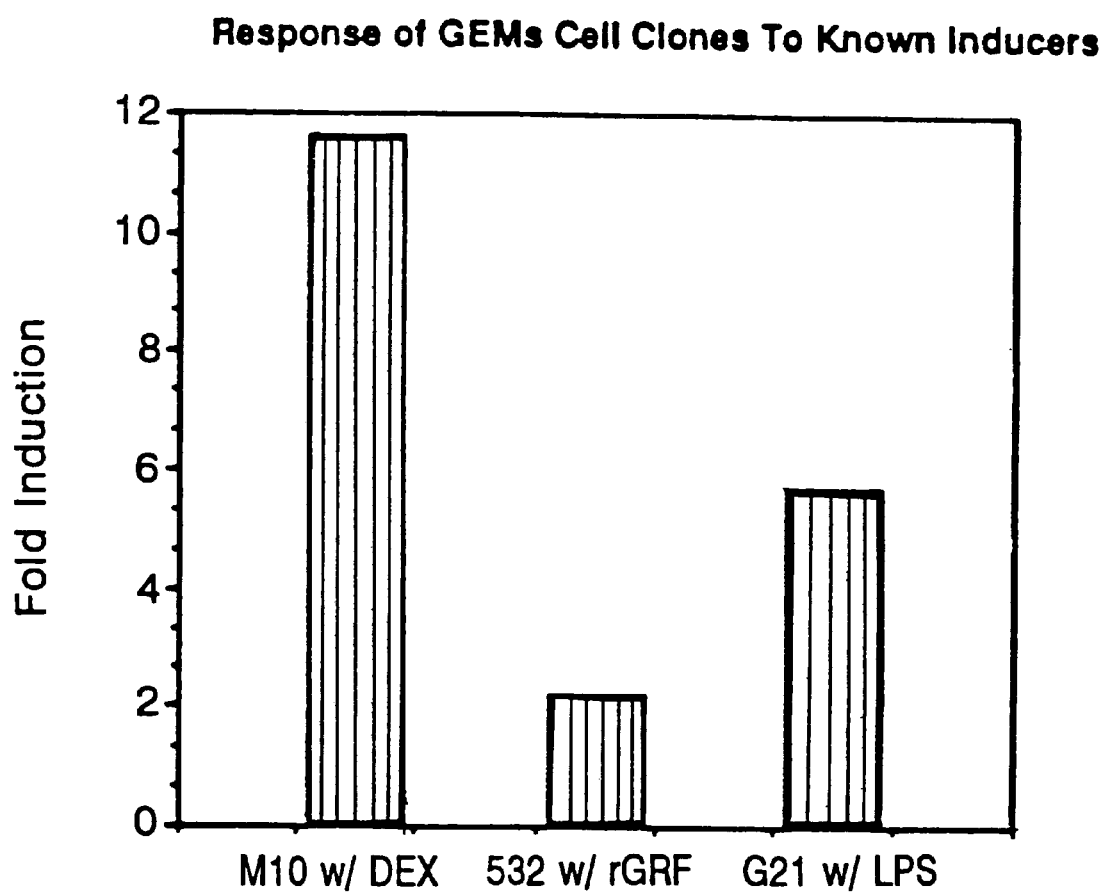
FIG. 42 is a bar graph illustrating induction of luciferase expression in reporter cell lines containing MMTV (M10), human growth hormone (532), and human G-CSF (G21) promoter sequences, in response to known transcriptional inducers.

Prior to initiation of drug screening, it was demonstrated that the transfected promoter-luciferase fusion plasmids were reacting to transcriptional inducers in a manner as predicted based on the published literature. As shown in FIG. 42, all three transfected cell clones chosen responded to inducers which have been reported to stimulate the endogenous genes; the MMTV-luciferase containing clone M10 was stimulated 11.6 fold by 1 µM dexamethasone, the hGH-luciferase containing clone 532, was stimulated 2.2 fold by 100 nM rat growth hormone releasing factor (GRF), and the hG-CSF containing clone G21 was stimulated 5.7 fold by 5 µg/ml lipopolysaccharide (LPS).

Figure 43:
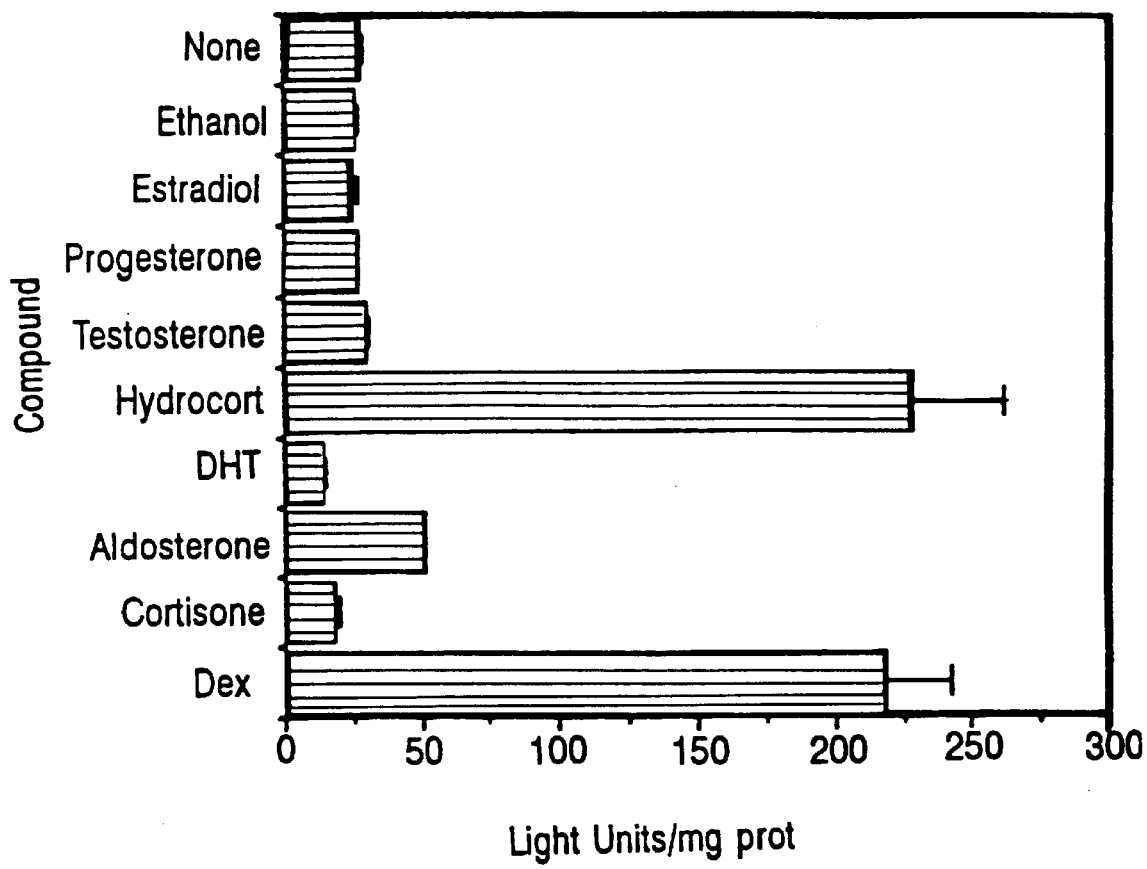
FIG. 43 is a bar graph illustrating the effect of steroids on luciferase expression in the MMTV reporter cell line M10.

It was also demonstrated that certain steroidal chemicals other than dexamethasone modulated luciferase expression in the cell clone M10, which harbours the MMTV promoter-luciferase fusion construct. As shown in FIG. 43, dexamethasone stimulated the MMTV promoter in cell clone M10 (mouse fibroblast origin), while progesterone did not. It has been shown that a rat fibroblast cell line which contains high levels of glucocorticoid receptor but low levels of progesterone receptor, shows stimulation of the MMTV promoter by the glucocorticoid dexamethasone but not by progesterone (7). In addition, FIG. 43 shows that the mineralocorticoid aldosterone stimulates clone M10, as is expected based on previously published work which indicates that aldosterone can act through the glucocorticoid receptor to stimulate the MMTV promoter (6).

B. High-Throughput Drug Screen

Figure 44:
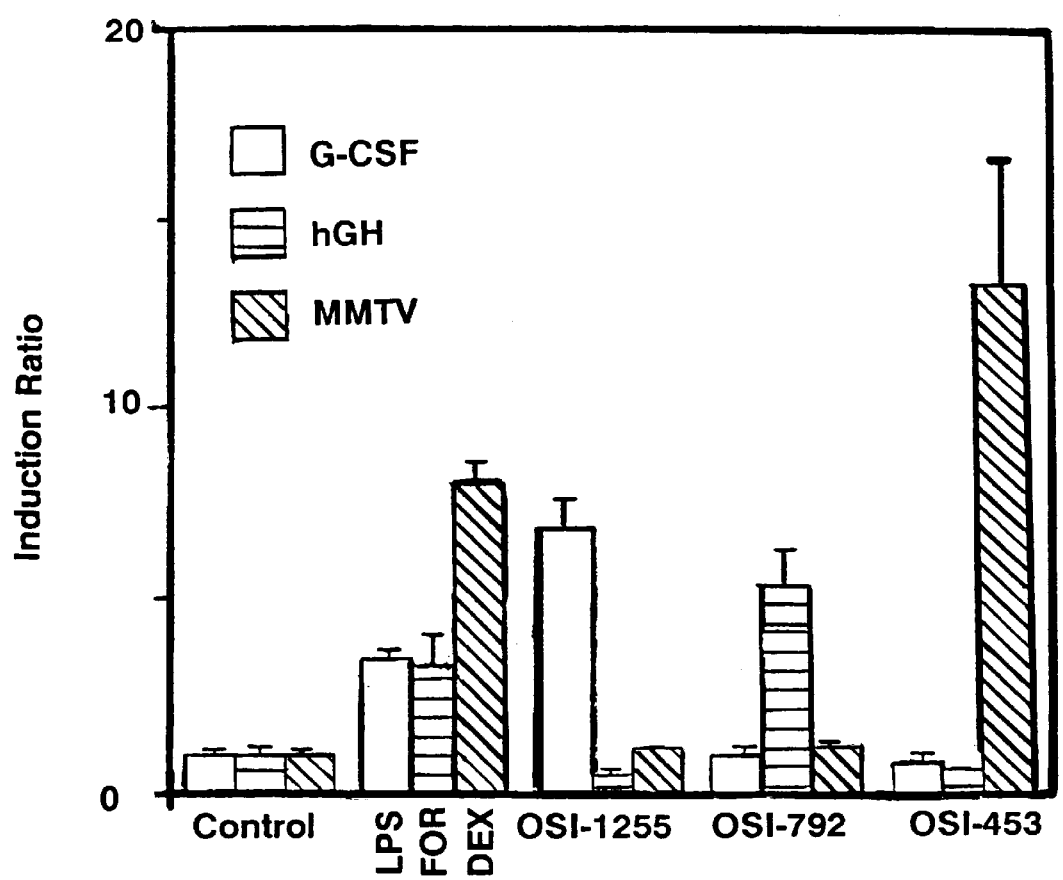
FIG. 44 is a bar graph illustrating specific induction of luciferase expression in reporter cell lines for MMTV (M10), human growth hormone (532) and human G-CSF (G21) promoters in response to chemicals identified in a high throughput screen and known transcriptional inducers.
Figure 45:
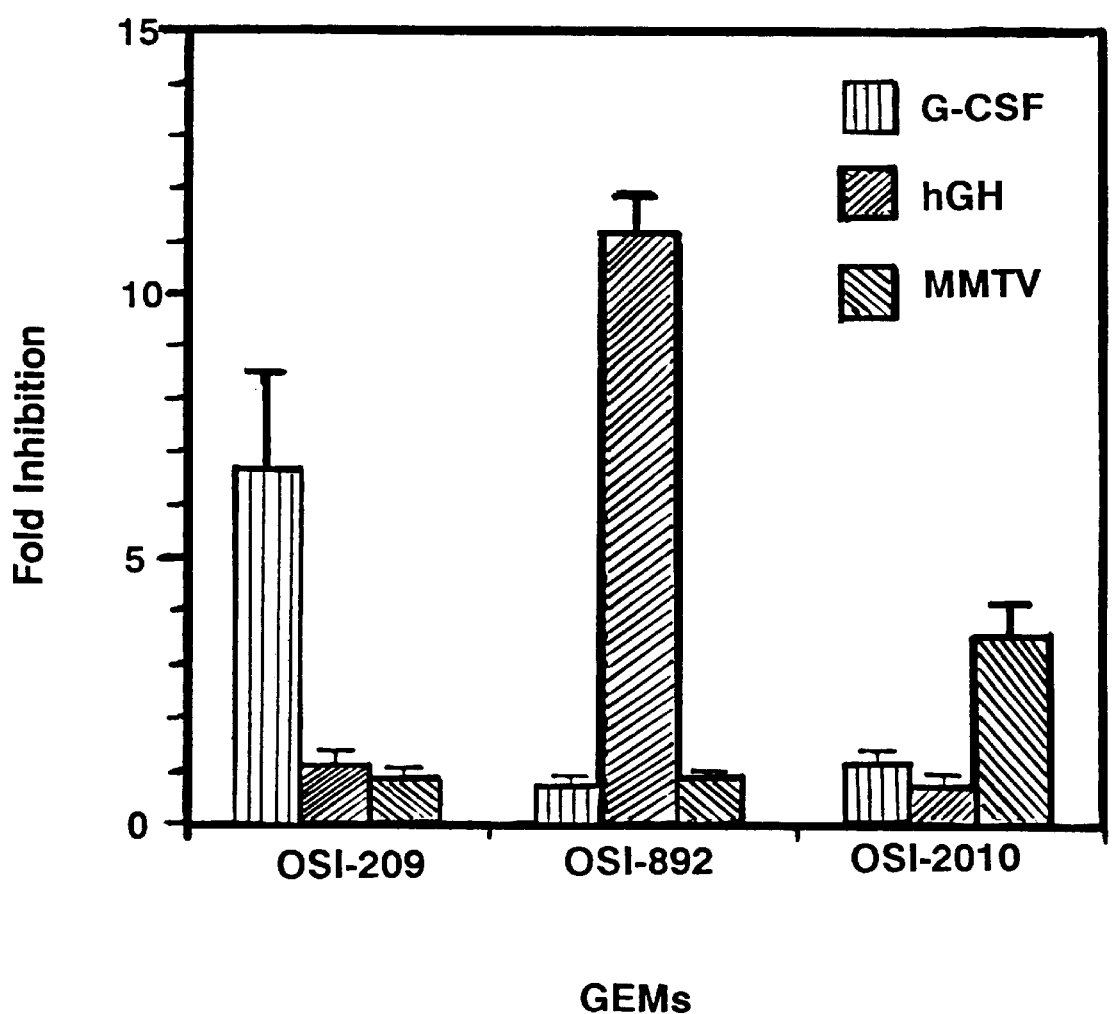
FIG. 45 is a bar graph illustrating specific inhibition of luciferase expression in reportor cell lines for MMTV (M10), human growth hormone (532), and human G-CSF (G21) in response to chemicals identified in a high throughput screen.

Table 1 shows a summary of the results of a one-week, high-throughput screen of 2,000 chemicals to identify those chemicals specifically stimulating or inhibiting transcription from the G-CSF, hGH or MMTV promoters. This screen concurrently tested chemicals at three concentrations on quadruplicate samples of the M10, 532 and G21 cell lines. A minimum stimulation of one promoter, to the degree indicated, and less than 50% activation of the other two promoters was required for a chemical to be considered a selective activator. A minimum inhibition of 3 fold of one promoter and less than 20% inhibition of the other two promoters was required for a chemical to be considered a selective inhibitor. Table 2 gives the names and induction or inhibition ratios of the lead chemicals identified for each promoter. FIG. 44 illustrates the transcriptional stimulation and FIG. 45 the transcriptional inhibition observed with some of the lead chemicals. Some of the chemicals activating G-CSF transcription fell into conspicuous groups of analogs (Table 2; Group A and B). Although not specifically indicated in Table 2, groups of homologs and analogs can also be found for G-CSF-inhibiting as well as hGH-activating chemicals.

TABLE 1

SUMMARY OF HIGH-THROUGHPUT SCREEN

Number (%) of Chemicals Which Activate Expression:

| Promoter | 2–3 Fold | 3–5 Fold | 5–7 Fold | 7–10 Fold | >10 Fold | Total |
|---|---|---|---|---|---|---|
| G-CSF | NA | 23 (1.1%) | 10 (0.5%) | 3 (0.15%) | 2 (0.10%) | 38 (1.9%) |
| hGH | NA | NA | 12 (0.6%) | 5 (0.03%) | 6 (0.03%) | 23 (1.14%) |
| MMTV | 15 (0.7%) | 1 (0.05%) | 0 (0%) | 1 (0.05%) | 1 (0.05%) | 18 (0.9%) |

Number (%) of Chemicals Which Inhibit Expression >3 Fold

| Promoter | | |
|---|---|---|
| G-CSF | 7 | (0.35%) |
| hGH | 42 | (2.1%) |
| MMTV | 1 | (0.05%) |

TABLE 2

FOLD INDUCTION RELATIVE TO SOLVENT CONTROL

| Chemical # | GCSF | hGH | MMTV |
|---|---|---|---|
| A) TRANSCRIPTIONAL ACTIVATORS | | | |
| G-CSF: | | | |
| 40 | 5.62 | 0.62 | 0.27 |
| 58 | 6.03 | 0.17 | 0.42 |
| 237 | 4.77 | 0.06 | 0.62 |
| 254 | 4.09 | 0.90 | 0.98 |
| 364 | 3.67 | 1.18 | 1.07 |
| 473 | >3 | 0.50 | 0.87 |
| 542 | 6.28 | 1.08 | 1.26 |
| 543 | 7.17 | 0.72 | 0.98 |
| 878 | 3.84 | 1.17 | 0.78 |
| 1025 | 4.09 | 0.98 | 1.24 |
| 1234 | 4.97 | 0.51 | 1.03 |
| 1255 | 6.74 | 0.43 | 1.09 |
| 1374 | 11.03 | 0.05 | 1.05 |
| 1375 | 8.94 | 0.04 | 1.37 |
| 1376 | 6.37 | 0.04 | 1.32 |
| 1397 | 3.63 | 0.57 | 1.13 |
| 1482 | 3.99 | 0.54 | 1.07 |
| 1483 | 4.64 | 0.38 | 1.09 |
| 1521 | 3.59 | 0.73 | 0.92 |
| 1583 | 5.82 | 0.12 | 0.88 |
| 1592 | 3.20 | 0.74 | 1.34 |
| 1783 | 6.55 | 0.32 | 0.89 |
| 1793 | 9.50 | 0.52 | 1.21 |
| 1794 | 3.29 | 0.34 | 0.63 |
| 2001 | 3.11 | 0.74 | 1.12 |
| 2030 | 5.53 | 0.67 | 0.87 |
| 2096 | 3.27 | 0.61 | 0.89 |
| 2097 | 5.09 | 0.88 | 1.22 |
| 2129 | 3.23 | 0.75 | 0.95 |
| GROUP A: | | | |
| 378 | 4.12 | 0.26 | 0.59 |
| 423 | 2.39 | 0.56 | 0.64 |
| 427 | 3.14 | 0.43 | 0.71 |
| 836 | 3.20 | 0.23 | 0.58 |
| 1776 | 3.50 | 0.15 | 1.36 |
| 1904 | 4.12 | 0.54 | 0.82 |
| GROUP B: | | | |
| 670 | >3 | 0.52 | 0.79 |
| 1780 | 20.39 | 0.38 | 1.15 |
| GROUP A AND B: | | | |
| 80 | 5.87 | 0.66 | 0.83 |
| hGH: | | | |
| 70 | 0.43 | 9.26 | 0.85 |
| 299 | 0.53 | 5.46 | 0.47 |
| 322 | 0.60 | 11.18 | 1.12 |
| 325 | 0.14 | 5.42 | 1.0 |
| 552 | 0.81 | 5.31 | 0.86 |
| 790 | 0.01 | 5.94 | 0.58 |
| 792 | 0.94 | 5.31 | 1.21 |
| 856 | 0.28 | 6.49 | 0.42 |
| 1004 | 0.85 | 6.48 | 1.22 |
| 1160 | 0.38 | 5.79 | 0.80 |
| 1251 | 0.14 | 15.19 | 0.33 |
| 1337 | 0.07 | 15.87 | 0.23 |
| 1499 | 0.24 | 5.55 | 0.61 |
| 1550 | 0.04 | 5.44 | 0.87 |
| 1552 | 1.23 | 7.26 | 0.52 |
| 1561 | 0.23 | 8.05 | 0.48 |
| 1598 | 0.72 | 5.32 | 1.27 |
| 1678 | 0.36 | 7.08 | 0.89 |
| 1740 | 0.74 | 17.77 | 0.87 |
| 1747 | 0.78 | 6.16 | 0.86 |
| 1804 | 1.05 | 9.41 | 0.49 |
| 1876 | 0.87 | 11.91 | 0.40 |
| 1881 | 0.21 | 18.87 | 0.69 |
| MMTV: | | | |
| 189 | 1.06 | 1.47 | 2.80 |
| 453 | 0.79 | 0.58 | 13.30 |
| 519 | 1.15 | 0.68 | 2.76 |
| 562 | 1.10 | 0.15 | 2.34 |
| 629 | 0.85 | 1.05 | 2.48 |
| 633 | 1.02 | 0.86 | 2.46 |
| 765 | 0.96 | 1.30 | 2.66 |
| 828 | 1.47 | 1.34 | 2.20 |
| 848 | 0.75 | 1.28 | 2.43 |
| 944 | 1.15 | 0.91 | 2.10 |
| 1269 | 0.72 | 0.91 | 2.18 |
| 1316 | 0.74 | 1.39 | 2.33 |
| 1318 | 1.13 | 0.85 | 2.41 |
| 1384 | 1.33 | 0.50 | 2.43 |
| 1573 | 1.49 | 0.34 | 4.30 |
| 2064 | 0.82 | 1.10 | 2.53 |
| 2148 | 0.45 | 0.92 | 2.82 |
| 2191 | 0.37 | 0.35 | 7.32 |
| B) TRANSCRIPTIONAL INHIBITORS | | | |
| G-CSF: | | | |
| 209 | 6.66 | 1.08 | 0.81 |
| 371 | 11.11 | 0.41 | 0.89 |
| 660 | 10.0 | 0.34 | 1.04 |
| 798 | 4.76 | 0.90 | 0.68 |
| 2009 | 3.70 | 0.57 | 0.64 |
| 2002 | 5.26 | 0.65 | 1.23 |
| 2121 | 4.76 | 0.40 | 1.14 |
| hGH: | | | |
| 183 | 0.72 | 4.00 | 0.70 |
| 240 | 0.63 | 5.26 | 0.80 |
| 443 | 0.60 | 4.76 | 0.79 |
| 512 | 0.81 | 5.26 | 0.68 |
| 541 | 0.90 | 6.25 | 0.86 |
| 556 | 0.73 | 33.33 | 0.87 |
| 561 | 0.62 | 5.00 | 0.05 |
| 577 | 0.64 | 4.00 | 0.68 |
| 578 | 0.65 | 4.00 | 0.91 |
| 630 | 0.70 | 3.57 | 0.74 |
| 640 | 0.64 | 5.00 | 0.59 |
| 759 | 0.64 | 5.88 | 0.95 |
| 764 | 0.82 | 4.54 | 0.59 |

TABLE 2-continued

| | FOLD INDUCTION RELATIVE TO SOLVENT CONTROL | | |
|---|---|---|---|
| Chemical # | GCSF | hGH | MMTV |
| 875 | 0.69 | 6.25 | 0.80 |
| 892 | 0.68 | 11.11 | 0.87 |
| 893 | 0.74 | 11.11 | 0.90 |
| 920 | 0.56 | 3.84 | 0.84 |
| 921 | 0.72 | 3.44 | 0.86 |
| 942 | 0.80 | 6.25 | 0.63 |
| 970 | 0.57 | 4.34 | 1.07 |
| 1591 | 0.56 | 5.55 | 0.96 |
| 1604 | 0.77 | 5.00 | 0.97 |
| 1635 | 0.71 | 9.09 | 0.99 |
| 1640 | 0.79 | 5.00 | 0.59 |
| 1641 | 0.83 | 5.55 | 0.60 |
| 1648 | 0.86 | 7.69 | 1.00 |
| 1651 | 0.69 | 3.57 | 0.70 |
| 1655 | 0.54 | 4.76 | 0.82 |
| 1703 | 0.76 | 10.00 | 0.90 |
| 1704 | 0.17 | 4.16 | 0.94 |
| 1705 | 0.54 | 14.28 | 0.62 |
| 1712 | 0.74 | 8.33 | 0.94 |
| 1720 | 0.65 | 4.76 | 0.66 |
| 1764 | 0.55 | 7.14 | 0.82 |
| 1770 | 0.54 | 10.00 | 0.57 |
| 1771 | 0.71 | 10.00 | 0.72 |
| 1773 | 0.62 | 10.00 | 0.67 |
| 1890 | 0.80 | 5.26 | 0.58 |
| 2035 | 0.57 | 7.14 | 0.69 |
| 2036 | 0.58 | 4.34 | 0.81 |
| 2037 | 0.51 | 4.00 | 0.50 |
| MMTV: | | | |
| 2010 | 0.80 | 0.63 | 3.57 |

C. Effects of Lead Chemicals on Endogenous G-CSF mRNA Levels

Figure 46:
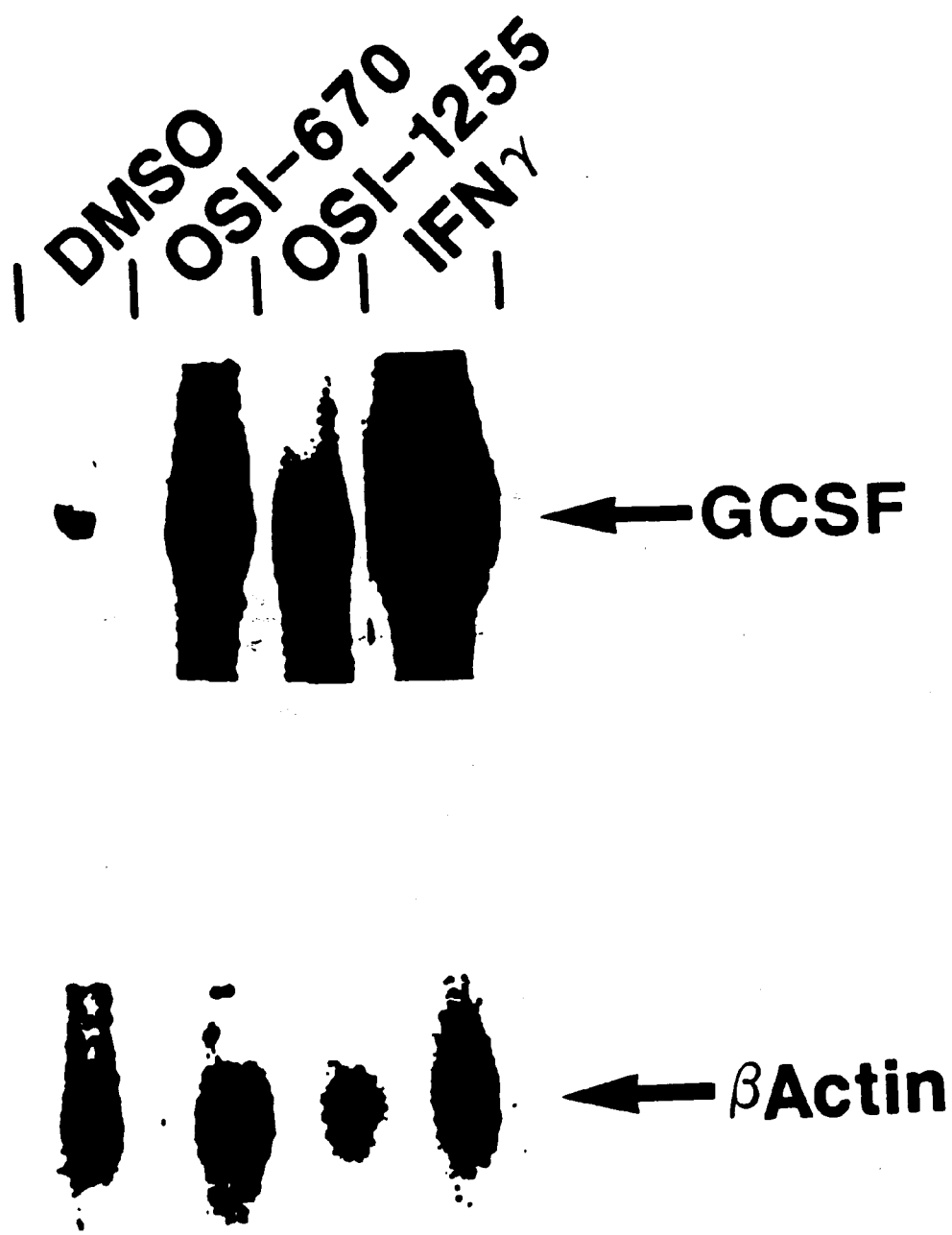
FIG. 46 is an autoradiograph of a Northern blot illustrating increased G-CSF mRNA production by the human epithelial cell line U5637 in response to chemicals #670 and #1255 and IFN-gamma as compared to the solvent DMSO. Reprobing with beta-actin was used to normalize for the amount of mRNA that had been loaded onto the gel.

Northern blot analysis was used to demonstrate the stimulatory effects of lead chemicals #670 and #1255 on endogenous G-CSF mRNA levels. As shown in FIG. 46, both OSI #670 and #1255 stimulated production of G-CSF mRNA, as shown by a G-CSF-specific probe, but not of β actin mRNA, as shown by a β-actin-specific probe. Also shown are the effects of the solvent, DMSO, used to dissolve the chemicals and a proteinaceous positive regulator, interferon-γ. From these data it is concluded that chemicals, which induce luciferase expression from specific promoters, in plasmids stably integrated into cells, are also capable of stimulating mRNA production from the corresponding endogenous promoters without using a reporter system.

D. Dose response Analysis of Structurally Related Lead Chemicals

Figure 47:
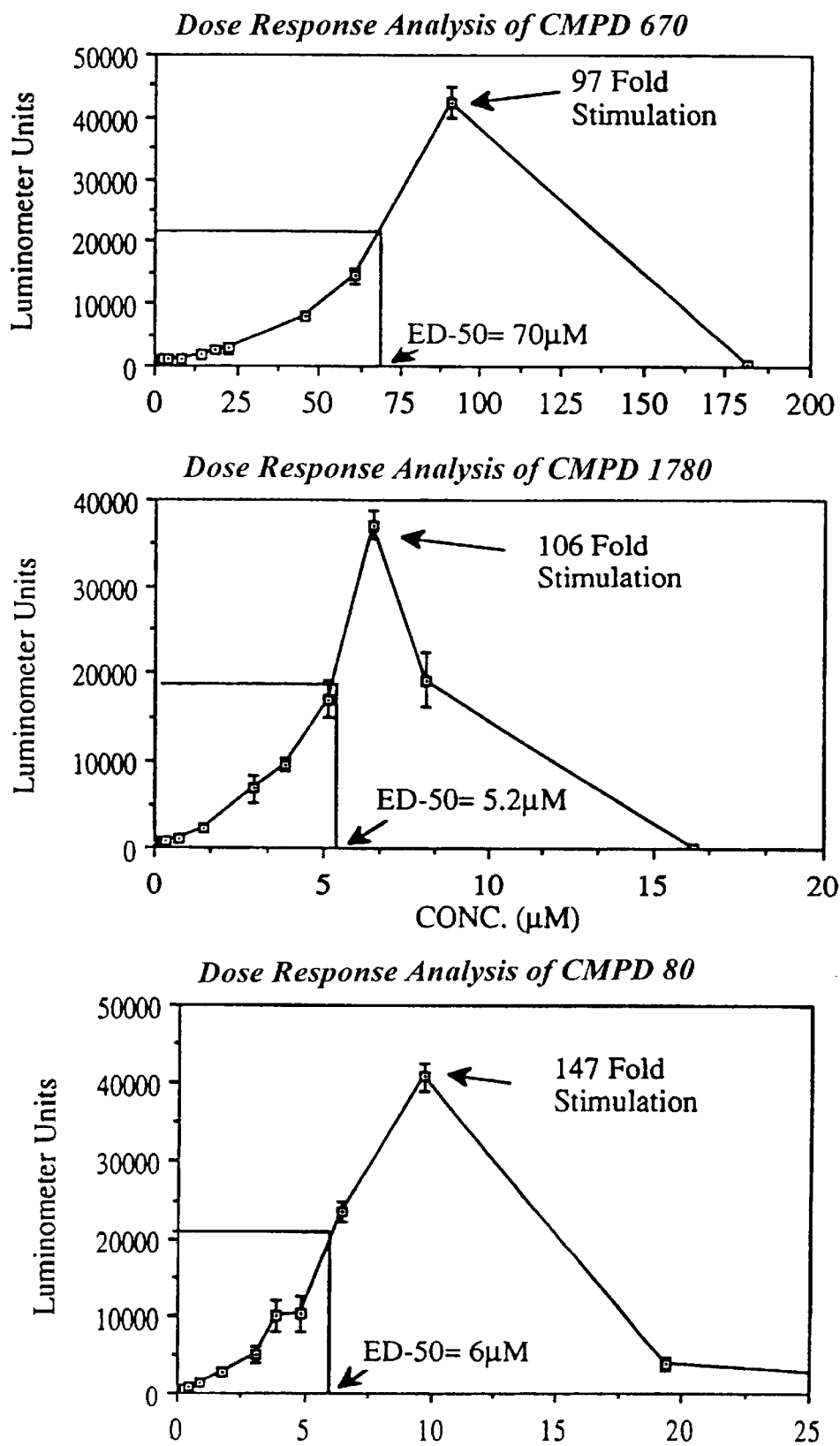
FIG. 47 illustrates a dose response analysis of chemicals #80, #670, and #1780 using the G-CSF reporter cell line G21. The amount of luciferase expression is indicated in arbitrary units.

Among the chemicals which specifically activated the G-CSF promoter were groups of structural homologs. Three such homologs, #80, #670, and #1780, belong to groups listed in Table 2. These three structurally related chemicals all specifically activated the G-CSF promoter. Dose response graphs obtained with chemicals #80, #670, and #1780 are shown in FIG. 47. Although these chemicals all demonstrate large maximal stimulations, it is clear that their potencies, as measured by their $ED_{50}$'s (concentration of chemical resulting in 50% maximal stimulation)., show wide variability (5–70 μM)).

REFERENCES

1. Angel, P., Baumann, I., Stein, B., Delius, H., Rahmsdorf, H. J. and Herrlich, P. (1987) 12-0-tetradecanoyl-phorbol-13-acetate (TPA) induction of the human collagenase gene is mediated by an inducible enhancer element located in the 5'-flanking region. Mol. Cell. Biol., 7:2256.
2. Angel, P., Tmagawa, M., Chiu, R. Stein, B., Imbra, R. J., Rahmsdorf, H. J., Jonat, C., Herrlich, P. and Karin,M. (1987) Phorbol ester-inducible genes contain a common cis element recognized by a TPA-modulated trans-acting factor, Cell, 49:729.
3. Arnheim, N. (1979) Characterization of mouse ribsomal gene fragments purified by molecular cloning, Gene, 7:83.
4. Bancroft, F. C., Wu, G. J., and Zubay, G. (1973) Proc. Natl. Acad. Sci. USA, 73:29.
5. Bottenstein, J., Hayashi, I., Hutchings, S., Masui, H., Mather, J., McClure, D. B., Ohasa, S., Rizzino, A., Sato G., Serrero, G., Wolfe, R., and Wu, R. (1979) The growth of cells in serum-free hormone-supplemented media, Methods in Enzymology, 58:94.
6. Cato, A. C. B. and Weinmann, J. (1988) Mineralcorticoid regulation of transcription of transfected mouse mammary tumor virus DNA in cultured kidney cells, J. Cell Biol., 106(6):2119.
7. Cato, A. C. B., Miksicek, R., Schutz, G., Arnemann, J., and Beato, M. (1986) The hormone regulatory element of mouse mamary tumor virus mediates progesterone induction, EMBO J., 5(9):2237.
8. De Wet, J. R., Wood, K. V., Helinski, D. R., and DeLuca, M. (1985) Cloning of firefly luciferase cDNA and the expression of active luciferase in *Escherichia coli*, Proc. Natl. Acad. Sci. USA, 82:7870.
9. Denison, M. S., Fisher, Springfield, N. J., J. M., and Whitlock, Jr., J. P. (1988) Inducible, receptor-dependent protein-DNA interactions at a dioxin-responsive transcriptional enhancer, Proc. Natl. Acad. Sci. USA, 85:2528.
10. Edelman, A. M., Blumenthal, D. R. and Krebs, E. G. (1987) Protein Serine/Threonine Kinases Ann. Rev. 56:567–613.
11. Engebrecht, J. M., Simon, M., and Silverman, M. (1985) Measuring gene expression with light. Science, 227:1345.
12. Evans, R. M. and Hollenberg, S. M. (1988) Zinc fingers: Gilt by assocation, Cell, 52:1.
13. Evans, R. M. (1988) The steroid and thyroid hormone receptor superfamily, Science, 240:889.
14. Gorman, C. (1985) Vectors used in mammalian cell expression. In DNA Cloning, Vol. II (D. M. Glover, ed). IRL Press, Washington, D.C.
15. Graham, F. L. and Van der Ed, A. J. (1973) A new technique for the assay of human adenovirus 5 DNA, Virology, 52:456.
16. Hatzopoulos, A. K., Schlokat, U., and Gruss, P. (1988) Enhancers and other cis-acting regulatory sequences. In Transcription and Splicing. (Hanes, B. D. and Glover, D. M., eds.) IRL Press, Washington, D.C., Vol. 1, p. 43.
17. Hayashi, I., Larner, J., and Sato, G. (1978) Hormonal growth control of cells in culture., In Vitro, 14:23.
18. Hoeffler, J. P., Meyer, T. E., Yun, Y., Jameson, J. L., and Habener, J. F. (1988) Cyclic AMP-responsive DNA-binding protein: Structure based on a cloned placental cDNA, Science, 242:1430.
19. Hoopes, B. C. and McClure, W. R. Strategies in Regulation of Transcription Initiation. In *Escherichia coli* and *Salmonella Typhimurium*: Cellular and Molecular Biology (F. C. Neidhardt, J. L. Ingraham, K. Brooks Low, B. Magasanik, M. Schaechter, eds.) Vol. 2, p. 1231.
20. Kaushansky, K;, O'Hara, P. J., Berkner, K., Segal, G. M., Hagen, F. S., and Adamson, J. W. (1986) Genomic cloning, characterization, and multilineage growth-promoting activity of human granulocyte-macrophage colony-stimulating factor, Proc. Natl. Acad. Sci. USA, 83:3101.

21. Krainer, A. R. and Maniatis, T. (1988) RNA splicing. In Transcription and Splicing (Hames, B. D. and Glover, D. M., eds.) IRL Press, Washington, D.C., Vol. 1.
22. La Thangue, N. B. and Rigby, P. W. J. (1988) Transacting protein factors and the regulation of eukaryotic transcription. In Transcription and Splicing (Hames, B. D. and Glover, D. M., eds) IRL Press, Washington, D.C., Vol. 1.
23. Ladner, M. B., Martin, G. A., Noble, J. A., Nikoloff, D. N., Tal, R., Kawaski, E. S., and Wnite, T. J. (1987) Human CSF-1;gene structure and alternative splicing of mRNA precursors, EMBO J., 6:2693.
24. Landschulz, W. H., Johnson, P. F., and McKnight, S. L. (1988) The leucine zipper: A hypothetical structure common to a new class of DNA binding proteins, Science, 240:1759.
25. Lefevre, C., Imagawa, M., Dana, S., Grindlay, J., Bodner, M., and Karin, M. (1987) Tissue-specific expression of the human growth hormone gene is conferred in part by the binding of a specific trans-acting factor, EMBO J., 6:971.
26. Levine, M. and Hoey, T. (1988) Homeobox proteins as sequence-specific transcription factors, Cell, 55:537.
27. Lin, F. K., Suggs, S., Lin, C. H, Browne, J. K., Smalling, R, Egrie, J. C., Chen, K. K., Fox, G. M., Martin, F., Stabinsky, Z., Badrawi, S. M., Lai, P. H., and Goldwasser, E. (1985) Cloning and expression of the human erythropoietin gene, Pro. Natl. Acad. Sci. USA, 82:7580.
28. Maniatis, T., Goodbourn, S. and Fischer, J. A. (1987) Regulation of inducible and tissue-specific gene expression, Science, 236:1237.
29. Matthews, B. W. (1987) Cro repressor structure and its interaction with DNA. In DNA: Protein Interactions and Gene Regulation (E. B. Thompson and J. Papaconstantinou, eds.) University of Texas Press, Austin.
30. McClure (1985) Ann. Rev. Biochem., 54:171.
31. McKnight, S. L. (1982) Functional relationships between transcriptional control signals of the thymidine kinase gene of herpes simplex virus, Cell, 31:355.
32. Nagata, S., Tsuchiya, M., Asano, S., Yamamoto, O., Hirata, Y., Kubota, N., Oheda, M., Nomura, H. and Yamazaki, T. (1986) The chromosomal gene structure and two mRNAs for human granulocyte colony-stimulating factor, EMBO J., 5:575.
33. Ow, D. W., Wood, K. U, Deluca, M, Dewet, J. R., Melinski, D., and Howell, S. H. Science 234:856–859
34. Pouwels, Ph. H., Enger-Valk, B. E., and Brammar, W. J. (1985) Cloning Vectors. Elsevier Science Publishers, B. V., Amsterdam.
35. Proudfoot, N. J. and Whitelaw, E. (1988) Termination and 3' end processing of eukaryotic RNA. In Transcription and Splicing (Hames, B. D. and Glover, D. M., eds.) ERL Press, Washington, D.C., Vol. 1, p. 97.
36. Schlief, R. The L-Arabinose Dperon. In *Escherichia coli* and *Salmonella typhimurium*: Cellular and Molecular Biology (F. C. Neidhardt, J. L. Ingraham, K. Brooks Low, B. Maga Sanik, M. Schaecter, eds.) Vol. 2, p. 1473.
37. Schlief, R. (1988) DNA binding by proteins, Science, 241:1182.
38. Yamamoto, K. R. (1985) Steroid receptor regulated transcription of specific genes and gene networks, Ann. Rev., Genet., 19:209.
39. Yamamoto, K. K., Gonzalez, G. A., Biggs III, W. H., and Montminy, M. R. (1988) Phosphorylation-induced binding and transcriptional efficacy of nuclear factor CREB, Nature, 334:494.
40. Yang, Y. C., Ciarletta, A. B., Temple, P. A., Chung, M. P., Kovacic, S., Witek-Gianotti, J. S., Learyn, A. C., Kriz, R., Donahue, R. E., Wong, G. G., and Clark, S. C. (1986) Human IL-3 (multi-CSF): Identification by expression cloning of a novel hematopoietic growth factor related to murine IL-3, Cell, 47:3.
41. Yang, T. C. and Clark, S. C. (1988) Molecular cloning of a primate CDNA and the human gene for interleukin 3, Lymphokines, 15:375.
42. Yanofsky, C. and Crawford, I. P. The Tryptophan Operon. In *Escherichia coli* and *Salmonella typhimurium*: Cellular and Molecular Biology (F. C. Neidhardt, J. L. Ingraham, K. Brooks Low, B. Magasanik, M. Schaechter, eds.) Vol. 2, p. 1453.
43. Zhan, A., Culpepper, A., Reddy, M., Loveless, J., and Goldfarb, M. (1987) Human oncogenes detected by a defined medium culture assay, Oncogene, 1:369.

What is claimed is:

1. A method of preparing a composition which comprises:
    (a) contacting a sample which contains a predefined number of eucaryotic cells with a chemical to be tested, each cell comprising a DNA construct comprising:
        (i) a modulatable transcriptional regulatory sequence of a gene-of-interest,
        (ii) a promoter, and
        (iii) a reporter gene that produces a detectable signal, coupled to, and under the control of, the promoter, under conditions wherein the chemical if capable of acting as a transcriptional modulator of the gene-of-interest, causes a detectable signal to be produced by the reporter gene;
    (b) quantitatively determining the amount of the signal produced in (a);
    (c) comparing the amount of signal determined in (b) with the amount of signal produced and detected in the absence of any chemical being tested or with the amount of signal produced and detected upon contacting the sample in (a) with other chemicals, thereby identifying the test chemical as a chemical which causes a change in the amount of detectable signal produced by the reporter gene; and
    (d) admixing a homolog or analog of the chemical from step (c) with a carrier, thereby preparing the composition.

2. A method of preparing a composition which comprises:
    (a) separately contacting a plurality of samples each of which contains a predefined number of eucaryotic cells with different chemicals to be tested, each cell comprising a DNA construct comprising:
        (i) a modulatable transcriptional regulatory sequence which regulates initiation of transcription from a promoter of a gene-of-interest,
        (ii) a promoter which initiates transcription of the gene-of-interest, and
        (iii) a reporter gene that produces a detectable signal, coupled to, and under the control of, the promoters under conditions wherein the chemical if capable of acting as a transcriptional modulator of the gene-of-interest, causes a detectable signal to be produced by the reporter gene;
    (b) quantitatively determining the amount of the signal produced by each chemical in (a);
    (c) comparing the amount of signal determined in (b) for each chemical with the amount of signal produced and detected in the absence of any chemical being tested and/or with the amount of signal produced and detected upon contacting the sample in (a) with the different chemicals, thereby identifying the test chemical as a chemical which causes a change in the amount of detectable signal produced by the reporter gene; and (d) admixing a homolog or analog of the chemical from step (c) with a carrier, thereby preparing the composition.

3. A method of preparing a composition which comprises:
(a) contacting a sample which contains a predefined number of eucaryotic cells with a chemical to be tested, each cell comprising a DNA construct comprising:
  (i) a modulatable transcriptional regulatory sequence which regulates initiation of transcription from a promoter of a gene-of-interest,
  (ii) a promoter which initiates transcription of the gene-of-interest, and
  (iii) a reporter gene that produces a detectable product, coupled to, and under the control of, the promoter, under conditions wherein the chemical if capable of acting as a transcriptional modulator of the gene-of-interest, causes a detectable product to be produced by the reporter gene;
(b) quantitatively determining the amount of the product produced in (a) (iii);
(c) comparing the amount of product determined in (b) with the amount of product produced and detected in the absence of any chemical being tested or with the amount of product produced and detected upon contacting the sample in (a) with other chemicals, thereby identifying the test chemical as a chemical which causes a change in the amount of detectable product produced by the reporter gene; and
(d) admixing a homolog or analog of the chemical from step (c) with a carrier, thereby preparing the composition.

4. The method of claim 1, 2 or 3, wherein the sample comprises identical cells in monolayers.

5. The method of claim 1, 2 or 3, wherein the sample comprises identical cells in suspension.

6. The method of claim 1, 2 or 3, wherein the cells comprise human, animal, fungi, yeast or plant cells.

7. The method of claim 1, 2 or 3, wherein the cells comprise mammalian cells.

8. The method of claim 1, 2 or 3, wherein the predefined number of cells is from about 1 to about $5 \times 10^5$ cells.

9. The method of claim 1, 2 or 3, wherein the predefined number of cells is from about $2 \times 10^2$ to about $5 \times 10^4$ cells.

10. The method of claim 1, 2 or 3, wherein the chemical is present at a predetermined concentration from about 1.0 pM to about 20 $\mu$M.

11. The method of claim 1, 2 or 3, wherein the chemical is present at a predetermined concentration from about 10 nM to about 500 $\mu$M.

12. The method of claim 1, 2 or 3, wherein the chemical is present in a predetermined amount based upon the volume of the sample.

13. The method of claim 1, 2 or 3, wherein the contacting is effected from about 1 hour to about 24 hours.

14. The method of claim 1, 2 or 3, wherein the contacting is effected from about 2 hours to about 12 hours.

15. The method of claim 1, 2 or 3, wherein the contacting is effected at more than one concentration of the chemical to be tested.

16. The method of claim 1, 2 or 3, wherein the modulatable transcriptional regulatory sequence comprises a cloned genomic regulatory sequence.

17. The method of claim 1, 2 or 3, wherein the cells comprise a single DNA construct.

18. The method of claim 1, 2 or 3, wherein the DNA construct consists essentially of at least one modulatable transcriptional regulatory sequence, the promoter and the reporter gene.

19. The method of claim 1, 2 or 3, wherein the reporter gene is inserted downstream of the promoter.

20. The method of claim 19, wherein the reporter gene was inserted by homologous recombination.

21. The method of claim 1, 2 or 3, wherein the reporter gene encodes a luciferase, chloramphenicol acetyltransferase, β glucuronidase, β galactosidase, neomycin phosphotransferase, or guanine xanthine phosphoribosyltransferase.

22. The method of claim 1, 2 or 3, wherein the reporter gene expresses a polypeptide and the detectable signal is or is produced by the polypeptide so expressed.

23. A method of preparing a composition according to claim 1, 2 or 3, further comprising screening the test chemical or chemicals against one or more additional genes of interest by performing steps (a) through (c) for each additional.

24. The method of claim 23, wherein more than about $10^3$ samples per week are contacted with different test chemicals.

25. The method of claim 23, wherein the genes of interest are in a plurality of samples.

26. The method of claim 23, wherein the plurality of samples comprises more than about $10^4$ samples.

* * * * *